(12) United States Patent
Shirai et al.

(10) Patent No.: US 8,000,822 B2
(45) Date of Patent: Aug. 16, 2011

(54) AUDIO REPRODUCING APPARATUS, AUDIO REPRODUCING METHOD, AND AUDIO REPRODUCING PROCESSING PROGRAM

(75) Inventors: Katsuya Shirai, Kanagawa (JP);
Yoichiro Sako, Tokyo (JP); Toshiro Terauchi, Tokyo (JP); Makoto Inoue, Tokyo (JP); Masamichi Asukai, Kanagawa (JP); Yasushi Miyajima, Kanagawa (JP); Kenichi Makino, Kanagawa (JP); Motoyuki Takai, Tokyo (JP); Kosei Yamashita, Kanagawa (JP)

(73) Assignee: Sony Corporation, Tokyo (JP)

( * ) Notice: Subject to any disclaimer, the term of this patent is extended or adjusted under 35 U.S.C. 154(b) by 950 days.

(21) Appl. No.: 11/815,422

(22) PCT Filed: Jan. 31, 2006

(86) PCT No.: PCT/JP2006/301566
§ 371 (c)(1),
(2), (4) Date: Oct. 29, 2007

(87) PCT Pub. No.: WO2006/082809
PCT Pub. Date: Aug. 10, 2006

(65) Prior Publication Data
US 2009/0024233 A1    Jan. 22, 2009

(30) Foreign Application Priority Data

Feb. 3, 2005  (JP) ................... 2005-027654
Dec. 7, 2005  (JP) ................... 2005-352948
Dec. 7, 2005  (JP) ................... 2005-352949

(51) Int. Cl.
*G06F 17/00* (2006.01)

(52) U.S. Cl. ......................................... 700/94
(58) Field of Classification Search ................... 700/94; 715/760; 705/2, 27
See application file for complete search history.

(56) References Cited

U.S. PATENT DOCUMENTS
2006/0107822 A1* 5/2006 Bowen ........................... 84/612

FOREIGN PATENT DOCUMENTS
JP        55-012452       1/1980
(Continued)

OTHER PUBLICATIONS

Japanese Office Action issued on Jun. 29, 2010 corresponding to Japanese Patent Appln. No. 2005-352949.

(Continued)

*Primary Examiner* — Andrew C Flanders
(74) *Attorney, Agent, or Firm* — K&L Gates LLP

(57) ABSTRACT

An easy-to-use and user-friendly apparatus is provided that displays motivation for exercise to a user to allow the user to continue comfortably exercising. An audio signal output processor reproduces audio data and a music sound is thus emitted from a loudspeaker. The user practices exercise, such as walking or jogging, in synchronization with the tempo of the music sound. At the start of exercise, an exercise information analyzer calculates an amount of exercise of the user based on personal profile information relating to the body of the user, including the body weight, the body height, age and sex of the user received via a keyboard, and characteristic information, such as play time and tempo of reproduced music data acquired via a communication I/F and a controller. The controller outputs the amount of exercise to a display to notify the user of the amount of exercise.

19 Claims, 45 Drawing Sheets

FOREIGN PATENT DOCUMENTS

| | | |
|---|---|---|
| JP | 2003-177749 | 6/1993 |
| JP | 06-130960 | 5/1994 |
| JP | HEI 06-054093 | 7/1994 |
| JP | HEI 11-219175 | 8/1999 |
| JP | 2001-275999 | 10/2001 |
| JP | 2001-299980 | 10/2001 |
| JP | 2002-073018 | 3/2002 |
| JP | 2002-301050 | 10/2002 |
| JP | 2002-084903 | 3/2003 |
| JP | 2003-126291 | 5/2003 |
| JP | 2003-305146 | 10/2003 |

OTHER PUBLICATIONS

China P. Rep. Office Action for corresponding Application No. 200680010836.3, dated Jul. 10, 2009.

Japanese Office Action mailed on Nov. 30, 2010 for corresponding Japanese Appln. No. JP 2005-352948.

Japanese Office Action mailed on Nov. 30, 2010 for corresponding Japanese Appln. No. JP 2005-352949.

Japanese Office Action issued on Sep. 14, 2010 for corresponding Japanese Appln. No. JP 2005-352949.

* cited by examiner

FIG. 3
REPLAY MUSIC INFORMATION

| TITLE | LENGTH | SONG TEMPO |
|---|---|---|
| SONG A | 1:11 | 100 |
| SONG B | 2:22 | 120 |
| SONG C | 3:33 | 105 |
| SONG D | 2:30 | 145 |
| SONG E | 1:50 | 180 |
| SONG F | 3:00 | 80 |

FIG. 4A
REPLAY MUSIC LIST 1

| TITLE | LENGTH | SONG TEMPO | NO. OF PLAYS |
|---|---|---|---|
| SONG A | 1:11 | 100 | 50 |

FIG. 4B
REPLAY MUSIC LIST 2

| TITLE | LENGTH | SONG TEMPO | NO. OF PLAYS |
|---|---|---|---|
| SONG A | 1:11 | 100 | 5 |
| SONG C | 3:33 | 105 | 1 |
| SONG B | 2:22 | 120 | 1 |
| SONG D | 2:30 | 145 | 1 |
| SONG E | 1:50 | 180 | 30 |
| SONG B | 2:22 | 120 | 2 |
| SONG C | 3:33 | 105 | 1 |
| SONG F | 3:00 | 80 | 1 |

FIG. 5

```
                                          ~34G
┌─────────────────────────────────────────┐
│ EXERCISE AMOUNT INFORMATION             │
│                                         │
│ EXERCISE TIME        30:00 minutes      │
│ DISTANCE WALKED      3.00 km            │
│ AVERAGE SPEED        6.00 km/h          │
│ CALORIES CONSUMED    150 kcal           │
│ FAT BURNED           20 g               │
│                                         │
│ GOOD EXERCISE!                          │
└─────────────────────────────────────────┘
```

FIG. 6

DISTANCE WALKED

STRIDE = HEIGHT × 0.45 ... (1)

DISTANCE = STRIDE × NUMBER OF STEPS ... (2)

(EXAMPLE) DISTANCED WALKED BY 170-CM-TALL PERSON TO SONG OF 120 TEMPOS FOR 2 MINUTES 30 SECONDS

DISTANCE WALKED = 170 cm × 0.45 × 120 (TIMES) × (2 × 60 + 30 (seconds)) / 60 (seconds) = 22950 = 229.5 m ...(3)

FIG. 7

AVERAGE SPEED

AVERAGE SPEED = DISTANCE WALKED / TOTAL EXERCISE TIME ... (4)

(EXAMPLE) AVERAGE SPEED IF IT 3 km WALK TAKES 30 MINUTES

AVERAGE SPEED = 3.00 km / 0.5 (hours) = 6.00 km/h ... (5)

FIG. 8

ENERGY CONSUMED PER MINUTE $W_{min}$ = (35 + SPEED (m/min)) / 2000 × WEIGHT (kg) ...(6)

(EXAMPLE) CALORIES CONSUMED BY 68-kg PERSON HAVING WALKED AT SPEED OF 100 m/min FOR 60 MINUTES $W_{min}$ = (35 + 100) / 2000 × 68 = 4.59 kcal/min ...(7)
$W_{total}$ = 4.59 kcal/min × 60 min = 275.4 kcal ...(8)

FIG. 9

ENERGY CONSUMED (USING METS VALUE)

ENERGY CONSUMED (kcal)
= WEIGHT (kg) × METS VALUE × EXERCISE TIME (hours) ...(9)

(EXAMPLE) 60-kg PERSON HAVING PERFORMED EXERCISE OF 5 METS FOR 30 MINUTES

ENERGY CONSUMED = 60 × 5 × 0.5 = 150 kcal ...(10)

METS VALUE   WALKING   4 – 7
             JOGGING   7 – 15

FIG. 10

FAT BURNED

CALORIES REQUIRED FOR BURNING 1 kg FAT 7700 kcal

FAT BURNED = ENERGY CONSUMED (kcal) / 7700 kcal × 1000 g ...(11)

(EXAMPLE) CASE OF FIG. 8 (ENERGY CONSUMED BEING 275.4 kcal)

FAT BURNED BY EXERCISE = 275.4 kcal / 7700 kcal × 1000 g = 35.77 g ...(12)

FIG. 11

EXERCISE INTENSITY  METS (METABOLIC EQUIVALENTS)

METS = [OXYGEN INHALED DURING EXERCISE] / [OXYGEN INHALED AT REST]
= (R + H + V) / R     ... (13)

1 METS EQUAL TO CONSUMED OXYGEN OF 3.5 ml/kg·minute

OXYGEN INHALED DURING EXERCISE = R + H + V (ml/kg·min)     ... (14)

R: OXYGEN CONSUMED AT REST 3.5 ml/kg·min
    H: HORIZONTAL LOCOMOTION FACTOR
        0.1 × SPEED V (m/min) (WALKING)     ... (15)
        0.2 × SPEED V (m/min) (RUNNING)     ... (16)
    V: VERTICAL LOCOMOTION FACTOR
        0.9 × SPEED V (m/min) × TILT rad (%)     ... (17)

FIG. 12

EXAMPLE)  METS VALUE FOR WALKING AT SPEED OF 6 km/h

HORIZONTAL FACTOR H = 0.1 × 100 = 10.0     ... (18)
    VERTICAL FACTOR V = 0.9 × 100 × 0 = 0.0     ... (19)

TOTAL = 3.5 + 10.0 + 0.0 = 13.5     ... (20)

METS = 13.5 / 3.5 = 3.9     ... (21)

EXAMPLE)  METS VALUE FOR JOGGING AT SPEED OF 10 km/h

HORIZONTAL FACTOR H = 0.2 × 166.7 = 33.34     ... (22)
    VERTICAL FACTOR V = 0.9 × 166.7 × 0 = 0.0     ... (23)

TOTAL = 3.5 + 33.34 = 36.84     ... (24)

METS = 36.84 / 3.5 = 10.5     ... (25)

FIG. 13

EXAMPLE) 60-kg PERSON RUNNING ON FLAT PATH AT SPEED OF 10 km/h (166.7 m/min) FOR 30 MINUTES $$(3.5 + 166.7 \times 0.2) / 3.5 \times 60 \times 30 / 60 = 315.77 \text{ kcal} \quad \ldots (26)$$

FIG. 14

FORMULA (METS APPLIED TO CALCULATE ENERGY CONSUMED)

SPEED AT ONE EXERCISE $V_i$ = STRIDE $W_w$ / TIME PER EXERCISE $T_i$ ... (27)

ENERGY CONSUMED = SUM (WEIGHT (kg) × METS VALUE DETERMINED FROM ONE EXERCISE AT SPEED Vi METS (Vi) × TIME FOR ONE EXERCISE Ti) ... (28)

$= \Sigma \text{WEIGHT} \times \text{METS}(V_i) \times T_i$ ... (29)

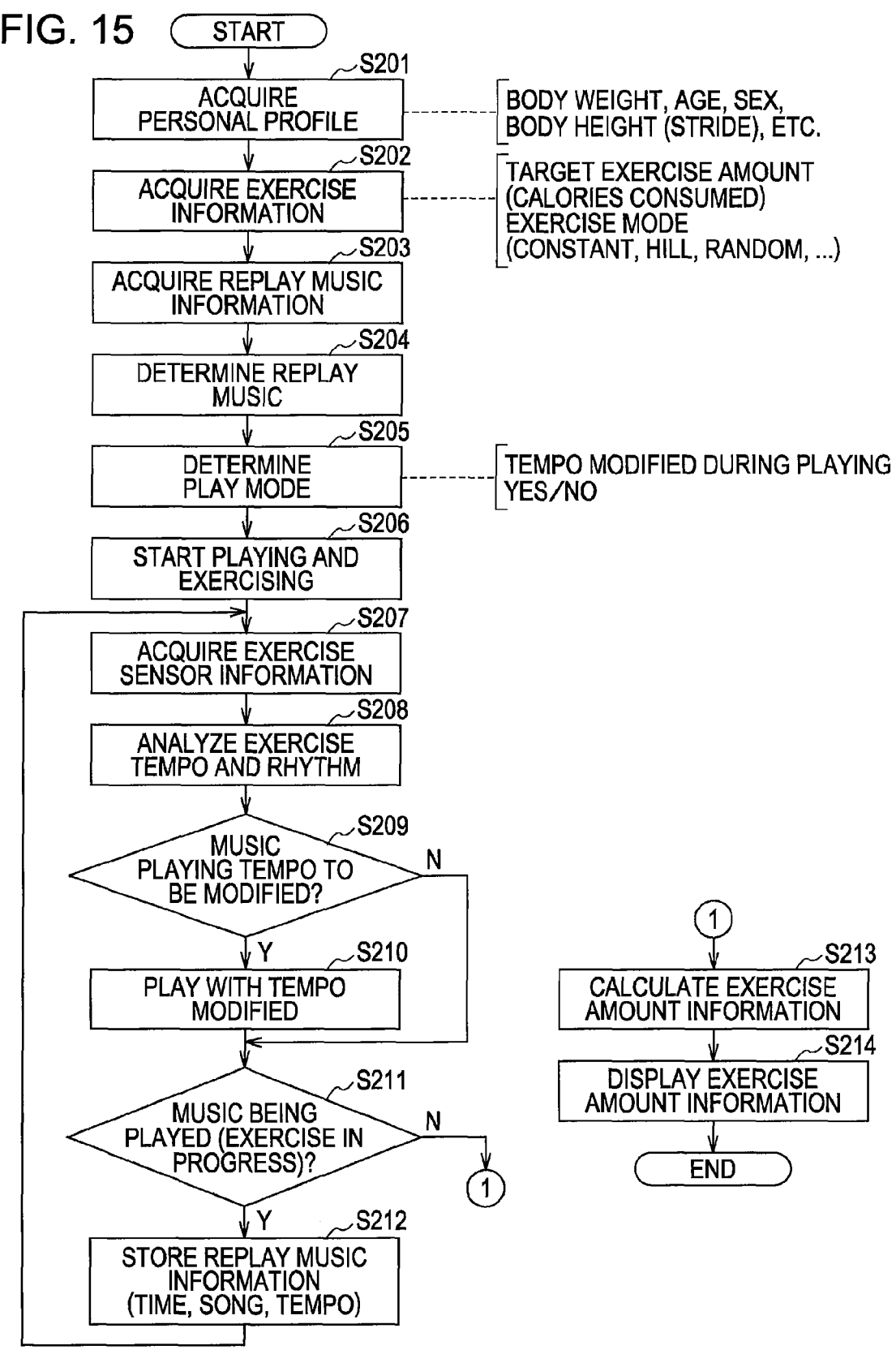

EXERCISE AMOUNT INFORMATION

| | |
|---|---|
| EXERCISE TIME | 30:00 minutes |
| NUMBER OF STEPS | 10000 steps |
| DISTANCE WALKED | 3.00 km |
| AVERAGE SPEED | 6.00 km/h |
| CALORIES CONSUMED | 150 kcal |
| FAT BURNED | 20 g |

GOOD EXERCISE!

FIG. 18
REPLAY MUSIC INFORMATION

| TITLE | LENGTH | SONG TEMPO | ENERGY CONSUMED |
|---|---|---|---|
| SONG A | 1:11 | 100 | 10 kcal |
| SONG B | 2:22 | 120 | 25 kcal |
| SONG C | 3:33 | 105 | 30 kcal |
| SONG D | 2:30 | 145 | 35 kcal |
| SONG E | 1:50 | 180 | 30 kcal |
| SONG F | 3:00 | 80 | 15 kcal |

FIG. 19A
REPLAY MUSIC LIST 1 (CONSTANT PACE)

| TITLE | LENGTH | SONG TEMPO | NO. OF PLAYS |
|---|---|---|---|
| SONG A | 1:11 | 100 | 50 (500 kcal) |

FIG. 19B
REPLAY MUSIC LIST 2 (RISING AND FALLING)

| TITLE | LENGTH | SONG TEMPO | NO. OF PLAYS |
|---|---|---|---|
| SONG A | 1:11 | 100 | 5 (50 kcal) |
| SONG C | 3:33 | 105 | 1 (30 kcal) |
| SONG B | 2:22 | 120 | 1 (25 kcal) |
| SONG D | 2:30 | 145 | 1 (35 kcal) |
| SONG E | 1:50 | 180 | 8 (240 kcal) |
| SONG B | 2:22 | 120 | 3 (75 kcal) |
| SONG C | 3:33 | 105 | 1 (30 kcal) |
| SONG F | 3:00 | 80 | 1 (15 kcal) |

~34G

EXERCISE AMOUNT INFORMATION

| | |
|---|---|
| TARGET CALORIES CONSUMED | 500 kcal |
| EXERCISE TIME | 30:00 minutes |
| DISTANCE WALKED | 3.00 km |
| AVERAGE SPEED | 6.00 km/h |
| FAT BURNED | 20 g |

GOOD EXERCISE!

EXERCISE INFORMATION PLOTTED IN GRAPH (EXAMPLE)

REPLAY MUSIC INFORMATION

| TITLE | LENGTH | SONG TEMPO (BPM) |
|---|---|---|
| SONG A | 1:11 | 100 |
| SONG B | 2:22 | 120 |
| SONG C | 3:33 | 105 |
| SONG D | 2:30 | 145 |
| SONG E | 1:50 | 180 |
| SONG F | 3:00 | 80 |
| SONG G | 2:00 | 100 |
| SONG H | 3:30 | 130 |
| SONG I | 2:00 | 100 |

REPLAY MUSIC LIST 1 (HILL MODE)
AUTOMATIC MUSIC SELECTION

| TITLE | LENGTH | SONG TEMPO | NO. OF PLAYS |
|---|---|---|---|
| SONG A | 1:11 | 100 | 5 |
| SONG C | 3:33 | 105 | 1 |
| SONG B | 2:22 | 120 | 1 |
| SONG D | 2:30 | 145 | 1 |
| SONG E | 1:50 | 180 | 30 |
| SONG B | 2:22 | 120 | 2 |
| SONG C | 3:33 | 105 | 1 |
| SONG F | 3:00 | 80 | 1 |

HILL MODE

FIG. 25A  REPLAY MUSIC LIST 2 (CONSTANT MODE) AUTOMATIC MUSIC SELECTION

| TITLE | LENGTH | SONG TEMPO | NO. OF PLAYS |
|---|---|---|---|
| SONG A | 1:11 | 100 | 50 |

CONSTANT MODE

FIG. 26A  REPLAY MUSIC LIST 3 (RANDOM MODE) AUTOMATIC MUSIC SELECTION

| TITLE | LENGTH | SONG TEMPO | NO. OF PLAYS |
|---|---|---|---|
| SONG A | 1:11 | 100 | 5 |
| SONG E | 1:50 | 180 | 5 |
| SONG C | 3:33 | 105 | 3 |
| SONG E | 1:50 | 180 | 10 |
| SONG B | 2:22 | 120 | 5 |
| SONG F | 3:00 | 80 | 1 |

RANDOM MODE

FIG. 27A

PRESET REPLAY MUSIC LIST 1
(WALKING OF 30 MINUTES)

| TITLE | LENGTH | SONG TEMPO | NO. OF PLAYS |
|---|---|---|---|
| SONG A | 1:11 | 100 | 2 |
| SONG B | 2:22 | 120 | 3 |
| SONG C | 3:33 | 105 | 3 |
| SONG G | 2:00 | 100 | 3 |
| SONG I | 2:00 | 100 | 2 |

FIG. 27B

PRESET REPLAY MUSIC LIST 2
(JOGGING OF 30 MINUTES)

| TITLE | LENGTH | SONG TEMPO | NO. OF PLAYS |
|---|---|---|---|
| SONG B | 2:22 | 120 | 2 |
| SONG D | 2:30 | 145 | 2 |
| SONG E | 1:50 | 180 | 2 |
| SONG D | 2:30 | 145 | 2 |
| SONG H | 3:30 | 130 | 2 |
| SONG B | 2:22 | 120 | 2 |

REPLAY MUSIC CANDIDATE LIST

LIST 1 (HILL MODE)

| TITLE | LENGTH | SONG TEMPO | NO. OF PLAYS |
| :---: | :---: | :---: | :---: |
| ⋮ | ⋮ | ⋮ | ⋮ |

LIST 2 (CONSTANT MODE)

| TITLE | LENGTH | SONG TEMPO | NO. OF PLAYS |
| :---: | :---: | :---: | :---: |
| ⋮ | ⋮ | ⋮ | ⋮ |

LIST 3 (RANDOM MODE)

REPLAY MUSIC CANDIDATE LIST

1. LIST 1 (HILL MODE)
2. LIST 2 (CONSTANT MODE)
3. LIST 3 (RANDOM MODE)
4. PRESET LIST 1 (WALKING OF 30 MINUTES)
5. PRESET LIST 2 (JOGGING OF 30 MINUTES)

FIG. 29

A  REPLAY MUSIC LIST 3
(RANDOM MODE)

| TITLE | LENGTH | SONG TEMPO | NO. OF PLAYS |
|---|---|---|---|
| SONG A | 1:11 | 100 | 5 |
| SONG E | 1:50 | 180 | 5 |
| SONG G | 2:00 | 100 | 3 |
| SONG E | 1:50 | 180 | 10 |
| SONG B | 2:22 | 120 | 5 |
| SONG F | 3:00 | 80 | 1 |

B  MODIFIED REPLAY MUSIC LIST 3
(RANDOM MODE)

| TITLE | LENGTH | SONG TEMPO | NO. OF PLAYS |
|---|---|---|---|
| SONG A | 1:11 | 100 | 5 |
| SONG E | 1:50 | 180 | 5 |
| SONG I | 2:00 | 100 | 3 |
| SONG E | 1:50 | 180 | 10 |
| SONG B | 2:22 | 120 | 5 |
| SONG F | 3:00 | 80 | 1 |

C  MODIFIED REPLAY MUSIC LIST 3
(RANDOM MODE)

| TITLE | LENGTH | SONG TEMPO | NO. OF PLAYS |
|---|---|---|---|
| SONG F | 3:00 | 80 | 2 |
| SONG E | 1:50 | 180 | 5 |
| SONG I | 2:00 | 100 | 3 |
| SONG E | 1:50 | 180 | 10 |
| SONG A | 1:11 | 100 | 10 |
| SONG F | 3:00 | 80 | 1 |

REPLAY MUSIC INFORMATION

| TITLE | LENGTH | SONG TEMPO (BPM) | ENERGY CONSUMED |
|---|---|---|---|
| SONG A | 1:11 | 100 | 10 kcal |
| SONG B | 2:22 | 120 | 25 kcal |
| SONG C | 3:33 | 105 | 30 kcal |
| SONG D | 2:30 | 145 | 35 kcal |
| SONG E | 1:50 | 180 | 30 kcal |
| SONG F | 3:00 | 80 | 15 kcal |
| SONG G | 2:00 | 100 | 20 kcal |
| SONG H | 3:30 | 130 | 30 kcal |
| SONG I | 2:00 | 100 | 20 kcal |

REPLAY MUSIC LIST 1 (HILL MODE)   500 kcal

| TITLE | LENGTH | SONG TEMPO | NO. OF PLAYS |
|---|---|---|---|
| SONG A | 1:11 | 100 | 5 (50 kcal) |
| SONG C | 3:33 | 105 | 1 (30 kcal) |
| SONG B | 2:22 | 120 | 1 (25 kcal) |
| SONG D | 2:30 | 145 | 1 (35 kcal) |
| SONG E | 1:50 | 180 | 8 (240 kcal) |
| SONG B | 2:22 | 120 | 3 (75 kcal) |
| SONG C | 3:33 | 105 | 1 (30 kcal) |
| SONG F | 3:00 | 80 | 1 (15 kcal) |

HILL MODE

FIG. 33A  REPLAY MUSIC LIST 2 (CONSTANT MODE)   500 kcal

| TITLE | LENGTH | SONG TEMPO | NO. OF PLAYS |
|---|---|---|---|
| SONG A | 1:11 | 100 | 50 (500 kcal) |

CONSTANT MODE

FIG. 34A  REPLAY MUSIC LIST 3 (RANDOM MODE)   500 kcal

| TITLE | LENGTH | SONG TEMPO | NO. OF PLAYS |
|---|---|---|---|
| SONG A | 1:11 | 100 | 3 (30 kcal) |
| SONG E | 1:50 | 180 | 3 (90 kcal) |
| SONG C | 3:33 | 105 | 3 (90 kcal) |
| SONG E | 1:50 | 180 | 5 (150 kcal) |
| SONG B | 2:22 | 120 | 5 (125 kcal) |
| SONG F | 3:00 | 80 | 1 (15 kcal) |

RANDOM MODE

REPLAY MUSIC LIST 4
(COMPLEX MODE)                     500 kcal

| TITLE | LENGTH | SONG TEMPO | NO. OF PLAYS |
|-------|--------|------------|--------------|
| SONG B | 2:22 | 120 | 5 (125 kcal) |
| SONG E | 1:50 | 180 | 10 (300 kcal) |
| SONG F | 3:00 | 80 | 5 (75 kcal) |

COMPLEX MODE
(LOW LOAD → HIGH LOAD → COOL-DOWN)

PRESET REPLAY MUSIC LIST 1
(RANDOM 500 kcal)

| TITLE | LENGTH | SONG TEMPO | NO. OF PLAYS |
|-------|--------|------------|--------------|
| SONG A | 1:11 | 100 | 5 (50 kcal) |
| SONG E | 1:50 | 180 | 2 (60 kcal) |
| SONG C | 3:33 | 105 | 3 (90 kcal) |
| SONG E | 1:50 | 180 | 7 (210 kcal) |
| SONG B | 2:22 | 120 | 3 (75 kcal) |
| SONG F | 3:00 | 80 | 1 (15 kcal) |

FIG. 37

A  REPLAY MUSIC LIST 3 (RANDOM MODE)

| TITLE | LENGTH | SONG TEMPO | NO. OF PLAYS |
|---|---|---|---|
| SONG A | 1:11 | 100 | 3 (30 kcal) |
| SONG E | 1:50 | 180 | 3 (90 kcal) |
| SONG C | 3:33 | 105 | 3 (90 kcal) |
| SONG E | 1:50 | 180 | 5 (150 kcal) |
| SONG B | 2:22 | 120 | 5 (125 kcal) |
| SONG F | 3:00 | 80 | 1 (15 kcal) |

B  MODIFIED REPLAY MUSIC LIST 3 (RANDOM MODE)

| TITLE | LENGTH | SONG TEMPO | NO. OF PLAYS |
|---|---|---|---|
| SONG A | 1:11 | 100 | 3 (30 kcal) |
| SONG E | 1:50 | 180 | 3 (90 kcal) |
| SONG H | 3:33 | 130 | 3 (90 kcal) |
| SONG E | 1:50 | 180 | 5 (150 kcal) |
| SONG B | 2:22 | 120 | 5 (125 kcal) |
| SONG F | 3:00 | 80 | 1 (15 kcal) |

FIG. 38

EXERCISE INFORMATION DISPLAY EXAMPLE  ~34G

```
EXERCISE AMOUNT INFORMATION

TARGET CALORIES CONSUMED      500 kcal
EXERCISE TIME                 30:00 minutes
DISTANCE WALKED               3.00 km
AVERAGE SPEED                 6.00 km/h
CALORIES CONSUMED             150 kcal
FAT BURNED                    19.5 g

GOOD EXERCISE!
```

FIG. 42A

INPUT YOUR PROFILE

YOUR NAME [          ]
SEX [       ]
AGE [       ] years old
HEIGHT [       ] cm
WEIGHT [       ] kg

| YOUR NAME | ○○○ |
| SEX | Man |
| AGE | 30 years old |
| HEIGHT | 170 cm |
| WEIGHT | 60 kg |
| BMI | 20.8 |
| DEGREE OF OBESITY | 1 |

ALL INPUT DATA CORRECT? [YES] [NO]

EXERCISE YOU ARE PLANNING

TYPE

EXERCISE MODE

AVERAGE SPEED

TIME

| EXERCISE TYPE | WALKING |
| --- | --- |
| EXERCISE MODE | CONSTANT |
| AVERAGE SPEED | 5 km/h |
| TIME | 30 MINUTES |

ARE YOU SURE?  YES  NO

INPUT EXERCISE YOU ARE PLANNING

TYPE

EXERCISE MODE

AVERAGE SPEED

TARGET EXERCISE AMOUNT

| EXERCISE TYPE | WALKING |
| --- | --- |
| EXERCISE MODE | CONSTANT |
| AVERAGE SPEED | 5 km/h |
| TARGET EXERCISE AMOUNT | 500 kcal |

ARE YOU SURE?  YES  NO

~34G

SELECTION WINDOW DISPLAY EXAMPLE FOR EXERCISE TYPE

MODE SELECTION WINDOW DISPLAY EXAMPLE

FIG. 48

REPLAY MUSIC INFORMATION
(DRIVEN BY PROFILE, ETC.)

| TITLE | LENGTH | SONG TEMPO (BPM) |
|---|---|---|
| SONG A | 1:11 | 100 |
| SONG B | 2:22 | 120 |
| SONG C | 3:33 | 105 |
| SONG D | 2:30 | 145 |
| SONG E | 1:50 | 180 |
| SONG F | 3:00 | 80 |
| SONG G | 2:00 | 100 |
| SONG H | 3:30 | 130 |
| SONG I | 2:00 | 100 |

FIG. 49

REPLAY MUSIC INFORMATION
(DRIVEN BY TARGET EXERCISE AMOUNT)

| TITLE | LENGTH | SONG TEMPO (BPM) | ENERGY CONSUMED |
|---|---|---|---|
| SONG A | 1:11 | 100 | 10 kcal |
| SONG B | 2:22 | 120 | 25 kcal |
| SONG C | 3:33 | 105 | 30 kcal |
| SONG D | 2:30 | 145 | 35 kcal |
| SONG E | 1:50 | 180 | 30 kcal |
| SONG F | 3:00 | 80 | 30 kcal |
| SONG G | 2:00 | 100 | 20 kcal |
| SONG H | 3:30 | 130 | 30 kcal |
| SONG I | 2:00 | 100 | 20 kcal |

FIG. 50C

REPLAY MUSIC LIST 1
(HILL MODE)

| TITLE | LENGTH | SONG TEMPO | NO. OF PLAYS |
|---|---|---|---|
| SONG A | 1:11 | 100 | 5 |
| SONG C | 3:33 | 105 | 1 |
| SONG B | 2:22 | 120 | 1 |
| SONG D | 2:30 | 145 | 1 |
| SONG E | 1:50 | 180 | 30 |
| SONG B | 2:22 | 120 | 2 |
| SONG C | 3:33 | 105 | 1 |
| SONG F | 3:00 | 80 | 1 |

PRESET PLAY LIST IS AVAILABLE FOR USE

DO YOU USE?   | YES | NO |

PLAY LIST FOR WALKING OF 30 MINUTES

| TITLE | LENGTH | SONG TEMPO | NO. OF PLAYS |
|---|---|---|---|
| SONG A | 1:11 | 100 | 5 |
| SONG E | 1:50 | 180 | 5 |
| SONG C | 3:33 | 105 | 3 |
| SONG E | 1:50 | 180 | 10 |
| SONG B | 2:22 | 120 | 5 |
| SONG F | 3:00 | 80 | 1 |

REPLAY MUSIC LIST 1 (HILL MODE)

| TITLE | LENGTH | SONG TEMPO | NO. OF PLAYS |
|---|---|---|---|
| SONG A | 1:11 | 100 | 5 |
| SONG C | 3:33 | 105 | 1 |
| SONG B | 2:22 | 120 | 1 |
| SONG D | 2:30 | 145 | 1 |
| SONG E | 1:50 | 180 | 30 |
| SONG B | 2:22 | 120 | 2 |
| SONG C | 3:33 | 105 | 1 |
| SONG F | 3:00 | 80 | 1 |

| TITLE | LENGTH | SONG TEMPO | NO. OF PLAYS |
|---|---|---|---|
| SONG A | 1:11 | 100 | 50 |

REPLAY MUSIC LIST 2 (CONSTANT MODE)

REPLAY MUSIC LIST 3 (RANDOM MODE)

| TITLE | LENGTH | SONG TEMPO | NO. OF PLAYS |
|---|---|---|---|
| SONG A | 1:11 | 100 | 5 |
| SONG E | 1:50 | 180 | 5 |
| SONG C | 3:33 | 105 | 3 |
| SONG E | 1:50 | 180 | 10 |
| SONG B | 2:22 | 120 | 5 |
| SONG F | 3:00 | 80 | 1 |

| TITLE | LENGTH | SONG TEMPO | NO. OF PLAYS |
|---|---|---|---|
| SONG B | 2:22 | 120 | 5 |
| SONG E | 1:50 | 180 | 5 |
| SONG F | 3:00 | 80 | 5 |

REPLAY MUSIC LIST 4 (COMPLEX MODE)

MODIFYING SELECTED PLAY LIST

DO YOU MODIFY?  YES  NO

REPLAY MUSIC LIST 3
(RANDOM MODE)

| TITLE | LENGTH | SONG TEMPO | NO. OF PLAYS |
|---|---|---|---|
| SONG A | 1:11 | 100 | 5 |
| SONG E | 1:50 | 180 | 5 |
| SONG G | 2:00 | 100 | 3 |
| SONG E | 1:50 | 180 | 10 |
| SONG B | 2:22 | 120 | 5 |
| SONG F | 3:00 | 80 | 1 |

MODIFIED REPLAY MUSIC LIST 3
(RANDOM MODE)

| TITLE | LENGTH | SONG TEMPO | NO. OF PLAYS |
|---|---|---|---|
| SONG A | 1:11 | 100 | 5 |
| SONG E | 1:50 | 180 | 5 |
| SONG I | 2:00 | 100 | 3 |
| SONG E | 1:50 | 180 | 10 |
| SONG B | 2:22 | 120 | 5 |
| SONG F | 3:00 | 80 | 1 |

34G

| TITLE | LENGTH | SONG TEMPO | NO. OF PLAYS |
|---|---|---|---|
| SONG A | 1:11 | 100 | 5 (50 kcal) |
| SONG C | 3:33 | 105 | 1 (30 kcal) |
| SONG B | 2:22 | 120 | 1 (25 kcal) |
| SONG D | 2:30 | 145 | 1 (35 kcal) |
| SONG E | 1:50 | 180 | 8 (240 kcal) |
| SONG B | 2:22 | 120 | 3 (75 kcal) |
| SONG C | 3:33 | 105 | 1 (30 kcal) |
| SONG F | 3:00 | 80 | 1 (15 kcal) |

REPLAY MUSIC LIST 1 (HILL MODE)

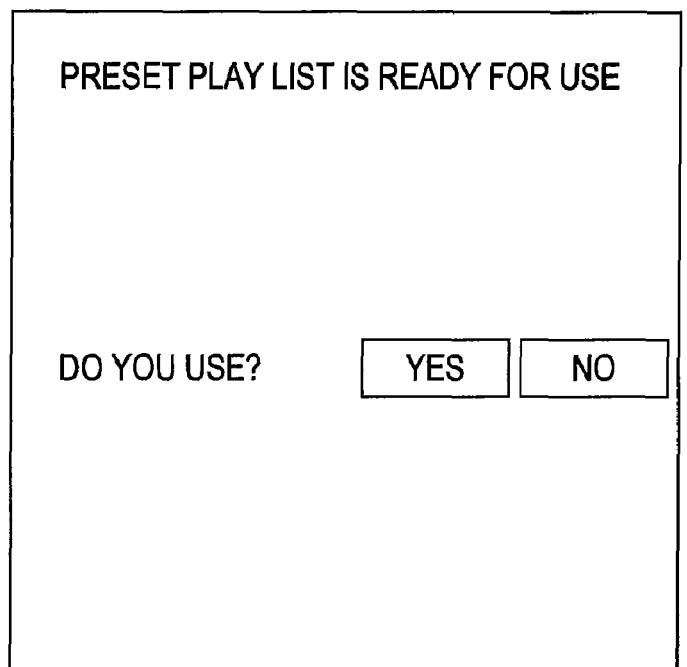

FIG. 59C

MODIFIED REPLAY MUSIC LIST 3
(RANDOM MODE)

| TITLE | LENGTH | SONG TEMPO | NO. OF PLAYS |
|---|---|---|---|
| SONG A | 1:11 | 100 | 3 (30 kcal) |
| SONG E | 1:50 | 180 | 3 (90 kcal) |
| SONG H | 3:30 | 130 | 3 (90 kcal) |
| SONG E | 1:50 | 180 | 5 (150 kcal) |
| SONG B | 2:22 | 120 | 5 (125 kcal) |
| SONG F | 3:00 | 80 | 1 (15 kcal) |

SONG C IS GOING TO BE REPLACED WITH SONG H

ARE YOU SURE?   YES   NO

34G

FIG. 61
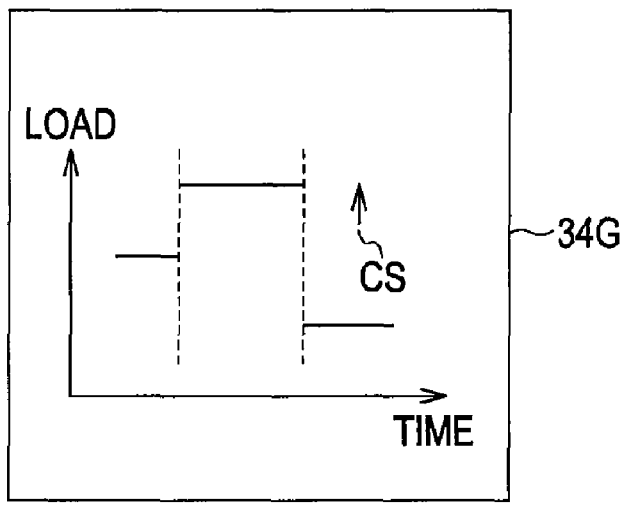
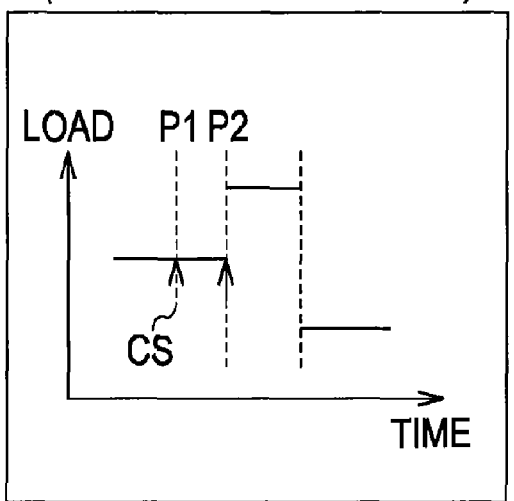
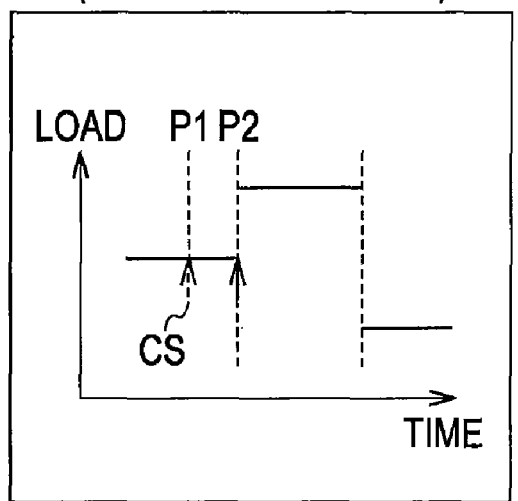

AUDIO REPRODUCING APPARATUS, AUDIO REPRODUCING METHOD, AND AUDIO REPRODUCING PROCESSING PROGRAM

CROSS REFERENCE TO RELATED APPLICATIONS

The present application claims priority to Japanese Patent Application JP 2005-027654, filed on Feb. 3, 2005; Japanese Patent Application JP 2005-352948, filed on Dec. 7, 2005; and Japanese Patent Application JP 2005-352949, filed on Dec. 7, 2005, the entire contents of which is being incorporated herein by reference.

BACKGROUND

The present disclosure relates to a method and a program for use in an apparatus having a function of reproducing an audio sound, such as a hard disk player, a MD (Mini Disc) player, or a mobile information terminal having music data reproducing function, or an apparatus for reproducing.

Under today's health conscious environment, more and more people play sports including aerobic exercise, such as jogging, walking, aerobics, etc. for the purpose of maintaining and improving health. To achieve effect, sports must be continually practiced for a substantial amount of time. To continue sports in pleasant fashion, some people play sports while listening to music. A reproducing apparatus for listening to music while playing sports has a function to motivate a person to play sports and assist the person to continue sports.

For example, a known apparatus provides an exercising rhythm in sports. Japanese Unexamined Patent Application Publication No. 55-012452 discloses a technique of running pace maker that provides a running pace by emitting a "beep" sound to a runner during a running exercise.

In accordance with Japanese Unexamined Patent Application Publication Nos. 06-130960 and 2003-177749, a detector mounted on the body of a user detects vibrations and steps in the exercise, determines exercise pace from defected data, and varies playing tempo of music in response to a variation in the exercise pace.

Japanese Unexamined Patent Application Publication No. 2001-299980 discloses an apparatus for promoting health and reducing weight. The apparatus includes an exercise sensor for detecting the tempo of an exercise and a tempo modification unit. The tempo of the music to be reproduced is modified based on a difference between the pulse rate of the user and a target pulse rate in order to guide the user to the target pulse rate.

Japanese Unexamined Patent Application Publication No. 2003-305146 discloses an apparatus for providing the user with information relating to an amount of exercise such as energy consumed. Music data stored in a server is supplied to a terminal carried by a user via a network. The user walks in step with the rhythm of music, and the apparatus presents the number of steps and the consumed energy based on the number of steps.

In accordance with Japanese Unexamined Patent Application Publication No. 2002-073018, instead of varying the tempo of music in step with the exercise tempo of the user, an apparatus stores, on a music database, music having tempos responsive to each phase of the exercise (such as warm-up phase, light exercise phase, hard exercise phase, cool-down phase), and selects and provides appropriately music. An apparatus disclosed in Japanese Unexamined Patent Application Publication No. 2002-301050 measures bio-information of the user, adjusts the output of home electronics in response to the measurement results, and guides the user to a target exercise amount.

A variety of apparatuses for allowing the user to continue comfortably and effectively jogging, walking, aerobics draw high public attention. Accordingly, a variety of apparatuses have been proposed and are currently in actual use.

The techniques disclosed in Japanese Unexamined Patent Application Publications Nos. 55-012452, 06-130960, 2003-177749, 2001-299980, 2003-305146, 2002-073018, and 2002-301050 have characteristics thereof, and are effective. The techniques disclosed in Japanese Unexamined Patent Application Publications Nos. 55-012452, 06-130960, 2003-177749, 2001-299980, 2003-305146, 2002-073018, and 2002-301050 satisfy users in one application area but do not in other application areas.

For example, in accordance with the technique disclosed in Japanese Unexamined Patent Application Publication No. 55-012452, the pace making sound emitted to maintain the running pace is a dry electronic sound such as "beep, beep." The user can be tired of and unable to keep pace with before reaching a steady-state exercise phase. A discrepancy can take place between the exercise pace of the user and the pace making sound. The user can feel discordant mid uncomfortable, and cannot enjoy continuously exercise.

Using one of the techniques disclosed in Japanese Unexamined Patent Application Publications Nos. 06-130960 and 2003-177749, music may be used instead of the electronic sound "beep" and play tempos may be varied in step with the exercise pace in order to enjoy continuously exercise. In accordance with the techniques disclosed in Japanese Unexamined Patent Application Publications Nos. 06-130960 and 2003-177749, exercise can be comfortably continued for a long period of time, but no sufficient consideration is given to the health promoting effect, weight control effect, and management of the exercise amount. Exercise information is not properly fed to a user. For example, how a target exercise needs to be practiced to promote health and reduce weight and an amount of exercise practiced by the user are not fed back to the user.

In accordance with the techniques disclosed in Japanese Unexamined Patent Application Publications Nos. 2001-299980, 2003-305146, 2002-073018, and 2002-301050, an apparatus including in addition to an exercise sensor a detector for detecting bio signs such as pulse rate is provided, and an amount of exercise is calculated from reproduced music data, and provided. The use of a plurality of sensors makes the entire system complex. The system incorporating a variety of functions leads to a large-scale and high-cost design. The system becomes complex in operation, thereby inconveniencing the user. Sufficient consideration needs to be given to the management of personal information from the standpoint of managing the personal information of individuals in exercise activity.

It is desirable to assist a user in the continued practice of aerobic exercise such as jogging, walking, or aerobics often difficult to continue. It is desirable to present a motivation for exercise to the user in a clear fashion and help the user to continue exercise. It is also desirable to provide an easy-to-use and exercise-assisting apparatus that appropriately manages the exercise amount.

It is further desirable to provide an apparatus, a method, and a program for assisting a user in exercise in a manner free from the above-described problems, and to provide an easy-to-use apparatus, and a method and a program for embodying the apparatus.

SUMMARY

In an embodiment, an audio reproducing apparatus is provided and includes reproducing means for reproducing music data, receiving means for receiving information input by a user, acquisition means for acquiring characteristic information relating to the music data, calculating means for calculating an amount of exercise of the user who exercises in response to music into which the reproducing means reproduces the music data based on the characteristic information of the music data reproduced by the reproducing means, the characteristic information being acquired by the acquisition means, and personal profile information relating to the body of the user received by the receiving means, and output means for outputting as exercise amount information the amount of exercise calculated by the calculating means.

The audio reproducing apparatus allows the user to walk or jog in step with the tempo of the music being reproduced while listening to the music responsive to the music data reproduced by the reproducing means.

At the start of the exercise, the personal profile information relating to the body of the user received by the receiving means, such as the body weight, the body height, the age and the sex of the user, and the characteristic information of the music data acquired by the acquisition means, such as play time and tempo, are used. The calculating means calculates the amount of exercise of the user who exercises in response to the reproduced music, and the calculated amount of exercise is indicated to the user via the output means.

When exercising in synchronization with the reproduced music, the user can learn the amount of exercise practiced by himself or herself in a manner free from any complex operation. The user can continue freely exercise in synchronization with the music. The user can learn objectively the amount of exercise performed. The user can know how he or she must exercise to achieve what level of exercise, and can motivate him or her clearly to continue exercise.

Since the amount of exercise of the user is calculated from the characteristic information of the audio data reproduced and the personal profile information, a new device to calculate the amount of exercise of the user is not required. This prevents the apparatus from becoming bulky and complex in structure.

In an embodiment, the audio reproducing apparatus includes determining means for selecting and determining the music data to be reproduced, based on the personal profile information and the characteristic information of the music data acquired by the acquisition means when the personal profile information is received by the receiving means.

The audio reproducing apparatus includes the determining means selects and determines the music data to be reproduced, based on the personal profile information and the characteristic information of the music data when the personal profile information is received by the receiving means.

With this arrangement, the user simply exercises in synchronization with the music into which the music data determined by the determining means is reproduced. The apparatus thus guides the user by the reproduced music so that the user may continue comfortably a predetermined amount of exercise.

In an embodiment, the audio reproducing apparatus includes determining means for selecting and determining the music data to be reproduced, based on target exercise amount information and the characteristic information of the music data acquired by the acquisition means when the target exercise amount information is received by the receiving means.

The audio reproducing apparatus, in an embodiment, receives the target exercise amount information of the user via the receiving means. The target exercise amount information is information such as the calories consumed (heat energy consumed by exercising). The determining means automatically selects and determines the music data to be reproduced based on the target exercise amount information and the characteristic, information of the replayable music data in order for the user to exercise to achieve the target exercise amount.

The user can consume target calories by simply exercising in synchronization with music into which the audio data determined by the determining means is reproduced. In other words, the audio reproducing apparatus guides the user by means of the reproduced music so that the user comfortably continues to play exercise of the amount targeted by the user.

The audio reproducing apparatus, in an embodiment, includes indicating means for indicating a replay music list indicative of the order of reproducing music data of at least one song, and the number of plays of each of the music data of at least one song, and selection input receiving means for receiving a selection input of a target replay music list selected from among replay music lists indicated by the indicating means, wherein the reproducing means reproduces the music data in accordance with the replay music list selected by the selection input receiving means.

The audio reproducing apparatus, in an embodiment, indicates the replay music list to the user using the indicating means, and selects the target replay music list (the one to be actually used) from the replay music lists indicated by the selection input receiving means. The music data is thus reproduced in accordance with the selected music list.

The music data is reproduced in accordance with the replay music list selected by the user. The user can thus continuously comfortably play the target exercise and appropriately feed back the amount of exercised by the user by simply selecting the target replay music list and exercising in synchronization with the reproduced music. The user can monitor the amount of exercise in a simple and exact manner.

The audio reproducing apparatus, in an embodiment, includes content notification means for notifying of the content the replay music list selected by the selection input receiving means, modification input receiving means for receiving a modification input to the content of the music list notified of by the content notification means, and modifying means for modifying, in response to the modification input received by the modification input receiving means, the content of the replay music list selected by the selection input receiving means and notified of by the content, notification means, wherein the reproducing means reproduces the music data in accordance with the replay music list modified by the modifying means.

The audio reproducing apparatus, in an embodiment, notifies of the content of the selected replay music list using the content notification means and receives the modification input using the modification input receiving means. In response, the modifying means modifies the content of the selected replay music list. The reproducing means reproduces the music data in accordance with the modified music list.

In this way, the user can modify the content of the replay music list as appropriate. The music data is reproduced to the preference and intention of the user's. The user is thus guided to an effective exercise.

The audio reproducing apparatus, in an embodiment, includes storage means for storing history information relating to reproduced music data, the history information including at least one of identification information concerning the reproduced music data, the exercise amount information, and the personal profile information.

The audio reproducing apparatus, in an embodiment, stores on the storage means the history information including at least one of the identification information concerning the reproduced music data, the exercise amount information calculated by the calculating means, and the personal profile information received by the receiving means.

The user can learn how much music data has been reproduced when the identification information of the music data is stored. When the identification information is stored, the user can learn the total amount of exercise practiced up until now. When the personal profile information is stored, the user can learn the reason of a change in the body weight information, for example, of the personal profile information.

The audio reproducing apparatus can manage information regarding the user's own exercise based on the history information. The audio reproducing apparatus performs a variety of analyses based on a variety of history information stored, thereby supplying the user with the analysis results.

An audio reproducing apparatus, in an embodiment, includes first display means for displaying on a display element an input window for personal profile information relating to the body of a user, first receiving means for receiving the personal profile information on the input window displayed by the first display means, second display means for displaying on the display element a selection window for selecting a replay music list to be used, from among at least one replay music list indicative of the order of reproducing music data of at least one song, and the number of plays of each of the music data of at least one song, second receiving means for receiving a selection input to the selection window displayed by the second display means, reproducing control means for controlling reproduction of the music data in accordance with the replay music list selected by the second receiving means, characteristic information storage means for storing characteristic information relating to usable music data, calculating means for calculating an amount of exercise of the user who exercises in response to reproduced music data, based on the personal profile information received by the first receiving means and the characteristic information of the reproduced music data stored on the characteristic information storage means, and notification means for notifying of the amount of exercise calculated by the calculating means.

The audio reproducing apparatus, in an embodiment, receives the personal profile information via the first display means and the first receiving means, selects the replay music list to be used, via the second display means and the second receiving means, and reproduces the music data with the reproducing control means in accordance with the selected replay music list.

The user exercises in synchronization with the music into which the music data is reproduced based on the characteristic information of the reproduced music data and the received personal profile information. The amount of exercise practiced by the user is calculated by the calculating means, and then the notification means notifies the user of the calculation results.

The screen responsive to the received information is displayed so that a variety of target information is received. The user can input a variety of information simply and exactly. User-friendliness is thus achieved. The user is guided to exercise in response to the reproduced music and notified of the amount of exercise practiced by the user. The user is motivated to exercise continuously and comfortably. The user can thus enjoy exercising.

The audio reproducing apparatus, in an embodiment, includes third display means for displaying on the display element a selection window for receiving a selection of a generation mode of the replay music list, third receiving means for receiving a selection input to the selection window displayed by the third display means, fourth display means for displaying on the display element an input window for receiving the input of a target exercise amount when the mode for generating the replay music list based on the target exercise amount is selected by the third receiving means, fourth receiving means for receiving the input of the target exercise amount to the input window displayed by the fourth display means, fifth display means for displaying on the display element an input window for receiving an input of a type of exercise when a mode other than the mode for generating the replay music list based on the target exercise amount is selected by the third receiving means, fifth receiving means for receiving the input of the type of the exercise to the input window displayed by the fourth display means, first list generating means for generating the replay music list in response to the personal profile information received by the first receiving means and the target exercise amount received by the fourth receiving means when the mode for generating the replay music list based on the target exercise amount is selected by the third receiving means, and second list generating means for generating the replay music list in response to the personal profile information received by the first receiving means and the type of the exercise received by the fifth receiving means when the mode other than the mode for generating the replay music list based on the target exercise amount is selected by the third receiving means, wherein the second display means displays the replay music list generated by the first list generating means and the replay music list generated by the second list generating means.

The audio reproducing apparatus, in an embodiment, receives the generation mode of the replay music list via the third display means and the third input means, receives required information such as the target exercise amount and the type of exercise in accordance with the received generation mode, generates the replay music list using the first list generating means or the second list generating means, and supplies the generated replay music list as being selectable.

Without the need for the user to select each piece of music data and produce a replay music list, an automatically generated replay music list is used as a replay music list responsive to the exercise intended by the user. Music for use by the user for efficient exercise is thus selected and reproduced without any particular complex operation.

The audio reproducing apparatus, in an embodiment, includes sixth display means for displaying on the display element the content of the replay music list selected by the second receiving means, and sixth receiving means for receiving a modification input to the content of the replay music list displayed by the sixth display means, wherein the reproducing control means controls reproduction of the music data in accordance with the replay music list selected by the second receiving means and modified by the sixth receiving means.

The audio reproducing apparatus of claim 30 modifies the content of the previously selected replay music list with the sixth display means and the sixth receiving means. Even an automatically generated replay music list may be modified to the usage or preference of the user.

In accordance with the present disclosure, the user can effectively exercise. In walking or jogging, the user is motivated to exercise continuously and comfortably. The audio reproducing apparatus helps the user to manage the amount of exercise of the user. Since the display prompts the user to operate the audio reproducing apparatus, an easy-to-use and user-friendly apparatus is provided.

Additional features and advantages are described herein, and will be apparent from, the following Detailed Description and the figure.

BRIEF DESCRIPTIONS OF THE FIGURES

FIG. 3 illustrates a list of replayable music data.

FIG. 4A illustrates an example of a replay music list as a list of the music data to be reproduced.

FIG. 4B illustrates an example of a replay music list as a list of the music data to be reproduced.

FIG. 5 illustrates an example of a display screen of exercise amount information.

FIG. 6 illustrates how a distance walked is calculated.

FIG. 7 illustrates how an average speed of a user during exercise is calculated.

FIG. 8 illustrates how an energy consumed is determined using an energy consumed per minute.

FIG. 9 illustrates how an energy consumed is determined using a METS value as an indicator indicating the intensity of exercise determined per exercise.

FIG. 10 illustrates how fat burned is determined.

FIG. 11 illustrates the METS value.

FIG. 12 illustrates the METS value.

FIG. 13 illustrates a specific example of determining calories consumed.

FIG. 14 illustrates a specific example of determining calories consumed.

FIG. 15 is a flowchart illustrating a process for generating and reproducing music data from a preset amount of exercise.

FIG. 16 illustrates one example of the display screen of exercise amount information.

FIG. 18 illustrates one example of the list of replayable music data.

FIG. 19A illustrates an example of a replay music list as a list of music data to be reproduced.

FIG. 19B illustrates an example of a replay music list as a list of music data to be reproduced.

FIG. 25A illustrates an example of a replay music list (constant mode) as a list of music data to be reproduced.

FIG. 26A illustrates an example of a replay music list (random mode) as a list of music data to be reproduced.

FIG. 27A illustrates a preset replay music list.

FIG. 27B illustrates a preset replay music list.

FIG. 28A illustrates an example of a replay music candidate list.

FIG. 28B illustrates an example of a replay music candidate list.

FIG. 29 illustrates a modification of the content of the replay music list.

FIG. 33A illustrates an automatically generated replay music list (constant mode).

FIG. 34A illustrates an automatically generated replay music list (random mode).

FIG. 37 illustrates a modification of the content of the replay music list.

FIG. 38 illustrates a display example of a calculated amount of exercise.

FIG. 42A illustrates an example of an input window and a verification window of the personal profile information.

FIG. 42B illustrates an example of the input window and the verification window of the personal profile information.

FIG. 44A illustrates an example of an input window and a verification window of exercise information.

FIG. 44B illustrates an example of the input window and the verification window of the exercise information.

FIG. 45A illustrates an example of the input window and the verification window of the exercise information.

FIG. 45B illustrates an example of the input window and the verification window of the exercise information.

FIG. 48 illustrates an example of replay music information.

FIG. 49 illustrates an example of the replay music information.

FIG. 50C illustrates an example of the display screen of the automatically generated replay music list.

FIG. 51A illustrates an example of a display screen of a preset replay music list.

FIG. 51B illustrates an example of the display screen of the preset replay music list.

FIG. 52 illustrates a display example of a replay music list (hill mode).

FIG. 53 illustrates a display example of a replay music list (constant mode).

FIG. 54 illustrates a display example, of a replay music list (random mode).

FIG. 55 illustrates a display example of a replay music list (complex mode).

FIG. 56A illustrates an example of a display screen used to modify a selected replay music list.

FIG. 56B illustrates an example of the display screen used to modify the selected replay music list.

FIG. 56C illustrates an example of the display screen used to modify the selected replay music list.

FIG. 58A illustrates an example of a display screen of a preset replay music list.

FIG. 58B illustrates an example of the display screen of the preset replay music list.

FIG. 59C illustrates an example of the display screen to modify the selected replay music list.

FIG. 59D illustrates an example of the display screen to modify the selected replay music list.

FIG. 61 illustrates a pattern modification of an exercise mode (complex mode).

DETAILED DESCRIPTION

An apparatus, a method and a program in accordance with embodiments are described below with reference to the drawings. In the embodiments discussed below, the apparatus, the method, and the program of the embodiments are applied to a mobile audio reproducing apparatus (music reproducing apparatus) such as a mobile hard disk player, a mobile MD (Mini Disc) player, or a cellular phone terminal having a playing function.

First Embodiment

Structure and Basic Operation of the Audio Reproducing Apparatus

Figure 1:
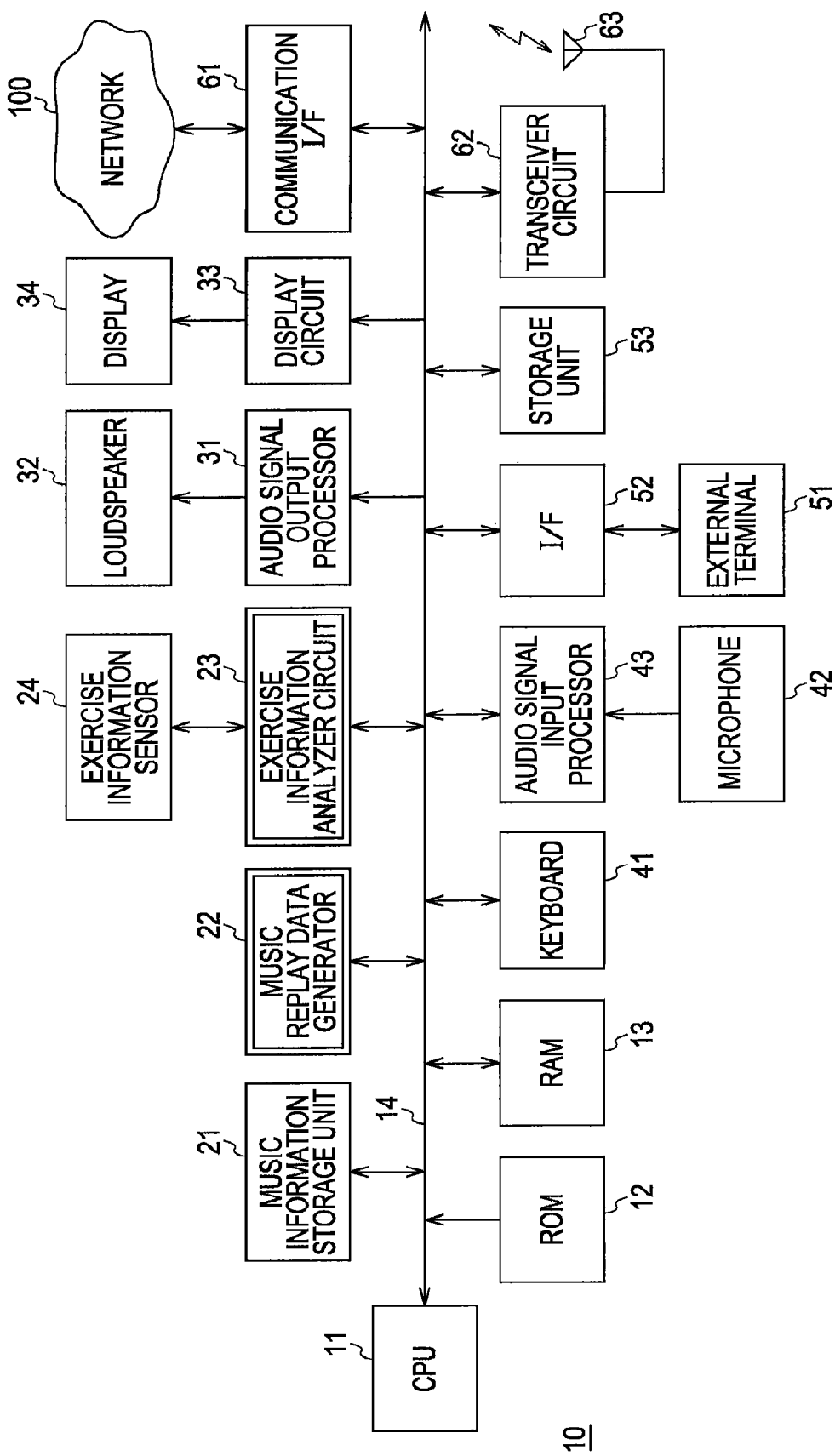
FIG. 1 is a block diagram illustrating an audio reproducing apparatus in accordance with one embodiment.

FIG. 1 is a block diagram illustrating the audio reproducing apparatus of a first embodiment. As described above, the audio reproducing apparatus of the first embodiment is mobile and has compact and lightweight design. The audio reproducing apparatus is comfortably carried by a user in a pocket of the user's clothes. The audio reproducing apparatus can thus be appropriately used by the user who wants to listen to music while walking or jogging.

As shown in FIG. 1, the audio reproducing apparatus of the first embodiment includes a controller 10, a music information storage unit 21, a music replay data generator 22, an exercise information analyzer circuit 23, an exercise information sensor 24, an audio signal output processor 31, a loudspeaker 32, a display circuit 33, a display 34, a keyboard 41, a microphone 42, an audio signal input processor 43, an external terminal 51, an I/F (interface) 52, a storage unit 53, a communication I/F 61, a transceiver circuit 62 and a transceiver antenna 63.

The controller 10 controls each section of the audio reproducing apparatus and includes a CPU (Central Processing Unit) 11, a ROM (Read Only Memory) 12, and a RAM (Random Access Memory) 13, connected to each other via a CPU bus 14. The CPU 11 executes a program and supplies control signals produced in response to the program to each element of the apparatus. The CPU 11 controls each element of the apparatus, thereby playing a major role in controlling the apparatus. The ROM 12 stores a variety of programs to be executed by the CPU 11 and a variety of data required for the CPU 11 to perform the processes. The RAM 13 temporarily stores provisional results of each process, thereby mainly serving as a work area.

The music information storage unit 21 reads music data stored on a recording medium, and writes music data on the recording medium. The recording medium is selected from a variety of recording media including a hard disk, a magneto-optical disk such as MD (Mini Disc), an optical disk such as a CD (Compact Disk) or DVD (Digital Versatile Disk), a semiconductor memory, an IC card memory composed of a semiconductor memory, and a magnetic tape. If the recording medium is a hard disk, the music information storage unit 21 is a hard disk drive, and if the recording medium is an optical disk, the music information storage unit 21 is an optical disk drive.

The music replay data generator 22 under the control of the controller 10 performs a variety of processes on the music data (song data) to be reproduced. As will described more in detail, the music replay data generator 22 performs processes, for example, selects music data to be reproduced, from among a plurality of pieces of music data stored on the music information storage unit 21, determines the play order of the music data to be reproduced, and adjusts play tempo of the music data to be reproduced.

The exercise information analyzer circuit 23 under the control of the controller 10 or the like performs an analysis process relating to exercise of a user. As will be described later, the exercise information analyzer circuit 23 calculates an amount of exercise based on personal profile information of the user, such as the body weight, the body height, and the sex of the user input via the keyboard 41, and characteristic information such as play time and tempo of the music data to be reproduced when the user practices a predetermined exercise in synchronization with music supplied during the playing of the music data.

When the amount of exercise as a target is input via the keyboard 41, the exercise information analyzer circuit 23 calculates the intensity of exercise and exercise time (throughout which the user continuously exercises) in response to the input amount of exercise. The exercise information analyzer circuit 23 also calculates the actual amount of exercise in response to a detection output supplied from the exercise information sensor 24

As shown in FIG. 1, the functions of the music replay data generator 22 and the exercise information analyzer circuit 23 enclosed in dual-lined blocks are performed by the program to be executed by the controller 10. More specifically, the functions of the music replay data generator 22 and the exercise information analyzer circuit 23 are implemented by the function of the controller 10.

The exercise information sensor 24 includes at least one sensor of a variety of sensors including an acceleration sensor, a shock sensor, a pressure sensor, a static charge sensor, a distortion sensor, a range sensor, an electric current sensor, and a temperature sensor. The exercise information sensor 24 detects exercise when the user exercises. The exercise information sensor 24 also detects a change in the temperature of the user and a change in the pulse rate of the user. The detection output is supplied to the exercise information analyzer circuit 23 as previously discussed to be used in calculation of the actual amount of exercise. In accordance with the first embodiment, the exercise information sensor 24 may include a shock sensor, and detect the tempo of walking or jogging.

In the audio reproducing apparatus of the first embodiment, the audio signal output processor 31 is supplied with audio data (digital data) as a reproducing target via the controller 10, and D/A (digital to analog) converts the audio data, thereby producing an output analog audio signal. The analog audio signal from the audio signal output processor 31 is supplied to a loudspeaker 32. The loudspeaker 32 emits a sound responsive to the supplied analog audio signal.

The audio signal output processor 31 includes an audio output terminal, although not shown, and when a headphone or an earphone is connected to the audio output terminal, the analog audio signal is supplied from the audio signal output processor 31 to the audio signal output terminal, and then supplied to the connected headphone or the connected earphone. The user can thus listen to a reproduced sound from the headphone or the earphone. When one of the headphone and the earphone is connected to the audio output terminal, no reproduced sound is emitted from the loudspeaker 32.

The display circuit 33 under the control of the controller 10 displays an image on a display screen of the display 34. The display 34 may include a display element such as an LCD (Liquid Crystal Display) or an EL (Electro Luminescence) panel, and has a relatively large display screen area to display a variety of information. Displayed on the display screen of the display 34 under the control of the controller 10 are an operation guidance, an error message, a title of reproduced music, a variety of text information, video information, etc.

The keyboard 41, including a plurality of operation keys, and function keys, receives commands to start and stop playing of music, and to select music to be reproduced, and inputs of personal profile information and a target amount of exercise. The microphone 42 picks up a sound and converts the picked up sound into an electrical signal. An analog audio signal responsive, to the sound picked up by the microphone 42 is supplied to the audio signal input processor 43 for A/D (analog-to-digital) conversion. A resulting digital audio signal is stored on a recording medium such as the music information storage unit 21 by the controller 10.

The external (external input and output) terminal 51 serves as a connection terminal with an external device and receives and captures audio data from another audio reproducing apparatus. Conversely, the external terminal 51 supplies the audio data from the audio reproducing apparatus of the first embodiment to another external device. The I/F 52 receives data via the external terminal and then captures the data into the audio reproducing apparatus of the first embodiment to convert the data into audio data in a processable format. Conversely, the I/F 52 converts the audio data to be output to the other device into audio data in a compatible format with the other device.

As will be also described later, the storage unit 53 stores a variety of data, such as identification information of the reproduced audio data, characteristic information of the audio data, the personal profile information of the user, and exercise amount information calculated. The storage unit 53 also stores the audio data.

As the previously discussed music information storage unit 21, the storage unit 53 reads a variety of data from the recording medium, and writes a variety of data to the recording medium. The recording medium is selected from a variety of recording media including a hard disk, a magneto-optical disk such as MD (Mini Disc), an optical disk such as a CD (Compact Disk) or DVD (Digital Versatile Disk), a semiconductor memory, an IC card memory composed of a semiconductor memory, and a magnetic tape. If the recording medium is a hard disk, the storage unit 53 is a hard disk drive, and if the recording medium is an optical disk, storage unit 53 is an optical disk drive.

The audio reproducing apparatus of the first embodiment, including a communication I/F (interface) 61, is connected to a network 100 such as the Internet to exchange target music data and characteristic information of the music data. When connected to a wireless LAN (Local Area Network) via the transceiver circuit 62 and the transceiver antenna 63, the audio reproducing apparatus can acquire music data and characteristic information.

In response to a command input on the keyboard 41 by the user, the controller 10 controls each element of the audio reproducing apparatus. Via the communication I/F 61, or the external terminal 51 and the I/F 51, or the transceiver circuit 62 and the transceiver antenna 63, the controller 10 receives the music data and the characteristic information of the music data such as total play time, tempo, genre, and tonality of the music data and records the received data on the recording medium of the music information storage unit 21.

A list of music (songs) normally stored on the music replay data generator 22 as the music data is produced by the controller 10. The display circuit 33 displays the list of music on the display screen of the display 34. By selecting the music data to be reproduced from the displayed list of music with the keyboard 41, the user can reproduce the music data.

The controller 10 reads target music data from the music information storage unit 21 in response to a reproducing command containing selection information of the music data received via the keyboard 41, and then supplies the target music data to the audio signal output processor 31. When the audio signal output processor 31 is supplied with the music data, the output analog audio signal is produced as previously discussed. The target music data is output from the loudspeaker 32 or one of the headphone and the earphone connected to the unshown external output terminal. The user can thus enjoy the output sound.

In the audio reproducing apparatus of the first embodiment as described in detail below, the personal profile information, such as the body weight, the body height, the sex, and the age of the user, is input via the keyboard 41. The music data is reproduced based on the personal profile information, the play time of the music data to be reproduced, and the characteristic information such as the tempo. The exercise information analyzer circuit 23 calculates an amount of exercise when a predetermined exercise, such as walking or jogging, is practiced by the user in synchronization with the music responsive to the music data. At the end of the playing of the music data, the display circuit 33 displays the calculated exercise amount information on the display 34 to be indicated to the user.

The audio reproducing apparatus of the first embodiment includes the exercise information sensor 24. When the exercise information sensor 24 detects the exercise of the user, the detected output is supplied to the exercise information analyzer circuit 23. The exercise information analyzer circuit 23 can thus calculate an actual amount of exercise. The actual amount of exercise can also be displayed on the display screen of the display 34 to be indicated to the user.

The amount of exercise practiced by the user is simply and accurately calculated, and then indicated to the user. The user can know how he must exercise to achieve what level of exercise, and can motivate him or her clearly to continue exercise.

As will be described in detail below, when a target amount of exercise is input via the keyboard 41, the function of the exercise information analyzer circuit 23 calculates required exercise time and required exercise intensity. Base on the calculation results, the music replay data generator 22 selects the reproducing music data from the music data stored on the music information storage unit 21. The exercise information analyzer circuit 23 determines the play tempo of the selected music data, a combination of the reproducing music data (play order), and the number of repeated plays of the music data, and reproduces the music data in accordance with the determined results. By exercising in synchronization with the reproduced music, the user can perform the target amount of exercise comfortably.

When the user has exercised, the storage unit 53 stores as history information at least one piece of the identification information of the reproduced music data, the play time of the reproduced music data, the number of plays of the reproduced music data, the personal profile information, and the exercise amount information. At the end of the exercise, the information stored is analyzed. For example, if the storage unit 53 stores the exercise amount information, the user may recognize how he or she has exercised and a total amount of exercise practiced every day.

Amount of Exercise Practiced by the User Being Determined Using the Characteristic Information of the Music Data Reproduced for Exercise A process of determining the amount of exercise practiced by the user based on the characteristic information of the music data is described with reference to FIGS. 2-5. In this process, the user walks or jogs to the music into which the audio reproducing apparatus of the first embodiment reproduces the music data.

Figure 2:
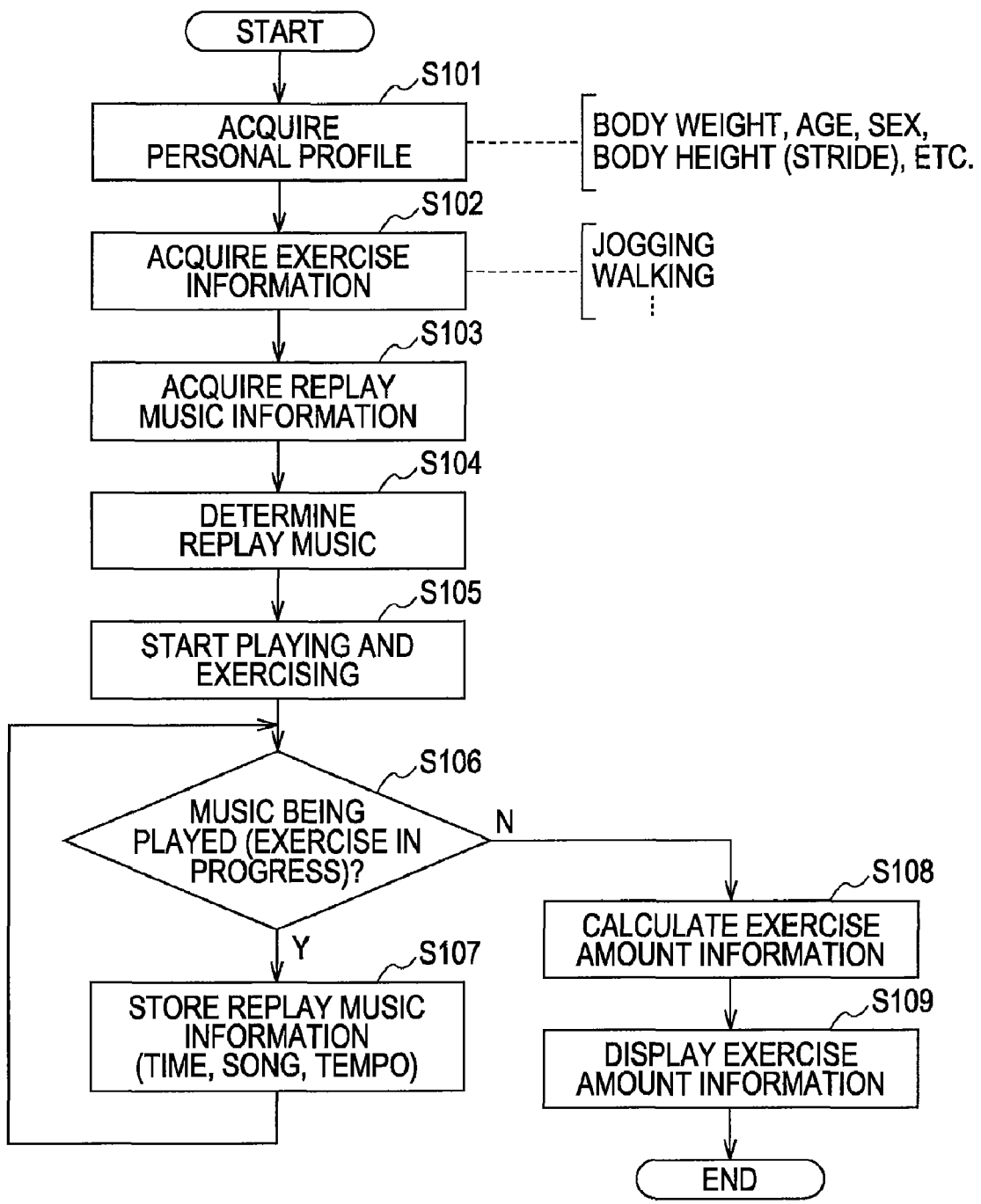
FIG. 2 is a flowchart illustrating a process in which an amount of exercise is determined based on characteristic information of music data reproduced when a user exercises using the audio reproducing apparatus of FIG. 1.

FIG. 2 is a control flowchart of the process in which the amount of exercise is determined based on the characteristic information of the reproduced music data when the user exercises with the audio reproducing apparatus of the first embodiment. The process of FIG. 2 is mainly executed by the controller 10. The controller 10 in the audio reproducing apparatus of the first embodiment receives the body weight, the body height (stride), the age, and the sex of the user required to calculate the amount of exercise of the user via the keyboard 41, and then stores these pieces of information on the RAM 13 (step S101).

The controller 10 receives key input information regarding a type (category) of exercise the user is now going to practice, and then stores the type of exercise on the RAM 13 (step S102). The information regarding the type of exercise (exercise information) indicates categories of exercise, such as walking, jogging, running, etc. The controller 10 in the audio reproducing apparatus acquires characteristic information, such as a title of replayable music data, play time of the replayable music data, and a tempo of the replayable music data and displays the characteristic information in a list on the display 34 to be indicated to the user (step S103).

In step S103, the title and the characteristic information of the replayable music data are read and acquired from the recording medium of the music information storage unit 21. Alternatively, the audio reproducing apparatus may be connected to a network via the communication I/F 61 and may acquire the title and the characteristic information of the replayable music data from a database in a server over the network. When the title and the characteristic information of the replayable music data are acquired from the database over the network, the audio reproducing apparatus searches the title and the characteristic information of the replayable music data according to the identification information of the replayable music data and then acquires the title and the characteristic information of the replayable music data.

The music data to be stored on the recording medium of the music information storage unit 21 may be acquired from a medium such as a CD, or from a database over a network via the communication I/F 61 or the transceiver antenna 63 and the transceiver circuit 62, or from the external device via the external terminal 51 and the I/F 52.

In step S103, the list of the replayable music data displayed on the display screen of the display 34 (replay music information) lists titles of the replayable music data, reproducing times (play times (referred to as "length" in FIG. 3)), and tempos (speed of a music signal, or beat per minute in this embodiment).

The controller 10 receives a selection input of the music data desired to be reproduced by the user, and determines the music data to be reproduced in response (step S104). The controller 10 displays a list of determined music data to be reproduced (replay music list) on the display screen of the display 34 using the display circuit 33, although that process is not required if all replayable music data is to be reproduced.

FIGS. 4A and 4B illustrate an example of the replay music list. For example, if the user wants to continue exercise at a constant intensity for a relatively long time from beginning to end, the same music data may be reproduced repeatedly. For example, if a song A is repeated by 50 times, the controller 10 generates a replay music list 1 composed of titles of the replayable music data, reproducing times (referred to as "length" in FIGS. 4A and 4B), song tempos and the number of plays as shown in FIG. 4A. The controller 10 supplies the replay music list 1 to the display circuit 33 to display the replay music list 1 on the display screen of the display 34 to be indicated to the user.

The replay music list 1 illustrated in FIG. 4A notifies the user that the play time (the length of the song A) having a length of 1 minute 11 seconds long, and a tempo of 100 is to be reproduced 50 times consecutively. If the song A having a length of 1 minute 11 seconds is repeated by 50 times consecutively, the song A is consecutively repeated for about 60 minutes. By exercising to the song A, the user is guided to exercise at a predetermined intensity for about 60 minutes.

The intensity of exercise may be gradually increased, and then flattens off at a content intensity in the middle, and then gradually decreased. Music data having a relatively slow tempo is reproduced first and then music data having a relatively fast tempo is gradually reproduced. Music data having a predetermined tempo is reproduced for a constant period of time, and then the audio reproducing apparatus reproduces music data having a fast tempo and successively changes to music data having a slower tempo.

More specifically, as shown in FIG. 4B, the song A is played by live times, a song C is played once, a song B is played once, a song D is played once, a song E is played 30 times, a song B is played twice, the song C is played once, and then a song F is played once. As described above, the audio reproducing apparatus gradually increases the exercise intensify, and then maintains the intensity of exercise for a constant period of time, and then gradually decreases the intensity of exercise. The audio reproducing apparatus guides the user so that the user naturally controls the intensity of exercise.

The audio reproducing apparatus of the first embodiment receives the command input on the keyboard 41 by the user, and thus determines the reproducing music data, the number of plays of the replayable music data, and the play order of the replayable music data, in response to the operation input entered on the keyboard 41 by the user.

In step S104, the reproducing music data, the number of plays of the replayable music data, and the play order of the replayable music data are determined. Upon receiving a play start command input via the keyboard 41, the controller 10 starts reproducing the music data determined to be reproduced in step S104 (step S105). In synchronization with the music reproduced in step S105, the user practices a predetermined exercise such as walking or jogging in a comfortable and continuous manner.

The controller 10 monitors the processing state of own apparatus, thereby determining whether music playing is in progress (in step S106). If it is determined in the determination step of S106 that the music playing is in progress, the controller 10 stores on the recording medium of the storage unit 53 the information (replay music information), such as the title, the play time, and the tempo of the music data currently reproduced, as play history information (step S107). Steps S107 and S106 are cycled through.

If the controller 10 determines in the determination step of S106 that the playing of the music data has ended, the controller 10 controls the exercise information analyzer circuit 23 to calculate an amount of exercise practiced by the user (step S108). The music information storage unit 21 calculates the amount of exercise of the user using the play history information recorded on the storage unit 53 in step S107, the personal profile information regarding the body weight, the body height the age and the sex of the user and the exercise information acquired in steps S101 and S102 and stored on the RAM 13.

As will be described in detail later, the audio reproducing apparatus of the first embodiment calculates in step S108 the values of the exercise time, the distance walked (distance of travel), the average speed, the calories consumed, and the fat burned when the user has walked or jogged to the music reproduced. Since the type (category) of exercise is input in step S102, the amount of exercise is calculated based on that information faking into consideration the exercise practiced.

The controller 10 controls the display circuit 33, thereby displaying on the display screen of the display 34 information regarding the amount of exercise of the user determined in step S108 (step S109), and ending the process of FIG. 2. FIG. 5 illustrates an example of a display screen for displaying the exercise amount information indicated to the user in step S109. As shown in FIG. 5, the audio reproducing apparatus of the first embodiment displays the information regarding the exercise time, the distance walked, the average speed, the calories consumed, and the fat burned when the playing of the music data ends.

The screen of FIG. 5 notifies the user that he or she has consumed 150 kcal of energy, and burned 20 grams of fat as a result of walking a distance of 3 km to reproduced music for 30 minutes at an average speed of 6 km/h. Also, a label indicating the exercise amount information is shown on the top portion of the screen and a message "Good Exercise!" is shown on the bottom portion of the screen.

In this way, the user, who has practiced a predetermined exercise to the music reproduced by the audio reproducing apparatus, can learn objectively, simply, and accurately how much he or she has exercised. The user can establish his or her own exercise guidance for future exercise, regarding how much exercise amount is achieved by a predetermined exercise such as walking or jogging in terms of exercise time, and intensity of exercise, and how much exercise amount is required of him or her.

The personal profile information temporarily stored on the RAM 13 and the exercise amount information calculated in step S108 are stored together with the play history information on the storage unit 53 for a variety of analyses later.

Calculation Method of a Variety of Exercise Amounts

A calculation process of a variety of exercise amounts performed in step S108 of FIG. 2 is specifically described. As previously discussed, a variety of exercise amounts is calculated when the user practices a predetermined exercise to the music reproduced by the audio reproducing apparatus of the first embodiment. The calculation process is performed based on the personal profile information input by the user, such as the body weight, the body height, the age, and the sex of the user, and the characteristic information regarding the play time and the tempo of the reproduced music data.

The exercise time equals the play time of the music data. By learning how many times which music data has been played, the exercise time is calculated. When the music data determined to be reproduced is reproduced, a time measuring circuit (timer) connected to the controller 10 and not shown in FIG. 1 measures the play time.

The distance walked is calculated based on the personal profile information and the characteristic information of the music data. FIG. 6 illustrates how the distance walked is calculated. As shown in equation (1) of FIG. 6, the stride of the human being is known to be about 45 percent of the body height. As shown in equation (2) of FIG. 6, the distance walked is calculated by multiplying the stride by the number of steps.

As shown in FIG. 6, a 170-cm-tall person now walks to music of 120 tempos for 2 minutes and 30 seconds. As shown in equation (3), the stride of the user is determined by multiplying the body height by 0.45. Since the user walks to the music of 120 tempos (beats per minute), he or she takes 120 steps per minute. The distance walked per minute is determined, by multiplying the stride by 120 (steps), and the resulting distance walked per minute is multiplied by 2 minutes 30 seconds as the exercise time (exercise session time). As shown in FIG. 6, the calculated distance walked is 229.5 m.

The average speed in exercise can be calculated based on the thus calculated exercise time and distance walked. FIG. 7 illustrates how the average speed of exercise is calculated. Since the speed is calculated from distance/time, the average speed is determined by dividing the distance walked by the exercise time as shown in equation (4) of FIG. 7. If the user walks a distance of 3 km for 30 minutes, the speed becomes 6 km/h using equation (5) of FIG. 7.

Two methods can be used to calculate calories consumed (energy consumed). One method uses the energy consumed per minute and the other method uses an METS (Metabolic Equivalents) indicating a value of exercise intensity determined for each exercise type.

FIG. 8 illustrates the method of calculating the energy using the energy consumed per minute. As shown in equation (6) of FIG. 8, energy consumed per minute Wmin is determined by dividing a sum of a speed in exercise and a constant value "35" by a product of a constant value "2000" and the body weight of the user. By multiplying the thus calculated consumed energy Wmin per minute by a total exercise time (minutes), the energy consumed (calories consumed) in exercise throughout the total exercise time is calculated.

As shown in FIG. 8, the calories consumed is now calculated when a 68-kg-weight person now walks at a speed of 100 m/rain for 60 minutes. As shown in equation (7) of FIG. 8, the energy consumed per minute Wmin is determined. As shown in equation (8) of FIG. 8, a total consumed energy is determined by multiplying the energy consumed per minute Wmin by the total exercise time, namely, 60 minutes. The energy consumed (calories consumed) in this case is 275.4 kcal.

FIG. 9 illustrates the method of calculating the consumed energy using the METS value indicating the exercise intensity determined per exercise. The METS value indicates the exercise intensity predetermined for each type of exercise. The METS value will be described more in detail later. As shown in FIG. 9, the METS value is known to be 4-7 for walking, and 7-15 for jogging to practice an effective exercise.

When the energy consumed is determined using the METS value, the product of the body weight of the user, the METS value and the exercise time is calculated. For example, if a 60-kg-weight person practices an exercise of 5 METS for 30 minutes, the consumed energy (consumed calories) is 150 kcal as shown in equation (10) of FIG. 9.

The consumed energy (consumed calories) is determined in this way for each exercise by using the energy consumed per minute or the METS value indicating the exercise intensity determined per exercise. As shown in FIGS. 8 and 9, the consumed energy can be calculated using the body weight of the user as the personal profile information, the exercise time (exercise session time) typically equal to the play time of the music data in the audio reproducing apparatus of the first embodiment, and the speed calculated using the exercise time.

The fat burned is calculated using the consumed energy discussed with reference to FIGS. 8 and 9. FIG. 10 illustrates an amount of fat burned. As shown in FIG. 10, energy of about 7700 kcal is consumed to burn 1 kg (kilograms) fat.

To determine the burned fat amount, the consumed energy (kcal) is divided by 7700 kcal required to burn 1 kg fat as indicated in equation (11) of FIG. 10. To make units consistent, the resulting quotient is multiplied by 1000 g (gram). As previously discussed with reference to FIG. 8, if the exercise is known to have consumed energy of 275.4 kcal, the calculation indicated in equation (12) of FIG. 10 results in the burning of about 35.77 g (gram) fat.

The exercise time, the distance walked, the average speed, the consumed energy (consumed calories), and the burned fat are calculated in this way based on the personal profile information of the user and the characteristic information of the music data when the user exercises listening to the music data reproduced by the audio reproducing apparatus of the first embodiment. In step S108 of FIG. 2, the calculation process discussed with reference to FIGS. 6-10 are performed, and the exercise amount information of FIG. 5 is displayed to the user in step S109.

METS Value

The METS value used in the calculation of the consumed energy discussed with reference to FIG. 9 is described below. FIGS. 11 and 12 illustrate the METS value. As shown in equation (13) of FIG. 11, the METS value is determined by dividing oxygen inhaled during exercise by oxygen inhaled at rest.

As shown in FIG. 11, let "R" represent an oxygen amount consumed (an oxygen amount inhaled) at rest. "H" represent a horizontal locomotion factor as an oxygen amount inhaled to exercise in a horizontal direction, and "V" represent a vertical locomotion factor as an oxygen amount inhaled to exercise in a vertical direction. The horizontal locomotion factor during walking is determined by calculating (0.1× speed) as shown in equation (15) of FIG. 11, and the horizontal locomotion factor during running is determined by calculating (0.2×speed) as shown in equation (16) of FIG. 11. The vertical locomotion factor is determined by calculating (0.9× speed×tilt) as shown in equation (17) of FIG. 11.

The oxygen amount inhaled during exercise is determined by calculations (R+H+V) as shown in equation (14) of FIG. 11. The oxygen amount inhaled at rest is represented by R as described above. The METS value is determined by calculating (R+H+V)/R as shown in equation (13) of FIG. 11. As shown in FIG. 11, 1 METS corresponds to a consumed oxygen amount of 3.5 ml/kg min (mil liters/kilograms minutes), and equals an oxygen amount consumed at rest.

Two specific calculation examples of the METS value are described below with reference to FIG. 12. The METS value is calculated for walking at a speed of 6 km/min. As discussed with reference to FIG. 11, the METS value is calculated if the oxygen amount inhaled at rest R, the horizontal locomotion factor H, and the vertical locomotion factor V are known. Since the oxygen amount inhaled at rest R is known to be 3.5 ml/kg min, the METS value can be calculated if the horizontal locomotion factor H and the vertical locomotion factor V are known.

The horizontal locomotion factor H during walking is determined by calculating (0.1×speed m/min) as shown in equation (15) of FIG. 11. Since a speed of 6 km/h of walking corresponds to a speed of 100 m/min of walking, the horizontal locomotion factor H is calculated to be 10.0 ml/kg min from equation (18) of FIG. 12. The vertical locomotion factor V is determined by calculating (0.9×speed m/min×tilt) as shown in equation (17) of FIG. 11. No tilting generally occurs in the walking on a flat path, tilt=0 rad (%) as shown in equation (19) of FIG. 12. The vertical locomotion factor V becomes 0 (zero).

The oxygen amount inhaled during exercise is determined by summing the oxygen amount inhaled at rest R, the horizontal locomotion factor H and the vertical locomotion factor V as shown in equation (20) of FIG. 12. By dividing the sum by the oxygen amount inhaled at rest R as shown in equation (21) of FIG. 12, the METS value is determined to be "3.9." More specifically, the METS value for the walking at a speed of 6 km/h is "3.9."

The calculation of the METS value for the jogging at a speed of 10 km/h is considered. In the same manner as in the above walking, the oxygen amount inhaled at rest R is already known, and the METS value can be calculated if the horizontal locomotion factor H and the vertical locomotion factor V are learned. A speed of 10 km/h in running corresponds to a speed of 166.7 m/min in running. The horizontal locomotion factor H is calculated to be 33.34 ml/kg mm as shown in equation (22) of FIG. 12.

No tilt generally takes place in exercise in running as in walking, the tilt is zero rad (%) as shown in equation (23) of FIG. 12. The vertical locomotion factor V becomes 0 (zero).

The oxygen amount inhaled during exercise is calculated by summing the oxygen amount, inhaled at rest R, the horizontal locomotion factor H and the vertical locomotion factor V thus determined as shown in equation (24) of FIG. 12. The METS value is thus determined to be "10.5" by dividing the sum by the oxygen amount inhaled at rest R as shown in equation (25) of FIG. 12. More specifically, the METS value in the running at a speed of 10 km/h is "10.5."

The METS value as the exercise intensity of the exercise is thus determined for each type of exercise. When the consumed energy is determined using the METS value, equation (9) of FIG. 9, namely, the body weight×the METS value×the exercise time, is used.

As shown in FIG. 13, the consumed energy (consumed calories) is determined using the METS value when a 60-kg-weight person has run on a flat path at a speed of 10 km/h (speed of 166.7 m/min) for 30 minutes. As shown in equation (26) of FIG. 13, (3.5+166.7×0.2)/3.5 is calculated to determine the METS value. By multiplying the METS value, the body weight (60 kg), and the time ((30/60) hour), the consumed energy becomes "315.77 kcal."

The equation for calculating the consumed energy using the METS value is expressed in detail as shown in FIG. 14. A walking exercise is now considered. A speed of one exercise (speed for taking one step) Vi is determined by dividing one stride Ww by the exercise time Ti (time required to take one step) as shown in equation (27) of FIG. 14.

If the speed Vi of one exercise is determined, the horizontal locomotion factor is determined as described with reference to FIG. 11. When the user exercises at a location that is tilted, the vertical locomotion factor can be determined if the tilt angle is known. Since the walking in the flat location is generally free from tilt, the METS value of one exercise is determined in accordance with equation (13) of FIG. 11 if the horizontal locomotion factor is known.

As shown in equation (28) of FIG. 14, the energy consumed in the exercise is calculated by summing the products of the body weight, the METS value METS(Vi) determined from the speed Vi of one exercise, and the time Ti of one exercise over the total time. Equation (28) of FIG. 14 is summarized as equation (29) of FIG. 14.

The METS value is typically 2 to 3 for a walking exercise at a speed of 3.2 km/h, the METS value is typically 3 to 4 for a walking exercise at a speed of 4.8 km/h, the METS value is typically 5 to 6 for a walking exercise at a speed of 6.4 km/h, and the METS value is typically 6 to 7 for a walking exercise at a speed of 8 km/m.

The METS value is typically 7 to 8 for a jogging exercise at a speed of 8 km/h, the METS value is typically 11 for a jogging exercise at a speed of 10 km/h, and the METS value is 12.5 for a jogging exercise at a speed of 12 km/h. The METS values are determined for other variety of exercises. Cycling, aerobic dance, jump rope, and racquet ball are exercises of relatively high METS values.

The exercise amount information such as the amount of exercise of the user is quickly and accurately determined if the personal profile information such as body weight, the body height, and the stride of the user having exercised, and attribute information such as the tempo of the music reproduced during the exercise are known. The exercise amount information can be conveyed to the user or stored for later analysis. If more detailed information, such as the age and the sex of the user, is available, more detailed and accurate exercise information may be calculated and used.

Amount of Exercise Practiced by the User Determined Taking into Consideration Detection Output from Exercise Information Sensor Mounted on Audio Reproducing Apparatus In the above example, the amount of exercise of the user who has walked or jogged to the reproduced music is determined using the tempo of the reproduced music. As discussed with reference to FIG. 1, the audio reproducing apparatus of the first embodiment includes the exercise information sensor 24. The tempo of the exercise of the user can be detected from the deflection output from the exercise information sensor 24 to determine more accurately the amount of exercise of the user.

Using information from the exercise information sensor 24, the tempo of the actual exercise of the user is detected to modify the tempo of the music being reproduced. For example, the tempo of the music being reproduced is increased if the tempo of the exercise is decreased. The tempo of the music being reproduced is decreased if the tempo of the exercise is increased. In such a case, the tempo of the exercise of the user can be accurately learned by means of the exercise information sensor 24. The amount of exercise of the user can be accurately determined.

FIG. 15 is a flowchart of a process in which the audio reproducing apparatus of the first embodiment of FIG. 1 determines the amount of exercise of the user who exercises to the music data reproduced by the audio reproducing apparatus, in the process, the audio reproducing apparatus generates music data from a preset amount of exercise and reproduces the generated music data and determines the amount of exercise from a walking exercise or a jogging exercise practiced by the user.

The controller 10 in the audio reproducing apparatus of the first embodiment receives the personal profile information input on the keyboard 41, such as the body weight, the body height (stride), the age and the sex of the user required to calculate the amount of exercise of the user, and stores the personal profile information on the RAM 13 (step S201). The information such as the body weight and the body height is needed to calculate the amount of exercise, such as the calories consumed and the distance walked (exercise distance), and the information such as the age and the sex is needed to be displayed at the end of the exercise.

The controller 10 in the audio reproducing apparatus receives target energy (target exercise amount) to be consumed by the user in the exercise, and an exercise mode (step S202). The exercise modes include a constant mode for exercising at a constant speed (constant load), a random mode for exercising at a randomly changing speed (or load), a hill mode for exercising at a gradually increasing speed (load), exercising at a constant speed for a period, and then exercising at a gradually decreasing speed. The exercise mode is thus related to a load pattern applied to the user.

The types (categories) of the exercise, such as walking, jogging, running, etc. may be also input. When the type of exercise is input, the amount of exercise is learned taking into consideration the intensity of the target exercise.

The controller 10 in the audio reproducing apparatus acquires the characteristic information, such as the title, the play time, and the tempo of the replayable music data (step S203), generates a replay music list responsive to the target energy consumed, the exercise mode, and the type of the exercise, and displays the replay music list on the display 34 to be indicated to the user (step S204).

In step S204, the replay music list illustrated in FIGS. 4A and 4B is generated. FIG. 4A illustrates an example of the replay music list in which the target energy consumed is set to be 500 kcal with the exercise mode being the constant mode. FIG. 4B illustrates an example of the replay music list in which the exercise intensity rises and falls including warm-up and cool-down phases.

The controller 10 in the audio reproducing apparatus receives via the keyboard 41 a command input as to whether to modify the tempo of the reproduced music in response to the detection result of the exercise information sensor 24 (yes/no in the modification of the tempo of the music during playing) (step S205). If a mode to modify the play tempo is selected, the music (song) tempo reproduced in synchronization with the exercise tempo or rhythm is varied. If a mode not to modify the play tempo is selected, information from the exercise sensor is used to calculate accurately the exercise amount information.

The controller 10 in the audio reproducing apparatus controls each element of the audio reproducing apparatus, thereby starting reproducing the music data selected in the replay music list and prompting the user to start exercise (step S206). The exercise information analyzer circuit 23 in the audio reproducing apparatus acquires the detection output from the exercise information sensor 24 (step S207), calculates the exercise tempo or rhythm of the user from the detection output from the exercise information sensor 24, and then supplies the exercise tempo or rhythm to the controller 10 (step S208).

In response to the calculation results (analysis results) from the exercise information analyzer circuit 23, the controller 10 determines whether the tempo of the reproduced music needs to be modified (step S209). If there is a large discrepancy between the exercise tempo of the user and the tempo of the reproduced music, the controller 10 determines in step S209 that the tempo of the reproduced music needs to be modified. If there is no or small discrepancy between the exercise tempo of the user and the tempo of the reproduced music, the controller 10 determines in step S209 that the tempo of the reproduced music does not need to be modified.

If it is determined in step S209 that the tempo of the reproduced music needs to be modified, the controller 10 controls the music replay data generator 22, thereby modifying the tempo of the music reproduced (step S210).

Subsequent to step S210 or if it is determined in step S209 that the modification of the tempo of the reproduced music is not necessary, the controller 10 monitors the processing status of own apparatus to determine whether the playing of the music is in progress (step S211). If it is determined in the determination step S211 that the playing of the music is in progress, the title, the play time, and the tempo of the music data (replay music information) being reproduced are stored as the play history information on the recording medium of the storage unit 53 and information, such as the exercise tempo, rhythm, and the number steps are stored as exercise history information on the recording medium of the storage unit 53 (step S212). Processing returns to step S207.

If the controller 10 determines in step S211 that the playing of the music data has ended, the controller 10 controls the exercise information analyzer circuit 23 to calculate the amount of exercise of the user (step S213). The exercise information analyzer circuit 23 calculates the amount of exercise practiced by the user as described with reference to FIGS. 6-14, based on the play history information and the exercise history information recorded on the recording medium of the storage unit 53 in step S212, and the personal profile information regarding the body weight, the body height, the age and the sex of the user and the exercise information acquired and temporarily stored on the RAM 13 in steps S201 and 202.

In step S213, the exercise time, the number of steps, the distance walked (distance of travel), the average speed, the amount of calories consumed, and the amount of fat burned are calculated when the user has walked or jogged to the music reproduced. The energy consumed (calories consumed) is calculated simply and accurately using equations shown in FIG. 14. The controller 10 controls the display circuit 33, thereby displaying the information indicating the amount of exercise of the user determined in step S213 on the display screen of the display 34 (step S214). The process of FIG. 15 thus ends.

FIG. 16 illustrates an example of the display screen of the exercise amount information displayed to the user in step S214. As shown in FIG. 16, when the playing of the music data has been completed, the audio reproducing apparatus of the first embodiment displays information regarding the exercise time, the number of steps, the distance walked, the average speed, the consumed calories, the burned fat amount, etc.

The screen of FIG. 16 notifies that the user having walked to the reproduced music walked 10000 steps, namely, 3 km at a speed of 6 km/h for 30 minutes, consumed energy of 150 kcal (kilo calories), and burned 20 gram fat. Also, a label indicating the exercise amount information is shown on the top portion of the screen and a message "Good Exercise!" is shown on the bottom portion of the screen.

Using the information from the exercise information sensor 24, the user can learn the actual tempo of the exercise and then modify the tempo of the reproduced music. In this case, as well, the amount of exercise of the user can be accurately determined because the exercise information sensor 24 allows the tempo of the exercise of the user to be accurately determined.

In this case, as well, for analysis after the exercise, the storage unit 53 can store the personal profile information and the exercise information input by the user, and the exercise amount information calculated in step S213.

Selecting and Determining the Music Data to be Reproduced Based on Preset Exercise Amount and Calculating the Amount of Exercise Using the Characteristic Information of the Music Data FIGS. 17-20 describe a process in which the music data to be reproduced is selected and determined based on a preset exercise amount and the exercise amount is calculated using the characteristic information of the reproduced music data.

Figure 17:
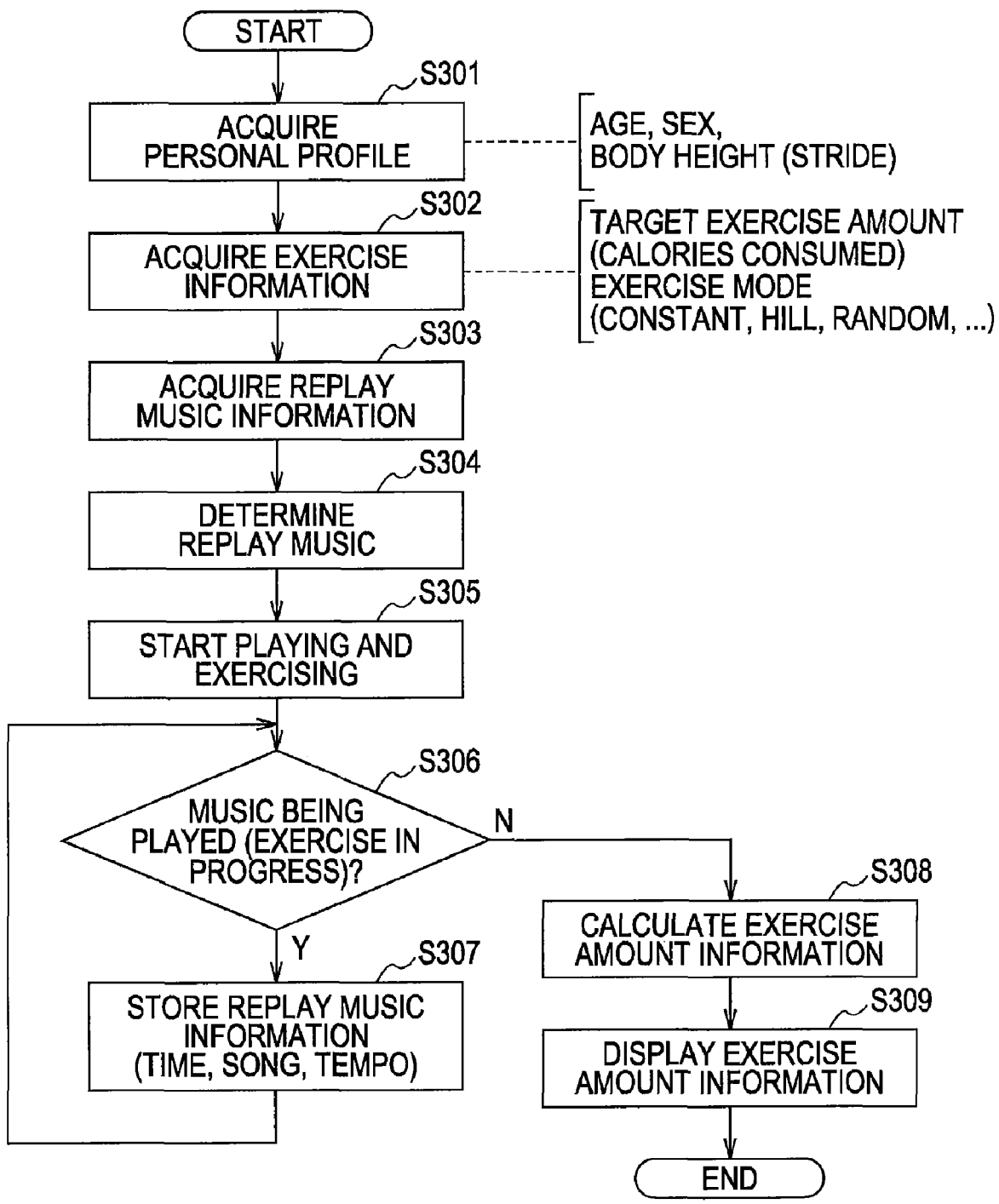
FIG. 17 is a flowchart illustrating a process in which audio data to be reproduced from a preset amount of exercise is selected, determined, and then reproduced.

FIG. 17 is a flowchart of a process of the audio reproducing apparatus of FIG. 1 used by the user in an exercise, in the process, the audio reproducing apparatus selects and determines the music data to be reproduced from the present exercise amount (target exercise amount), and reproduces the determined music data. The process of FIG. 17 is substantially identical to the process of FIG. 15 but without a process relating to the modification of the tempo of the reproduced music (including steps S205 and S207-S210).

In the process of FIG. 17, the controller 10 in the audio reproducing apparatus receives via the keyboard 41 the key input personal profile information relating to the body weight, the body height (stride), the age, and the sex of the user required to calculate the amount of exercise of the user and stores the personal profile information on the RAM 13 (step S301). The information input here, such as the body weight and the body height, is needed to calculate the amount of exercise, such as the calories consumed and the distance walked (exercise distance), and the information such as the age and the sex is needed to be displayed at the end of the exercise.

The controller 10 in the audio reproducing apparatus receives target energy (target exercise amount) to be consumed by the user in the exercise and an exercise mode and stores these pieces of information on the RAM 13 (step S302). As previously discussed with reference to FIG. 15, the exercise modes include the constant mode for exercising at a constant speed, the random mode for exercising at a randomly changing speed, the hill mode for exercising at a gradually increasing speed, exercising at a constant speed for a period, and then exercising at a gradually decreasing speed. The types (categories) of the exercise, such as walking, jogging, running, etc. may be also input.

The controller 10 in the audio reproducing apparatus acquires the characteristic information, such as the title, the play time, and the tempo of the replayable music data, and the consumed energy, and the distance of travel in the exercise (step S303). The characteristic information, such as the title, the play time, and the tempo of the replayable music data, and the consumed energy, and the distance of travel in the exercise is determined based on each music (song).

The consumed energy is the one consumed by the player (user) when the user exercises to the music output in response to the playing of the music data. The distance of travel in the exercise is the one traveled by the player (user) when the user exercises to the music output in response to the playing of the music data. A plurality of different values are set for each of the consumed energy and the distance of travel of the user in response to the intensity of the exercise.

FIG. 18 illustrates an example of a list of replayable music data (replay music information) acquired in step S303. FIG. 18 lists information relating to the title of the replayable music data, the length of the music reproduced in response to the music data (play time), the tempo of the replayable music data, and the energy consumed when the user exercises from beginning to end to the music responsive to the playing of the music data.

The controller 10 in the audio reproducing apparatus generates the replay music list as a list of the music data to be reproduced, based on the personal profile information acquired in step S301, the information regarding the consumed calories and the type of the exercise acquired in step S302, and the characteristic information of the music data acquired in step S303, thereby determining the music data to be reproduced (step S304).

In step S304, the controller 10 generates the replay music lists shown in FIGS. 19A and 19B. FIG. 19A illustrates an example of the replay music list in which the target energy consumed is set to be 500 kcal with the exercise mode being the constant mode. FIG. 19B illustrates an example of the replay music list indicating a hill mode (rise and fall mode) in which the exercise intensity rises and falls including warm-up and cool-down phases.

The controller 10 in the audio reproducing apparatus controls each element of the audio reproducing apparatus, thereby starting reproducing the music data selected in the replay music list and prompting the user to start exercise (step S305). The controller 10 monitors the processing status of own apparatus, thereby determining whether the playing of the music is in progress (step S306). If it is determined in the determination step S306 that the playing of the music is in progress, the controller 10 stores on the recording medium of the storage unit 53 as the play history information the information (replay music information) regarding the title, the play time, the tempo of the music data currently being reproduced (step S307). Processing returns to step S307. In this case, essential information is the play time, but other information may also be recorded for displaying purposes.

If it is determined in the determination step S306 that the playing of the music data has ended, the controller 10 controls the exercise information analyzer circuit 23 to calculate the amount of exercise (step S308). The exercise information analyzer circuit 23 thus calculates the amount of exercise practiced by the user as previously discussed with reference to FIGS. 6-14 based on the play history information stored on the recording medium of the storage unit 53 in step S307, the personal profile information regarding the body weight, the body height, the age and the sex of the user acquired and temporarily stored on the RAM 13 in steps S301 and S302.

In step S308, the exercise time, the number of steps, the distance walked (distance of travel), the average speed, the amount of calories consumed, and the amount of fat burned are calculated when the user has walked or jogged to the music reproduced. The controller 10 controls the display circuit 33, thereby displaying the information indicating the amount of exercise of the user determined in step S213 on the display screen of the display 34 (step S309). The process of FIG. 17 thus ends.

Figures 20, 21:
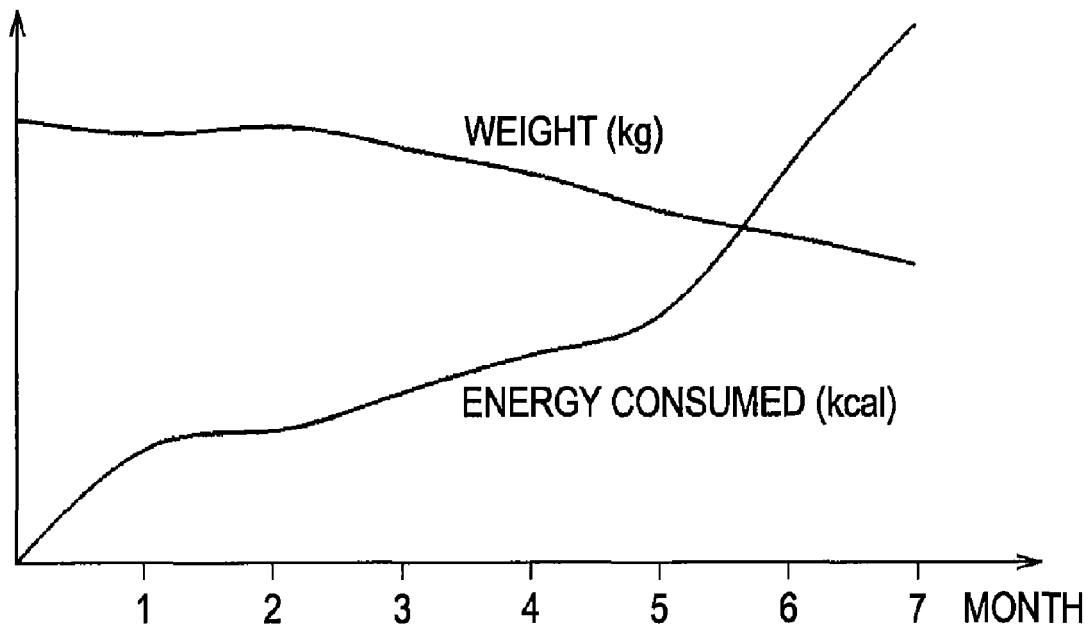
FIG. 20 illustrates an example of the display screen of the exercise amount information.
FIG. 21 illustrates analysis results of history information.

FIG. 20 illustrates an example of the display screen of the exercise amount information displayed to the user in step S309. As shown in FIG. 20, when the playing of the music data has been completed, the audio reproducing apparatus of the first embodiment displays information regarding the target consumed calories, the exercise time, the distance walked, the average speed, the burned fat amount, etc.

The screen of FIG. 20 notifies that in order to consume energy of 500 kcal, the user had to continuously walk to the reproduced music 3 km at a speed of 6 km/h for 30 minutes. The fat consumed is 20 g. Also, a label indicating the exercise amount information is shown on the top portion of the screen and a message "good exercise!" is shown on the bottom portion of the screen.

By inputting information regarding the target energy to be consumed, a required amount of exercise is displayed in the music data to be reproduced and the number plays of the music data with respect to the consumed calories of the music data. The music data may be reproduced as displayed, and the user may walk or jog to the reproduced music. When all the music data to be reproduced is played by the displayed number of times, the user can finish the exercise of the target consumed calories. By simply exercising to the reproduced music, the user can achieve the target exercise amount.

In this case, as well, for analysis after the exercise, the storage unit 53 can store the personal profile information and the exercise information input by the user, and the exercise amount information calculated in step S308.

The audio reproducing apparatus of the first embodiment reproduces a variety of music data. In the exercise practiced to the music data, the user can naturally synchronize with the reproduced music tempo and rhythm in a comfortable manner.

Since the exercise amount information relating to the exercise practiced by the user is indicated to the user, the user can motivate him or her to continue the exercise. An exercise, which may need to be repeated within a predetermined period of time, can be repeated comfortably. The user can thus enjoy the exercise. Since the play history information, the personal profile information, and the exercise amount information can be managed by the audio reproducing apparatus for the user's personal use, personal information of the user is securely managed.

As shown in FIG. 1, the audio reproducing apparatus of the first embodiment includes the storage unit 53. As previously discussed, the storage unit 53 may store the personal profile information, the exercise amount information, and the replay music information, etc. for later retrieval for a variety of analyses. For example, as shown in FIG. 21, the relationship between a change in the body weight of the user and a cumulative value of the energy consumed in the exercise may be plotted in graph. The user is notified of the effect of exercise from many directions. The effect of exercise can be recognized using the audio reproducing apparatus of the first embodiment.

By inputting information regarding the target energy to be consumed, a required amount of exercise is displayed as the music data to be reproduced and the number plays of the music data with respect to the consumed calories of the music data. The music data may be reproduced as displayed, and the user may walk or jog to the reproduced music. When all the music data to be reproduced is played by the displayed number of times, the user can finish the exercise of the target consumed calories. By simply exercising to the reproduced music, the user can achieve the target exercise amount.

The audio reproducing apparatus of the present invention may be relatively easily implemented by producing the program for the processes discussed with reference to the flowcharts of FIGS. 2, 15 and 17 and loading the program on one of a variety of audio reproducing apparatuses.

In the first embodiment, the controller 10, the music information storage unit 21, and the audio signal output processor 31 working in cooperation constitute reproducing means, and the controller 10, the communication I/F 61, the transceiver circuit 62, and the I/F 52 working in cooperation perform the function of acquisition means working in response to a supply source of the characteristic information. The controller 10 and the exercise information analyzer circuit 23 perform the function of calculating means, and the display circuit 33 and the display 34 working in cooperation perform the function of output means. One of the controller 10 and a music replay data generating apparatus perform the function of determining means for determining the music data to be reproduced.

Each of the exercise amount information or the target exercise amount information may be one of the exercise time, the exercise intensity, the exercise distance, and the burned fat amount in addition to the consumed calories. When the exercise time is used as the target exercise amount information, time throughout which the user desires to continue the exercise (exercise time) is input as the target exercise amount information. The audio data having the play time equal to the input time information can be selected. When the burned fat amount is input as the target exercise amount information, the music data to be reproduced is selected and determined so that the input fat amount is burned.

When the music data to be reproduced is selected and determined, the type (genre), the tempo, the combination, and the number of repeated plays of the music data to be reproduced may be automatically determined. For example, the music data of a genre appropriate for the target exercise amount may be selected by attaching information indicating the genre to the characteristic information of the music data. The tempo, the combination, and the number of plays may be automatically determined based on the target exercise amount.

By incorporating information relating to the exercise intensity such as the consumed energy for each exercise in the replay music information of FIG. 18, a detailed process on a per exercise basis may be performed. The exercise intensity may be determined depending on the speed of each exercise or each of the type of the exercise including walking, jogging, running, jump rope, etc.

As previously discussed, the replayable music data may be supplied in a recorded state thereof on a recording medium such as CD (Compact Disk), MD (Mini Disc), or a card memory. The recording medium may be loaded on the music information storage unit 21 for reading and playing. The replayable music data may be acquired in communication with a server over a network or a wireless LAN via the communication I/F 61 and the transceiver circuit 62, and recorded on the recording medium of the music information storage unit 21 for recording and playing. The music data can be directly reproduced from an external device connected to the external terminal 51 or recorded from the external device on the recording medium of the audio signal output processor 31 for playing.

As previously discussed, the characteristic information of the music data, such as the play time and the tempo of the replayable music data, and the consumed calories responsive to the exercise intensify may be recorded on the recording medium together with the music data. Alternatively, the characteristic information, together with the music data or separately from the music data, may be supplied via a wide area network such as the internet or a wireless LAN, or from an external device connected to the external terminal 51. The music data and the characteristic information thereof may be separately acquired if the music data and the characteristic information are associated with each other by identification information (ID) of the music data.

The type of the exercise is also received as the exercise information in the process of the first embodiment discussed with reference to the flowchart of FIG. 2 wherein the exercise amount is determined based on the characteristic information of the reproduced music data. The present invention is not limited to this method. When the consumed energy is calculated without using the METS value, there is no need for learning the type of exercise required to calculate the METS value as the exercise intensity. Inputting the type of exercise is not required.

The audio reproducing apparatus of the first embodiment is a mobile music reproducing apparatus. More specifically, the audio reproducing apparatus is applicable to a variety of types of apparatuses including a hard disk player, an MD player, and a cellular phone. The present invention is appropriate for use in a mobile apparatus. The audio reproducing apparatus may be used in a stationary fashion. For example, the audio reproducing apparatus for the compact design thereof may be mounted on a variety of fitness machines.

Second Embodiment

In accordance with the first embodiment, the user selects the music data to be reproduced by the audio reproducing apparatus one song by one song to produce the replay music list, and uses the replay music list. Also, the user selects the music data to be reproduced based on the input target exercise amount information to generate and use the replay music list. The present invention is not limited to this method.

An audio reproducing apparatus of a second embodiment automatically generates a replay music list containing a play order of at least one song of music data and the number of plays of at least one song of the music data or registers beforehand such a replay music list. A plurality of replay music lists is thus made available.

When the user exercises to the music data that is being reproduced, the audio reproducing apparatus of the second embodiment allows the user to select one replay music list to be actually used from among the plurality of available replay music lists.

The audio reproducing apparatus of the second embodiment reproduces the music data in accordance with the replay music list selected by the user. The user can modify the selected replay music list in terms of the song to be reproduced and the number of plays of each song.

The audio reproducing apparatus of the second embodiment makes a plurality of replay music lists available, thereby facilitating the input operation of the user to the audio reproducing apparatus and allowing a variety of music data to be reproduced in a manner satisfying the user's intention (the user's needs).

The audio reproducing apparatus of the second embodiment is different from the audio reproducing apparatus of the first embodiment in that a plurality of replay music lists are used. However, the audio reproducing apparatus of the second embodiment is identical in structure to the audio reproducing apparatus of the first embodiment discussed with reference to FIG. 1. The structure of the audio reproducing apparatus of the second embodiment is thus shown in FIG. 1, and the audio reproducing apparatus of the second embodiment is also discussed with reference to FIG. 1.

The audio reproducing apparatus of the second embodiment has a play mode in which the audio data is reproduced in accordance with one of a replay music list automatically generated using the personal profile information, etc. and a preregistered replay music list, and a play mode in which the music data is reproduced in accordance with a replay music list automatically generated using the target exercise amount and the pre-registered replay music list. Which mode to use is determined by the user. In the discussion that follows, the two modes for reproducing the music data are separately described.

Figure 22:
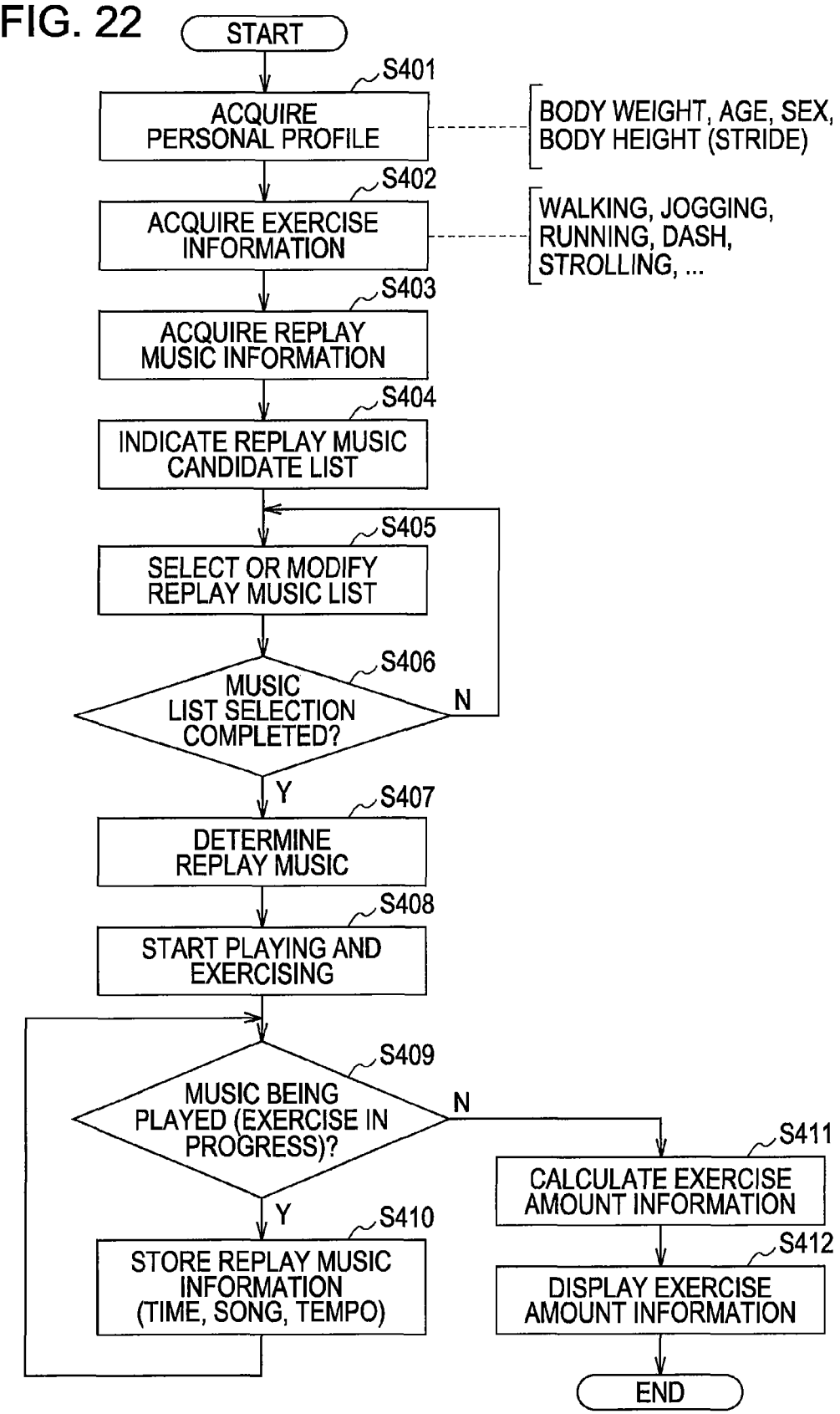
FIG. 22 is a flowchart illustrating another process in which the amount of exercise is determined based on the characteristic information of the reproduced music data.

Playing of the Audio Data in Accordance with One of the Replay Music List Automatically Generated Using the Personal Profile Information, Etc. and the Pre-Registered Replay Music List The playing of the audio data in accordance with one of the replay music list automatically generated using the personal profile information, etc. and the pre-registered replay music list is described below. FIG. 22 is a flowchart illustrating a control flow in which the exercise amount is determined from the reproduced music data when the user has exercised with the audio reproducing apparatus of the second embodiment. The flowchart illustrates the operation of the audio reproducing apparatus of the second embodiment that reproduces the audio data in accordance with one of the replay music list automatically generated using the personal profile information, etc. and the pre-registered replay music list.

The process of FIG. 22 is mainly executed by the controller 10 as the process of FIG. 2 of the audio reproducing apparatus of the first embodiment. The controller 10 in the audio reproducing apparatus of the second embodiment receives via the keyboard 41 the key input personal profile information, such as the body weight, the body height (stride), the age and the sex of the user required to calculate the amount of exercise of the user, and then stores the received personal profile information on the RAM 13 (step S401).

The controller 10 in the audio reproducing apparatus receives key input information indicating the type (category) of the exercise the user is going to practice, and then stores the information on the RAM 13 (step S402). The input information indicates the type of the exercise (exercise information), such as walking, jogging, running, dash, strolling, etc. The controller 10 in the audio reproducing apparatus then acquires the characteristic information, such as the title, the play time, and the tempo of the replayable music data (step S403).

Figures 23, 24A, 24B:
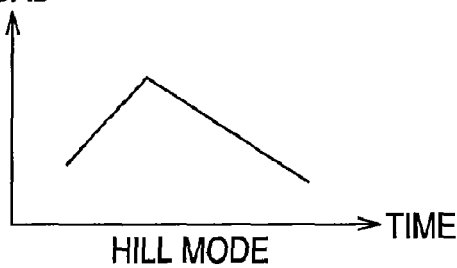
FIG. 23 illustrates one example of the replay music list as a list of music data to be reproduced.
FIG. 24A illustrates an example of a replay music list (hill mode) as a list of music data to be reproduced.
FIG. 24B illustrates an example of a replay music list (hill mode) as a list of music data to be reproduced.

FIG. 23 illustrates the replay music information composed of the title of the replayable music data and the characteristic information of the audio reproducing apparatus of the second embodiment. As shown in FIG. 23, the replay music information includes, as previously discussed, the title of the replayable music data, the play time (referred to as "length" in FIG. 23), the song tempo of the music data (the speed of the music signal, and beat per minute (BPM) as in the first embodiment), etc.

The title and the characteristic information of the replayable music data may be read and acquired from the recording medium of the music information storage unit 21. The title and the characteristic information may also be acquired from a database in a server over a network to which the audio reproducing apparatus is connected via the communication I/F 61. To acquire from the database over the network the title and the characteristic information of the replayable music data, the audio reproducing apparatus may search for and acquire the title and the characteristic information according to the identification information of the replayable music data.

The replayable music data to be stored on the recording medium of the music information storage unit 21 may be acquired from a medium such as CD (Compact Disk), from a database over a network via the transceiver antenna 63 and the transceiver circuit 62, or from an external device via the external terminal 51 and the I/F 52. The replay music information composed of the title and the characteristic information of the acquired replay music is temporarily stored on the RAM 13 for use. The replay music information of FIG. 23 is generated on the recording medium of the music information storage, unit 21 and read and stored temporarily onto the RAM 13 for use.

The replay music information composed of the title and the characteristic information of the acquired replayable music data shown in FIG. 23 may be displayed on the display 34 to notify the user. The user can thus recognize the data stored on the music information storage unit 21 as the replayable music data.

The controller 10 in the audio reproducing apparatus of the second embodiment controls the display circuit 33 to display the replay music list. The display circuit 33 displays on the display 34 as the replay music list the replay music list automatically generated using the replay music information, etc. of FIG. 23 and the pre-registered replay music list to be indicated to the user (step S404).

As will be described more in detail later, the replay music list displayed in step S404 may be a replay music list automatically generated in response to the exercise mode shown in each of FIGS. 24A, 24B, 25A, 25B, 26A and 26B or a prepared in advance (pre-registered) replay music list shown in one of FIGS. 27A and 27B.

These usable replay music lists are stored on the recording medium in the storage unit 53 or on the recording medium in the music information storage unit 21 or a non-volatile memory such as an EEPROM not shown in FIG. 1. The usable replay music list may be displayed on the display screen of the display 34 as shown in FIGS. 28A and 28B, for example. The replay music list, candidates may thus be displayed with all lists at a time or with one list by one list successively.

The controller 10 receives via the keyboard 41 one of a selection input of the replay music list and a modification input to the selected replay music list entered by the user (step S405), and determines whether the input operation of one of the selection input of the replay music list and the modification input to the selected replay music list has been completed (step S406).

If it is determined in the determination step S406 that the input operation of the user has not been completed, processing returns to step S405. If it is determined in determination step S406 that the input operation of the user has been completed, the controller 10 determines, as a replay music list to be used, one of the selected replay music list and the selected and then modified replay music list (step S407).

In accordance with the replay music list determined in step S407, the controller 10 performs a series of reproducing steps, namely, successively reads the music data to be reproduced from the recording medium of the music information storage unit 21, supplies the read music data to the audio signal output processor 31, and causes a sound responsive to the read music data to be emitted from the loudspeaker (step S408). In step with (in synchronization with) the thus reproduced music, the user starts playing exercise of one of the types, such as walking, jogging, running, dash, and strolling, input in step S402.

The controller 10 monitors the processing state of own apparatus, thereby determining whether the music playing is in progress (step S409). If it is determined in the determination step S409 that the music playing is in progress, the storage unit 53 stores as the play history information the information (replay music information) regarding the title, the play time, and the tempo of the music data now being reproduced (step S410). Processing returns to step S409.

If it is determined the determination step S409 that the playing of the music data has been completed, the controller 10 controls the exercise information analyzer circuit 23 to calculate the amount of exercise practiced by the user (step S411). More specifically, the exercise information analyzer circuit 23 calculates the amount of exercise based on the play history information recorded on the recording medium of the storage unit 53 in step S410, the personal profile information composed of the body weight, the body height, the age and the sex of the user and the exercise information acquired and then temporarily stored on the RAM 13 in steps S401 and S402. As the audio reproducing apparatus of the first embodiment as discussed with reference to FIGS. 6-14, the audio reproducing apparatus of the second embodiment calculates the amount of exercise practiced by the user in step S411.

The controller 10 controls the display circuit 33, thereby displaying the information indicating the amount of exercise of the user determined in step S411 on the display screen of the display 34 (step S412). The process of FIG. 22 thus ends. As the audio reproducing apparatus of the first embodiment, as will be also described later, the audio reproducing apparatus of the second embodiment notifies the user of the amount of exercise of the user in step S412 in the same manner as the one shown in FIG. 16.

Specific Examples of the Replay Music List

A specific example of the replay music list indicated to the user in step S404 of FIG. 22 and the display examples thereof are described with reference to FIGS. 24A through 28B. In step S404 of FIG. 22 as previously discussed, a plurality of usable replay music lists such as the automatically generated replay music list and the replay music list prepared in advance are displayed on the display screen of the display 34 to be indicated to the user.

FIGS. 24A-25B illustrate the replay music list that is automatically generated from the play history information of FIG. 23 by the audio reproducing apparatus of the second embodiment. The audio reproducing apparatus of the second embodiment generates the replay music list based on the personal profile information acquired in step S401 and the exercise information acquired in step S402 as shown in FIG. 22, FIGS. 27A and 27B illustrate an example of the replay music lists prepared in advance.

The replay music list automatically generated based on the personal profile information and the exercise information is described. The personal profile information is used to prevent an excess load from being put on the user, in other words, used to limit available tempo or total play time of the music data corresponding to the time throughout which the user practices exercise. More specifically, the personal profile information is used to exclude music of tempos resulting in an excessive load or to limit the total play time of the music data in view of the body height and body weight of the user, or to limit the tempos of the available songs and the total play time of the music data in view of the sex and age of the user.

As previously discussed, the exercise information acquired in step S402 of FIG. 22 indicates the types of exercise including walking, jogging, running, dash, strolling, etc. The exercise information is used to select the tempo of an available song taking into consideration the type of the exercise the user is going to practice.

The personal profile information regarding the age, the body height, and the body weight and the exercise information indicating the type of exercise are used to limit the total play time of the music data corresponding to the time throughout which the user exercises. In other words, the personal profile information and the exercise information input by the user and acquired by the audio reproducing apparatus of the second embodiment are used not only to calculate the amount of exercise but also to serve as a guide according to which the user can safely exercise to the reproduced music.

In accordance with the second embodiment, the audio reproducing apparatus automatically generates a plurality of usable replay music lists based on the acquired personal profile information and exercise information of the user in view of the exercise modes such as the hill mode, the constant mode, and the random mode.

FIG. 24A illustrates an automatically generated replay music list 1. The audio reproducing apparatus of the second embodiment generates the replay music list 1 for the hill mode based on the acquired personal profile information and exercise information. In the hill mode as shown in FIG. 24B, the load of exercise gradually increases with time to a predetermined level, and after reaching the predetermined level, the load of the exercise gradually decreases.

The replay music list 1 of FIG. 24A is generated from the replay music list of FIG. 23. The replay music list 1 lists six songs of a song A (length: 1 minute and 11 seconds, and tempo: 100), a song B (length: 2 minutes and 22 seconds, and tempo: 120), a song C (length: 3 minutes and 33 seconds, and tempo: 105), a song D (length: 2 minutes and 30 seconds, and tempo: 145), a song E (length: 1 minute and 50 seconds, and tempo: 180), and a song F (length: 3 minutes and 00 second, and tempo: 80). The replay music list 1 thus commands that five plays of the song A, one play of the song C, one play of the song B, one play of the song D, thirty plays of the song E, two plays of the song B, one play of the song C, and one play of the song F be reproduced in that order. The replay music list 1 thus allows the user to exercise for a total time of about 80 minutes.

Figure 25B:
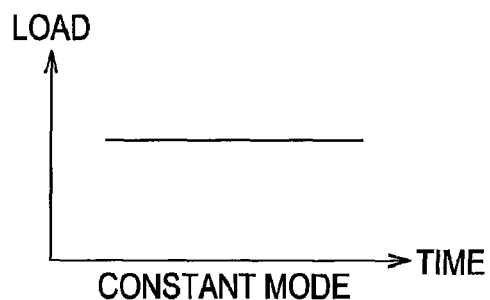
FIG. 25B illustrates an example of a replay music list (constant mode) as a list, of music data to be reproduced.

FIG. 25A illustrates an automatically generated replay music list 2. The audio reproducing apparatus of the second embodiment generates the replay music list 2 for the constant, mode based on the acquired personal profile information and exercise information. In the constant mode as shown in FIG. 25B, the load of exercise remains constant throughout the exercise.

The replay music list 2 of FIG. 25A is generated from the replay music information of FIG. 23, and indicates 50 consecutive plays of the song A (length: 1 minute and 11 seconds, and tempo: 100). In accordance with the replay music list 2, the user exercises for a total time of about 60 minutes.

Figure 26B:
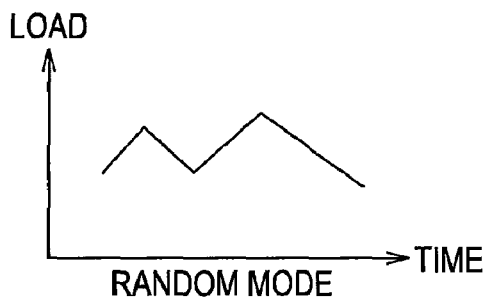
FIG. 26B illustrates an example of a replay music list (random mode) as a list of music data to be reproduced.

FIG. 26A illustrates an automatically generated replay music list 3. The audio reproducing apparatus of the second embodiment generates the replay music list 3 for the random mode based on the acquired personal profile information and exercise information. In the random mode as shown in FIG. 26B, the load of exercise varies randomly with time.

The replay music list 3 of FIG. 26A is generated from the replay music information of FIG. 23, and lists six songs of the song A (length: 1 minute and 11 seconds, and tempo: 100), the song B (length: 2 minutes and 22 seconds, and tempo: 120), the song C (length: 3 minutes and 33 seconds, and tempo: 105), the song E (length: 1 minute and 50 seconds, and tempo: 180), and the song F (length: 3 minutes and 00 second, and tempo: 80). The replay music list 3 thus commands that five plays of the song A, five plays of the song E, three plays of the song C, ten plays of the song E, five plays of the song B, and one play of the song F be reproduced in that order. The replay music list 3 thus allows the user to exercise for a total time of about 80 minutes.

As shown in FIGS. 24A-26B, the audio reproducing apparatus of the second embodiment automatically generates the plurality of replay music lists based on the acquired personal profile information and exercise information in accordance with the plurality of exercise modes, and store the replay music lists on a predetermined recording medium or memory, and then displays the replay music lists to be indicated to the user in step S404 of FIG. 22. The replay music list may be generated in step S404 or earlier step shown in FIG. 22.

A replay music list prepared in advance (pre-registered), or a preset replay music list is described below. FIGS. 27A and 27B illustrate an example of the preset replay music list. The user who exercises to the song reproduced by the audio reproducing apparatus of the second embodiment pre-registers the preset replay music list adapted to the user's own usage or preference.

As shown in FIG. 27A, a user, who frequently walks for 30 minutes, may prepare in advance a replay music list 1 preset for walking exercise of 30 minutes. The user exercises to the music data reproduced from the replay music list 1. As shown in FIG. 27A, the replay music list 1 lists five songs of a song A (length: 1 minute and 11 seconds, and tempo: 100), a song B (length: 2 minutes and 22 seconds, and tempo: 120), a song C (length: 3 minutes and 33 seconds, and tempo: 105), a song G (length: 2 minutes and 00 second, and tempo: 100), and a song I (length: 2 minutes and 00 second, and tempo: 100). The replay music list 1 thus commands that two plays of the song A, three plays of the song B, three plays of the song C, three plays of the song G, and two plays of the song I be reproduced in that order. The replay music list 1 thus allows the songs, each having tempo of about 100, to be reproduced for about 30 minutes, thereby allowing the user to exercise for a total of about 30 minutes in total.

As shown in FIG. 27B, a user, who frequently jogs for 30 minutes, may prepare in advance a replay music list 2 preset for jogging exercise of 30 minutes. The user exercises to the music data reproduced from the replay music list 2. As shown in FIG. 27B, the replay music list 1 lists four songs of a song B (length: 2 minutes and 22 seconds, and tempo: 120), a song D (length: 2 minutes and 30 seconds, and tempo: 145), a song E (length: 1 minute and 50 seconds, and tempo: 180), and a song H (length: 3 minutes and 30 seconds, and tempo: 130). The replay music list 1 thus commands that two plays of the song B, two plays of the song D, two plays of the song E, two plays of the song D, two plays of the song H, and two plays of the song B be reproduced in that order. The replay music list 2 thus allows the songs, each having tempo of 120 or more, to be reproduced for about 30 minutes, thereby allowing the user to exercise for a total time of about 30 minutes.

As the audio reproducing apparatus of the first embodiment, the audio reproducing apparatus of the second embodiment inputs the music data to be reproduced and the number of plays of the music data in accordance with the replay music information of FIG. 23 as a list of the music data replayable on own apparatus, thereby setting the preset replay music list and storing the preset replay music list on a predetermined recording medium.

The plurality of replay music lists discussed with reference to FIGS. 24A-27B are stored on one of the storage unit 53 and the RAM 13, and then supplied to the display circuit 33 under the control of the controller 10. The display circuit 33 displays the replay music lists on the display screen of the display 34 as a replay music candidate list.

FIGS. 28A and 28B illustrate a specific example of the replay music candidate list when a plurality of replay music lists are displayed to the user. For example, as shown in FIG. 28A, a label appears on the top portion of the display screen 34G of the display 34 to indicate that the information displayed is a replay music candidate list. Usable replay music lists are displayed in a list below the label.

Listed here are a title of usable replay music list, such as a title name "list 1 (hill mode)," a title of the music data forming the replay music list, length, song tempo, and the number of plays. If all music lists cannot be accommodated in the display screen 34G of the display 34, the display screen is scrolled to view all lists.

When a desired replay music list is found, the user operates the keyboard 41, and performs an entering operation with a cursor placed on a predetermined location such as the title name of the desired replay music list. The desired replay music list is thus ready to be actually used.

FIG. 28B illustrates a list of title names of the replay music lists: "list 1 (hill mode)," "list 2 (constant mode)," "list 3 (random mode)," "preset list 1 (walking exercise of 30 minutes)" and "preset list 2 (jogging exercise of 30 minutes)." The content of a replay music list selected from those lists is displayed for determination and re-selection.

FIGS. 28A and 28B illustrate examples of the replay music candidate lists. A variety of forms are also possible. For example, the titles and content of the usable replay music list are displayed on a screen on a per replay music list basis. When a page turning command is input to the keyboard 41, another usable replay music list may be displayed.

The music data is selected and reproduced in step S408 of FIG. 22 based on the replay music list selected in steps S404 through S407 of FIG. 22.

Modifying the Content of the Replay Music List

As discussed with reference to step S405 of FIG. 22, the audio reproducing apparatus of the second embodiment can modify the content of the selected replay music list. FIG. 29 illustrates how the audio reproducing apparatus of the second embodiment modifies the content of the replay music list.

Portion A of FIG. 29 illustrates a selected replay music list to be modified, and portions B and C of FIG. 29 respectively illustrate modified replay music lists. As shown in the portion A of FIG. 29, a replay music list 3 (random mode) might be selected from the usable replay music lists.

The controller 10 controls the display circuit 33, thereby displaying the content of the selected replay music list 3 on the display screen 34G of the display 34, and is ready to receive a content modification input from the user. For example, if a song G in the replay music list (random mode)

displayed in the portion A of FIG. 29 fails to appeal to the user, the song B can be replaced with the song I as shown in the portion B of FIG. 29.

More specifically, a cursor is placed on a display area of the title of the music data to be replaced or the characteristic information by operating an operation key such as an arrow key on the keyboard 41, and another usable song may be specified. As shown in the portion B of FIG. 29, the song G is thus replaced with the song I in the replay music list 3.

By repeating such operations, a series of modification steps may be performed, for example, the music data to be reproduced is replaced, the play order of the music data to be reproduced is modified, and the number of plays of the music data to be reproduced is modified as shown in the portion C of FIG. 29. The content of the usable replay music list thus remains modifiable. The user can modify the content of the automatically generated replay music list or the preset replay music list to the user's personal usage or preference. The user can thus arrange the existing replay music list to the user's own usage or preference, and reproduces the music data using the arranged replay music list.

Specific Example of Exercise Amount Display

In accordance with the second embodiment the exercise amount calculated in step S411 of FIG. 22 is displayed on the display screen of the display 34 to be indicated to the user. As the audio reproducing apparatus of the first embodiment as described with reference to FIG. 16, the audio reproducing apparatus of the second embodiment displays in step S412 the information regarding the exercise time, the number of steps, the distance walked, the average speed, the calories consumed, and the fat burned.

The three modes, namely, the hill mode, the constant mode and the random mode, are described as the usable modes. Another mode may be defined and then used.

Figure 30:
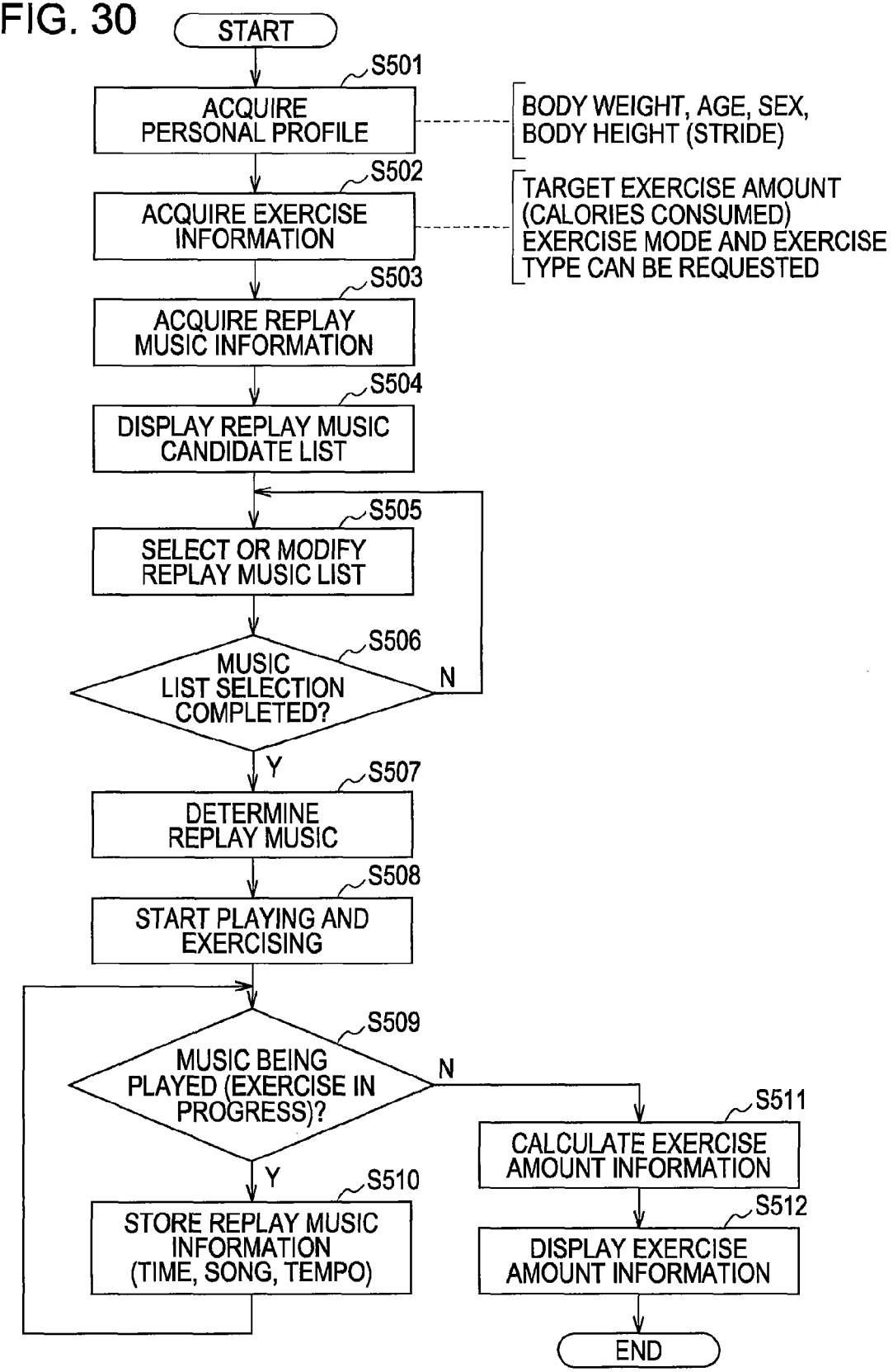
FIG. 30 is a flowchart illustrating another process in which the audio data to be reproduced from a predetermined amount of exercise is selected, determined, and reproduced.

Reproducing the Music Data Using the Replay Music List Automatically Generated from the Target Exercise Amount and the Pre-Registered Replay Music List The music data is reproduced using the replay music list automatically generated from the target exercise amount and the pre-registered replay music list. FIG. 30 is a flowchart illustrating a process of the audio reproducing apparatus of the second embodiment. The audio reproducing apparatus of the second embodiment selects and determines a replay music list to be used, based on an input target exercise amount, and calculates an exercise amount using the characteristic information of the reproduced music data. The process of FIG. 30 is also executed by the controller 10 in the audio reproducing apparatus of the second embodiment.

The controller 10 in the audio reproducing apparatus of the second embodiment receives via the keyboard 41 the key input personal profile information required to calculate, the exercise amount of the user, including the body weight, the body height (stride), the age, and the sex of the user, and stores the personal profile information on the RAM 13 (step S501). The information such as the body weight and the body height is needed to calculate the amount of exercise, such as the calories consumed and the distance walked (exercise distance), and the information such as the age and the sex is needed to be displayed at the end of the exercise. The controller 10 in the audio reproducing apparatus receives key input information indicating the target energy (target exercise amount) of the exercise the user is going to consume in the exercise, and then stores the information on the RAM 13 (step S502). In step S502, the user can also input one of the exercise modes the user is going to practice, such as the hill mode, the constant mode, or the random mode, and the type (category) of the exercise the user is going to practice, such as walking, jogging, running, dash, strolling, etc.

The exercise information acquired by the controller 10 in the audio reproducing apparatus in step S502 is used to generate automatically the replay music list as will be described in detail later.

The controller 10 in the audio reproducing apparatus then acquires the characteristic information, such as the title, the play time, and the tempo of the replayable music data, and the consumed energy and exercise distance of travel (step S503). The characteristic information such as the title, the play time, the tempo, the consumed energy and the exercise distance of travel is determined a per music (song) basis.

The consumed energy indicates an amount of energy consumed by the player (user) who has exercised to the music output in response to the playing of the music data. The distance of travel in the exercise indicates a distance along which the player (user) has exercised to the music output in response to the playing of the music data. A plurality of different values may be set as each of the consumed energy and the exercise distance of travel of the user in response to the intensity of the exercise.

As previously discussed with reference to step S403 of FIG. 22, the audio reproducing apparatus of the second embodiment may acquire the characteristic information containing the title, the play time, the tempo and the consumed energy relating to the replayable music data in step S503. The audio reproducing apparatus of the second embodiment reads and acquires the characteristic information from the recording medium of the music information storage unit 21. Alternatively, the audio reproducing apparatus of the second embodiment may be connected to a network via the communication I/F 61, and may acquire the characteristic information from a database in a server over the network.

To acquire from the database over the network the title and the characteristic information of the replayable music data, the audio reproducing apparatus may search for and acquire the title and the characteristic information according to the identification information of the replayable music data. The replayable music data to be stored on the recording medium of the music information storage unit 21 may be acquired from a medium such as CD (Compact Disk), or from a database over a network via.

The replay music information composed of the title and the characteristic information of the acquired replayable music is temporarily stored on the RAM 13 to be used by the audio reproducing apparatus of the second embodiment. The replay music information of FIG. 23 is generated on the recording medium of the music information storage unit 21 and read and stored temporarily onto the RAM 13.

Figures 31, 32A, 32B:
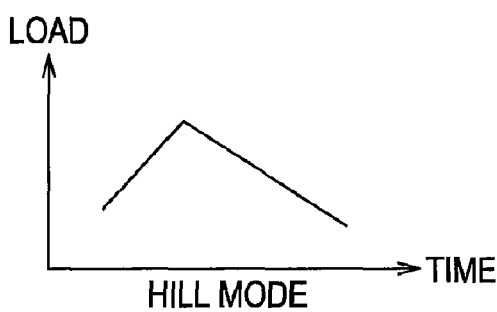
FIG. 31 illustrates an example of the replay music list as a list of the music data to be reproduced.
FIG. 32A illustrates an automatically generated replay music list (hill mode).
FIG. 32B illustrates an automatically generated replay music list (hiii mode).

FIG. 31 illustrates an example of a list of the usable music data acquired in step S503 (replay music information). The list of FIG. 31 includes the title of the replayable music data, the length of the music reproduced in response to the music data (play time), the tempo of the replayable music data, and the energy consumed when the user has exercised to the music reproduced in response to the music data from beginning to end.

The replay music information of FIG. 31 composed of the title and the characteristic information of the acquired replayable music is stored temporarily on the RAM 13 and then used. As shown in FIG. 23, the replay music information is generated on the recording medium of the music information storage unit 21 and then read and stored temporarily the RAM 13 to be used.

The controller 10 in the audio reproducing apparatus of the second embodiment controls the display circuit 33 to display the replay music list. The display circuit 33 displays on the display 34 as the replay music list the replay music list automatically generated using the replay music information of FIG. 31 and the prepared replay music list to be indicated to the user (step S504).

As will be described more in detail later, the replay music candidate list displayed in step S504 may be a replay music list automatically generated as shown in FIGS. 32A-35B driven by the target exercise amount in accordance with the exercise mode, or the replay music candidate list displayed in step S504 may be a prepared (pre-registered) replay music list shown in FIG. 36.

The usable replay music list is stored on the recording medium of the music information storage unit 21, or the recording medium of the storage unit 53 or a non-volatile memory such as an EEPROM not shown in FIG. 1. The usable replay music list may be displayed on the display screen of the display 34 as shown in FIGS. 28A and 28B. Replay music candidate lists may thus be displayed with all lists at a time or with one list by one list successively.

The controller 10 receives via the keyboard 41 one of a selection input of the replay music list and a modification input to the selected replay music list entered by the user (step S505), and determines whether the input operation of one of the selection input of the replay music list and the modification input to the selected replay music list is completed (step S506).

If it is determined in the determination step S506 that the input operation of the user has not been completed, processing returns to step S505. If it is determined in determination step S506 that the input operation of the user has been completed, the controller 10 determines, as a replay music list to be used, one of the selected replay music list and the selected and then modified replay music list (step S507).

In accordance with the replay music list determined in step S507, the controller 10 performs a series of reproducing steps, namely, successively reads the music data to be reproduced from the recording medium of the music information storage unit 21, supplies the read music data to the audio signal output processor 31, and causes a sound responsive to the read music data to be emitted from the loudspeaker (step S508). In step with (in synchronization with) the thus reproduced music, the user starts playing exercise.

The controller 10 monitors the processing state of own apparatus, thereby determining whether the music playing is in progress (step S509). If it is determined in the determination step S509 that the music playing is in progress, the storage unit 53 stores the information (replay music information) regarding the title, the play time, and the tempo of the music data now being reproduced as the play history information (step S510). Processing returns to step S509 for repeating the above described process.

If it is determined the determination step S509 that the playing of the music data has been completed, the controller 10 controls the exercise information analyzer circuit 23 to calculate the amount of exercise practiced by the user (step S511). More specifically, the exercise information analyzer circuit 23 calculates the amount of exercise based on the play history information recorded on the recording medium of the storage unit 53 in step S510, the personal profile information composed of the body weight, the body height, the age and the sex of the user and the exercise information acquired and then temporarily stored on the RAM 13 in steps S501 and S502. As the audio reproducing apparatus of the first embodiment discussed with reference to FIGS. 6-14, the audio reproducing apparatus of the second embodiment calculates the amount of exercise practiced by the user in step S511.

The controller 10 controls the display circuit 33, thereby displaying the information indicating the amount of exercise of the user determined in step S511 on the display screen of the display 34 (step S512). The process of FIG. 30 thus ends. As the audio reproducing apparatus of the first embodiment, as will be also described later, the audio reproducing apparatus of the second embodiment notifies the user of the amount of exercise of the user in step S512 in the form displayed in FIG. 38.

Specific Example of the Replay Music List

A specific example of the replay music list indicated to the user in step S504 of FIG. 30 and display examples thereof are described with reference to FIGS. 32A-36. In step S504 of FIG. 30 as previously discussed, a plurality of usable replay music lists such as the automatically generated replay music list and the replay music list prepared in advance are displayed on the display screen of the display 34 to be indicated to the user.

FIGS. 32A-35B illustrate the replay music lists that are automatically generated from the play history information of FIG. 31 by the audio reproducing apparatus of the second embodiment. The audio reproducing apparatus of the second embodiment generates the replay music list based on the personal profile information acquired in step S501 and the exercise information (the target exercise amount (consumed calories)) acquired in step S502 as shown in FIG. 30. FIG. 36 illustrates an example of the replay music list prepared in advance.

The replay music list automatically generated based on the personal profile information and exercise information is described. The personal profile information is used to prevent an excess load from being put on the user, in other words, used to limit available tempo or total play time of the music data corresponding to the time throughout which the user practices exercise. The target exercise amount serves as a target value that the user intends to achieve when the user exercises in accordance with the replay music list.

In step S504 of FIG. 30, as in step S404 of FIG. 22, the audio reproducing apparatus automatically generates a plurality of usable replay music lists based on the acquired personal profile information and the target exercise amount of the user in view of the exercise modes such as the hill mode, the constant mode, and the random mode.

FIG. 32A illustrates an automatically generated replay music list 1. The audio reproducing apparatus of the second embodiment generates the replay music list 1 for the hill mode based on the acquired personal profile information and target exercise amount. In the hill mode as shown in FIG. 32B, the load of exercise gradually increases with time to a predetermined level, and after reaching the predetermined level, the load of the exercise gradually decreases.

The replay music list 1 of FIG. 32A is generated from the replay music list of FIG. 31. The replay music list 1 lists six songs of a song A (length: 1 minute and 11 seconds, tempo: 100, and consumed energy: 10 kcal), a song B (length: 32 minutes and 22 seconds, tempo: 120, and consumed energy: 25 kcal), a song C (length: 3 minutes and 33 seconds, tempo: 105, and consumed energy: 30 kcal), a song D (length: 2 minutes and 30 seconds, tempo: 145, and consumed energy: 35 kcal), a song E (length: 1 minute and 50 seconds, tempo: 180, and consumed energy: 30 kcal), and a song F (length: 3 minutes and 00 second, tempo: 80, and consumed energy: 15 kcal).

The replay music list 1 of FIG. 32A thus commands that five plays of the song A (50 kcal), one play of the song C (30 kcal), one play of the song B (25 kcal), one play of the song D (35 kcal), eight plays of the song E (240 kcal), three plays of the song B (75 kcal), one play of the song C (30 kcal), and one play of the song F (15 kcal) be reproduced in that order. The replay music list 1 thus allows the user to consume a total energy of 500 kcal.

Figure 33B:
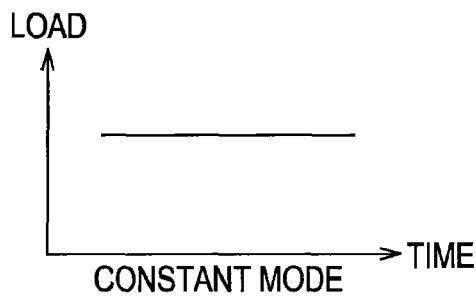
FIG. 33B illustrates an automatically generated replay music list (constant mode).

FIG. 33A illustrates an automatically generated replay music list 2. The audio reproducing apparatus of the second embodiment generates the replay music list 2 for the constant mode based on the acquired personal profile information and exercise information. In the constant mode as shown in FIG. 33B, the load of an exercise, remains constant throughout the exercise.

The replay music list 2 of FIG. 33A is generated from the replay music information of FIG. 31, and indicates 50 consecutive plays of the song A (length: 1 minute and 11 seconds, tempo: 100, and consumed energy: 10 kcal). In accordance with the replay music list 2, the user consumes total heat energy of 500 kcal.

Figure 34B:
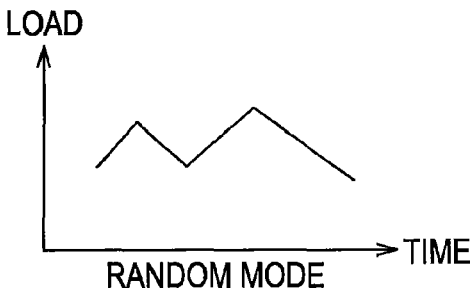
FIG. 34B illustrates an automatically generated replay music list (random mode).

FIG. 34A illustrates an automatically generated replay music list 3. The audio reproducing apparatus of the second embodiment generates the replay music list 3 for the random mode based on the acquired personal profile information and exercise information. In the random mode as shown in FIG. 34B, the load of an exercise varies randomly with time.

The replay music list 3 of FIG. 34A is generated from the replay music information of FIG. 31, and lists 45 songs of the song A (length: 1 minute and 11 seconds, tempo: 100, and consumed energy: 10 kcal), the song B (length: 2 minutes and 22 seconds, tempo: 120, and consumed energy: 25 kcal), the song C (length: 3 minutes and 33 seconds, tempo: 105, and consumed energy: 30 kcal), the song E (length: 1 minute and 50 seconds, tempo: 180, and consumed energy: 30 kcal), and the song F (length: 3 minutes and 00 second, tempo: 80, and consumed energy: 15 kcal). The replay music list 3 thus commands that three plays of the song A (30 kcal), three plays of the song E (90 kcal), three plays of the song C (90 kcal), five plays of the song E (150 kcal), five plays of the song B (125 kcal), and one play of the song F (15 kcal) be reproduced in that order. The replay music list 3 thus allows the user to consume total heat energy of 500 kcal.

Figures 35A, 35B, 36:
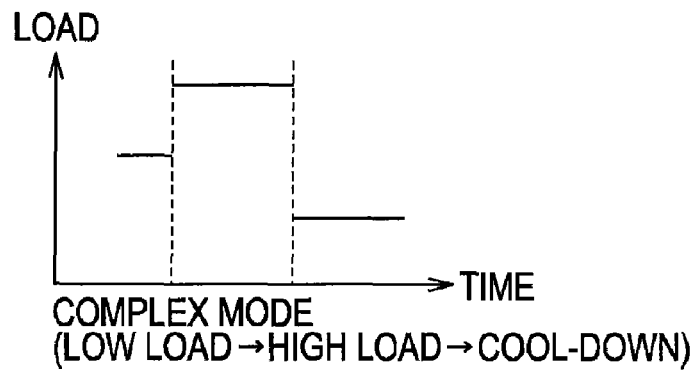
FIG. 35A illustrates an automatically generated replay music list (complex mode).
FIG. 35B illustrates an automatically generated replay music list (complex mode).
FIG. 36 illustrates a preset replay music list.

FIG. 35A illustrates an automatically generated replay music list 4. The audio reproducing apparatus of the second embodiment generates the replay music list 4 for the complex mode based on the acquired personal profile information and exercise information. In the complex mode as shown in FIG. 35B, the user exercises with different loads, for example, a light load exercise, then a heavy load exercise for a constant period of time, and then again a light load exercise for a predetermined period of time for cool-down.

The replay music list 4 of FIG. 35A is generated from the replay music information of FIG. 31, and lists 3 songs of the song B (length: 2 minutes and 22 seconds, tempo: 120, and consumed energy: 25 kcal), the song E (length: 1 minute and 50 seconds, tempo: 180, and consumed energy: 30 kcal), and the song F (length: 3 minutes and 00 second, tempo: 80, and consumed energy: 15 kcal). The replay music list 4 thus commands that live plays of the song B (125 kcal), ten plays of the song E (300 kcal), and five plays of the song F (75 kcal) be reproduced in that order. The replay music list 4 thus allows the user to consume total heat energy of 500 kcal.

As shown in FIGS. 32A-35B, the audio reproducing apparatus of the second embodiment automatically generates the plurality of replay music lists based on the acquired personal profile information and exercise information in accordance with the plurality of exercise modes. The replay music list may be automatically generated in step S504 or earlier step shown in FIG. 30.

A replay music list prepared in advance (pre-registered), or a preset replay music list is described below. FIG. 36 illustrates an example of the preset replay music list. The user who exercises to the song reproduced by the audio reproducing apparatus of the second embodiment pre-registers the preset replay music list adapted to the user's own usage or preference.

As shown in FIG. 36, a user may prepare in advance a replay music list for consuming heat energy of 500 kcal in the random mode as the exercise mode. Using the replay music list, the user may exercise to the reproduced music data. As shown in FIG. 36, the preset replay music list lists five songs of a song A (length: 1 minute and 11 seconds, tempo: 100, and consumed energy: 10 kcal), a song B (length: 2 minutes and 22 seconds, tempo: 120, and consumed energy: 25 kcal), a song C (length: 3 minutes and 33 seconds, tempo: 105, and consumed energy: 30 kcal), a song E (length: 1 minute and 50 seconds, tempo: 180, and consumed energy: 30 kcal), and a song F (length: 3 minutes and 00 second, tempo: 80). The preset replay music list thus commands that five plays of the song A (50 kcal), two plays of the song E (60 kcal), three plays of the song C (90 kcal), seven plays of the song E (210 kcal), three plays of the song B (75 kcal) and one play of the song F (80 kcal) be reproduced in that order. The preset replay music list thus allows the user to consume heat energy of 500 kcal in the random mode.

The plurality of replay music lists discussed with reference to FIGS. 32A through 36 is stored on one of the storage unit 53 and the RAM 13, and then supplied to the display circuit 33 via the controller 10. The display circuit 33 displays the replay music lists as replay music candidate lists on the display screen of the display 34. For example, as shown in FIG. 28A, a label appears on the top portion of the display screen 34G of the display 34 to indicate the information displayed is a replay music candidate list. A usable replay music list is displayed below the label.

Listed here are a title name of each usable replay music list such as "list 1 (hill mode)," a title of the music data forming the replay music list, length, song tempo, and the number of plays. If all replay music lists cannot be accommodated in the display screen 34G of the display 34, the display screen is scrolled to view all lists.

When a desired replay music list is found, the user operates the keyboard 41, and performs an entering operation with a cursor placed on a predetermined location such as the title name of the desired replay music list. The desired replay music list is thus ready to be actually used.

FIG. 28B illustrates the list of title names of the replay music lists: "list 1 (hill mode)," "list 2 (constant mode)," "list 3 (random mode)," "preset list 1 (walking exercise of 30 minutes)." The content of a replay music list selected from those lists is displayed for determination and re-selection. Another display form may also be used.

The music data is selected and reproduced in step S508 in accordance with the replay music list selected in steps S504 through S507 of FIG. 30.

Modifying the Content of the Replay Music List

As discussed with reference to step S505 of FIG. 30, the audio reproducing apparatus of the second embodiment can modify the content of the selected replay music list. FIG. 37 illustrates how the audio reproducing apparatus of the second embodiment modifies the content of the replay music list.

Portion A of FIG. 37 illustrates a selected replay music list to be modified, and portion B of FIG. 37 illustrates a modified replay music list. As shown in the portion A of FIG. 37, a replay music list 3 (random mode) might be selected from the usable replay music lists.

The controller 10 controls the display circuit 33, thereby displaying the content of the selected replay music list 3 on the display screen 34G of the display 34, and is ready to receive a content modification input from the user. For example, a third song may be changed from a song C to a song H in the replay music list (random mode) displayed in the portion A of FIG. 37.

More specifically, a cursor is placed on a display area of the title of the music data to be replaced or the characteristic information by operating an operation key such as an arrow key on the keyboard 41, and another usable song may be specified. As shown in the portion B of FIG. 37, the third song is changed from the song B to the song H.

By repeating such operations, a series of modification steps may be performed, for example, the music data to be reproduced is replaced, the play order of the music data to be reproduced is modified, and the number of plays of the music data to be reproduced is modified. The content of the usable replay music list thus remains modifiable. The user can modify the content of the automatically generated replay music list or the preset replay music list to the user's personal usage or preference. The user can arrange the existing replay music list to the user's own usage or preference, and thus reproduces the music data, using the arranged replay music list.

Specific Example of Exercise Amount Display

In the process FIG. 30, the exercise amount calculated in step S511 is displayed on the display screen of the display 34 to be indicated to the user. In step 512 as shown in FIG. 38, the audio reproducing apparatus of the second embodiment displays the information regarding the target consumed calories, the exercise time, the distance walked, the average speed, the calories consumed, and the fat burned.

When the replay music list is automatically generated taking into consideration the target exercise amount discussed with reference to FIGS. 30-38, the available exercise modes are the hill mode, the constant mode, the random mode, and the complex mode discussed with reference to FIGS. 35A and 35B. The complex mode is used not only when the replay music list is automatically generated driven by the target exercise amount but also when the replay music list is automatically generated based on the personal profile information and the exercise information discussed with reference to FIGS. 22-29.

The hill mode, the constant mode, the random mode, the complex mode, a combination thereof, or any other new mode may be used regardless of when the replay music list is automatically generated based on the personal profile information and the exercise information discussed with reference to FIGS. 22-29 or when the replay music list is automatically generated in view of the target exercise amount discussed with reference to FIGS. 30-38.

The audio reproducing apparatus of the second embodiment is thus designed to use a plurality of replay music lists including the automatically generated replay music list and the pre-registered replay music list. The user is thus freed from entering a command to select a plurality of replay music lists to be reproduced before starting exercising.

By selecting a replay music list appropriate for exercise the user is going to practice, the user reproduces a series of music data and is guided to the exercise. The user can play target exercise comfortably and reliably.

If the music data of the replay music list to be used is partially inappropriate for the exercise, or is not preferred by the user, the user can modify the replay music list. The user can rearrange the replay music list into a replay music list satisfying the user's usage and preference and then actually uses the modified replay music list.

As the audio reproducing apparatus of the first embodiment, the audio reproducing apparatus of the second embodiment indicates to the user the exercise amount information of the exercise practiced by the user. The audio reproducing apparatus of the second embodiment motivates the user to play sports and allows the user to play comfortably on a regular basis the exercise that possibly needs to be performed on a regular basis. Since the play history information, the personal profile information, and the exercise amount information can be managed by the user's own audio reproducing apparatus, the personal information of the user is securely managed.

The audio reproducing apparatus of the second embodiment also includes the storage unit 53. As previously discussed, the personal profile information, the exercise amount information and the replay music information, etc., may be stored the storage unit 53 and then retrieved later for a variety of analyses.

By inputting information such as the target consumed energy, the user can learn the required amount of exercise to achieve the target in terms of the music data to be reproduced and the number of plays with respect to the consumed calories of the reproduced music data. The user reproduces the music data as indicated, and practices walking exercise or jogging exercise to the music reproduced from the music data. When all music data is reproduced by the indicated number of plays, the user completes the exercise, corresponding to the target consumed calories. By simply exercising to the reproduced music, the user can play the exercise of the target amount.

The audio reproducing apparatus of the present invention is relatively easily implemented by producing the program executing the processes discussed with reference to FIGS. 22 and 30 and by loading the program on any of a variety of audio reproducing apparatuses.

In accordance with the second embodiment of the present invention, the controller 10, the display circuit 33 and the display 34 working in cooperation constitute indicating means. The keyboard 41 and the controller 10 working in cooperation constitute selection input receiving means and modification input receiving means, and the controller 10 implements the function of the modifying means.

In accordance with the second embodiment of the present invention, the exercise amount, information and the target, exercise amount information may include the exercise time, the exercise intensity, the exercise distance, and the burned fat amount in addition to the consumed calories. For example, when the exercise time is used as the target exercise amount information, the time throughout which the exercise is desired to be continued (exercise time) is input as the target exercise amount information. The music data is selected to have the play time indicated by the input time information. When the consumed fat amount is input as the target exercise amount information, the music data to be reproduced is selected and determined to burn the input burned fat amount.

When the music data to be reproduced is selected and determined, the type (genre), the tempo, the combination, and the number of plays of the music data to be reproduced may be automatically determined. For example, by attaching information indicating the genre to the characteristic information of the music data, the music data of the genre appropriate for the target exercise amount can be selected. The tempo, the combination, and the number of plays may also be automatically determined based on the target exercise amount.

If the replay music information discussed with reference to FIGS. 23 and 31 contains information regarding the exercise intensity such as the consumed energy for each exercise, a detailed process may be performed on a per exercise basis. The type of exercise may be defined by the type, such as walking, jogging, running, jump rope, and the exercise intensity may be defined by the speed of exercise.

As previously discussed, the replayable music data, may be supplied in the recorded state thereof on a recording medium such as a CD (Compact Disk), an MD (Mini Disc), a card memory, or the like. The recording medium is then loaded on the music information storage unit 21 and the replayable music data is read and reproduced. The replayable music data may be acquired via the communication I/F 61 and the transceiver circuit 62 in communication with a server over a network or a wireless LAN, and then recorded on the recording medium of the music information storage unit 21. The music data may be directly reproduced from an external device connected to the external terminal 51 or the music data from the external device may be recorded on the recording medium of the music information storage unit 21 and then reproduced from the recording medium of the music information storage unit 21.

As described above, the characteristic information of the music data, such as the play time, the tempo, and the consumed calories responsive to the exercise information may be supplied in the recorded state thereof on a recording medium together with the music data. The characteristic information, together with the music data or separately from the music data, may be supplied via a wide area network such as the Internet or a wireless LAN, or from an external device connected to the external terminal 51. The music data and the characteristic information thereof may be separately acquired if the music data and the characteristic information are associated with each other by identification information (ID) of the music data.

The audio reproducing apparatus of the second embodiment is a mobile music reproducing apparatus. More specifically, the audio reproducing apparatus is applicable to a variety of types of apparatuses including a hard disk player, an MD player, and a cellular phone. The present invention is appropriate for use in a mobile apparatus. The audio reproducing apparatus may be used in a stationary fashion. For example, the audio reproducing apparatus may be mounted on a variety of fitness machines for the compact design thereof.

Third Embodiment

The present invention is intended to assist a user who practices walking, jogging, running, or dash exercise, and finds applications in a mobile audio reproducing apparatus carried by the exercising user. The mobile audio reproducing apparatus is available in a variety of sizes and a variety of structures of a keyboard are contemplated.

A third embodiment of the present invention is related to the structure of a user interface related to a mechanism that receives information from the user and indicates information to the user. The user interface includes an external appearance of a mobile audio reproducing apparatus incorporating the present invention, the structure of the keyboard, and a display form of information.

As the audio reproducing apparatuses of the first and second embodiments, the audio reproducing apparatus of the third embodiment is also of a mobile type and the internal structure thereof is identical to the internal structure of the audio reproducing apparatus of the first embodiment discussed with reference to FIG. 1. The audio reproducing apparatus of the third embodiment is discussed also with reference to FIG. 1 on the premise that the audio reproducing apparatus of the third embodiment has the internal structure illustrated in FIG. 1 and that the recording medium thereof is a hard disk or a semiconductor memory.

External Appearance of the Audio Reproducing Apparatus

Figure 39A:
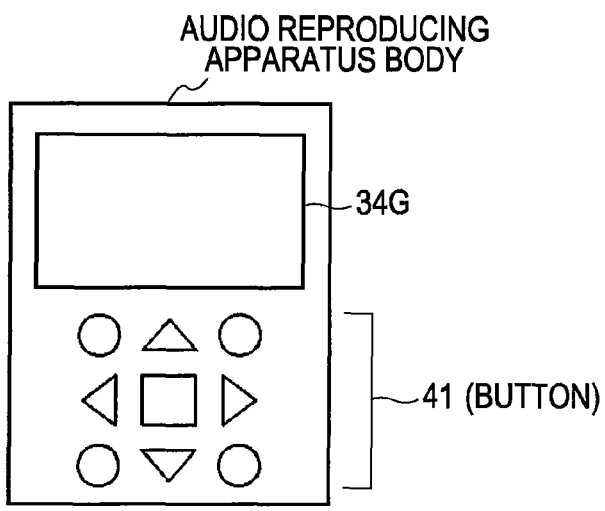
FIG. 39A illustrates a typical external appearance of an audio reproducing apparatus.
Figure 39B:
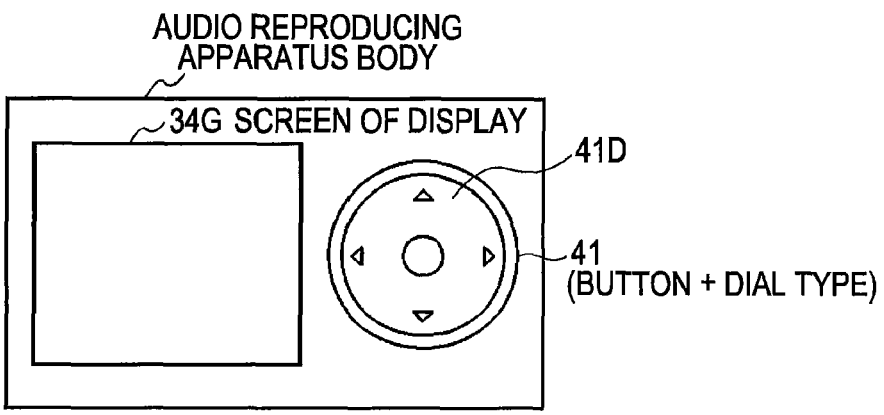
FIG. 39B illustrates a typical external appearance of the audio reproducing apparatus.
Figure 39C:
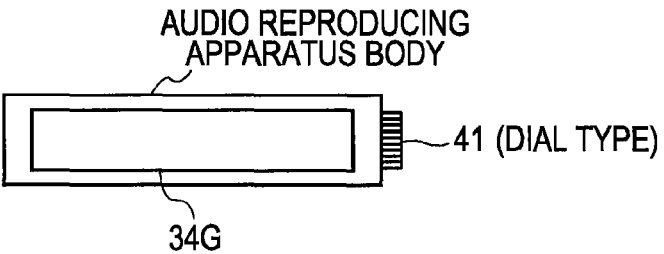
FIG. 39C illustrates a typical external appearance of the audio reproducing apparatus.

FIGS. 39A through 39C illustrate a typical external appearance of the audio reproducing apparatus of the third embodiment. The audio reproducing apparatus of the third embodiment has the palm-size of the user and is small enough to be accommodated in a breast pocket of the user.

The audio reproducing apparatus of the third embodiment has the breast-pocket size of the user at the largest as shown in FIGS. 39A and 39B, and has a size equal to or slightly larger than a stack of several chewing gum sticks as shown in FIG. 39C. With technology advancing, the audio reproducing apparatus can be further miniaturized or light-weighted.

FIGS. 39A and 39B are external views of the audio reproducing apparatus of the third embodiment that is sized to be accommodated in the breast pocket of the user. The audio reproducing apparatus of FIG. 39A is a vertical type with the longitudinal side thereof being aligned with the height direction of the user, and the audio reproducing apparatus of FIG. 39B is a horizontal type with the longitudinal side thereof being aligned in a direction across the body height of the user.

As shown in FIGS. 39A and 39B, a display screen of a display such as LCD and a keyboard are arranged on a surface (front surface) of the audio reproducing apparatus facing the user. As shown in FIG. 39A, the vertical type audio reproducing apparatus includes a display screen 34G of the display 34 and a keyboard 41. The positional relationship of the display screen 34G and the keyboard 41 may be reversed from that shown in FIG. 39A. Alternatively, in the vertical type audio reproducing apparatus, the display screen 34G may be arranged in the center of the front surface of the audio reproducing apparatus and the keyboard 41 may be split, into two sections, one section above the display screen 34G and the other section below the display screen 34G.

As shown in FIG. 39B, the horizontal type audio reproducing apparatus includes the keyboard 41 to the side of the display screen 34G. The positional relationship of the display screen 34G and the keyboard 41 may be reversed from that shown in FIG. 39B. More specifically, if one of the display screen 34G and the keyboard 41 is arranged on the right portion of the front surface of the audio reproducing apparatus, the other is arranged on the left portion of the front surface of the audio reproducing apparatus. Alternatively, in the horizontal type audio reproducing apparatus, the display screen 34G may be arranged in the center of the front surface of the audio reproducing apparatus and the keyboard 41 may be split into two sections, one section to the right of the display screen 34G and the other section to the left of the display screen 34G.

The keyboard 41 may include only "button keys" to be pressed as shown in FIG. 39A. Alternatively, the keyboard 41 may further include a dial 41D. The dial 41D allows the user's finger to slide therealong, and can also be pressed at any position. The dial 41D itself may be constructed of a mechanically rotatable element.

If the audio reproducing apparatus is miniaturized to an extremely small size as shown in FIG. 39C, the keyboard 41 cannot be arranged on the trout surface of the audio reproducing apparatus as shown in FIG. 39B. As shown in FIG. 39C, a rotatable dial may be arranged on one side of the audio reproducing apparatus as the keyboard 41.

The keyboard 41 may be constructed of an operation lever that receives a rotation action and a pressing action, such as a jog dial or a joystick. If the display screen 34G of the display in the audio reproducing apparatus has a relatively large display area as shown in FIGS. 39A and 39B, a touchpanel may be glued on the display screen 34G and information displayed on the display screen 34G and the touchpanel may constitute the keyboard 41.

Using a variety of keyboards discussed with reference to FIGS. 39A through 39C, characters and numbers, such as the name of the user, and symbols are input, a cursor is shifted, and a variety of items is selected. With each character assigned to a respective button key, characters are input with a smaller number of keys. When the dial key is used, a character is selected by sliding the finger of the user along the dial or by rotating the dial, and the selected character is entered by pressing a predetermined key or the dial.

FIGS. 39A through 39C illustrate the external view and the structure of the audio reproducing apparatus. A variety of sizes and appearances of the audio reproducing apparatus, other than those illustrated in FIGS. 39A through 39C may be contemplated. The keyboard is not limited to the one illustrated in FIGS. 39A through 39C. A dial, a jog dial, or a button key may be arranged on the side portion of the audio reproducing apparatus illustrated in FIGS. 39A and 39B. The keyboard may be arranged by combining a button key, a dial, a jog dial, a touchpanel, a joy stick, and a slide operation switch.

Operation of the Audio Reproducing Apparatus

The operation of the audio reproducing apparatus of the third embodiment is described below with reference to a flowcharts of FIGS. 40 and 41. As necessary, the operation of the audio reproducing apparatus of the third embodiment is discussed with reference to FIGS. 42A through 60. An input window and a verification window shown in FIGS. 42A-60 are discussed after the operation of the audio reproducing apparatus of the third embodiment is discussed with reference to FIGS. 40 and 41.

The audio reproducing apparatus of the third embodiment is also identical in structure to the audio reproducing apparatus of the first embodiment discussed with reference to FIG. 1. The third embodiment is also discussed with reference to FIG. 1 because the audio reproducing apparatus of the third embodiment has the same structure as the one illustrated in FIG. 1.

As the audio reproducing apparatus of the second embodiment, the audio reproducing apparatus of the third embodiment has a play mode in which the audio data is reproduced in accordance with one of a replay music list automatically generated using the personal profile information, etc. and a pre-registered replay music list, and a play mode in which the music data is reproduced in accordance with a replay music list automatically generated using the target exercise amount and the pre-registered replay music list. Which mode to use is determined by the user. In the discussion that follows, the two modes for reproducing the music data are separately described.

Figure 40:
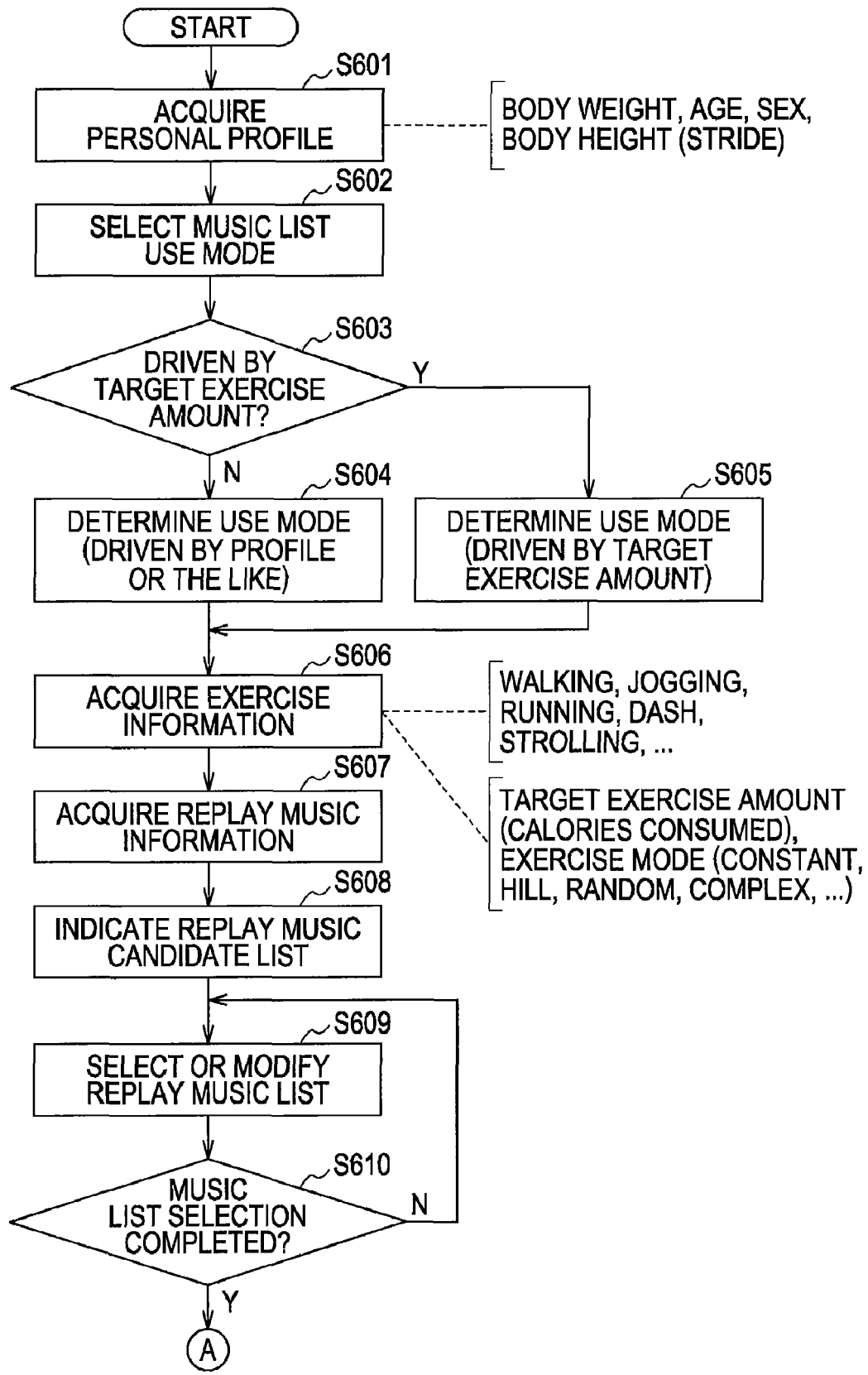
FIG. 40 is a flowchart illustrating another process in which the amount of exercise is determined based on the characteristic information of the reproduced music data.
Figure 41:
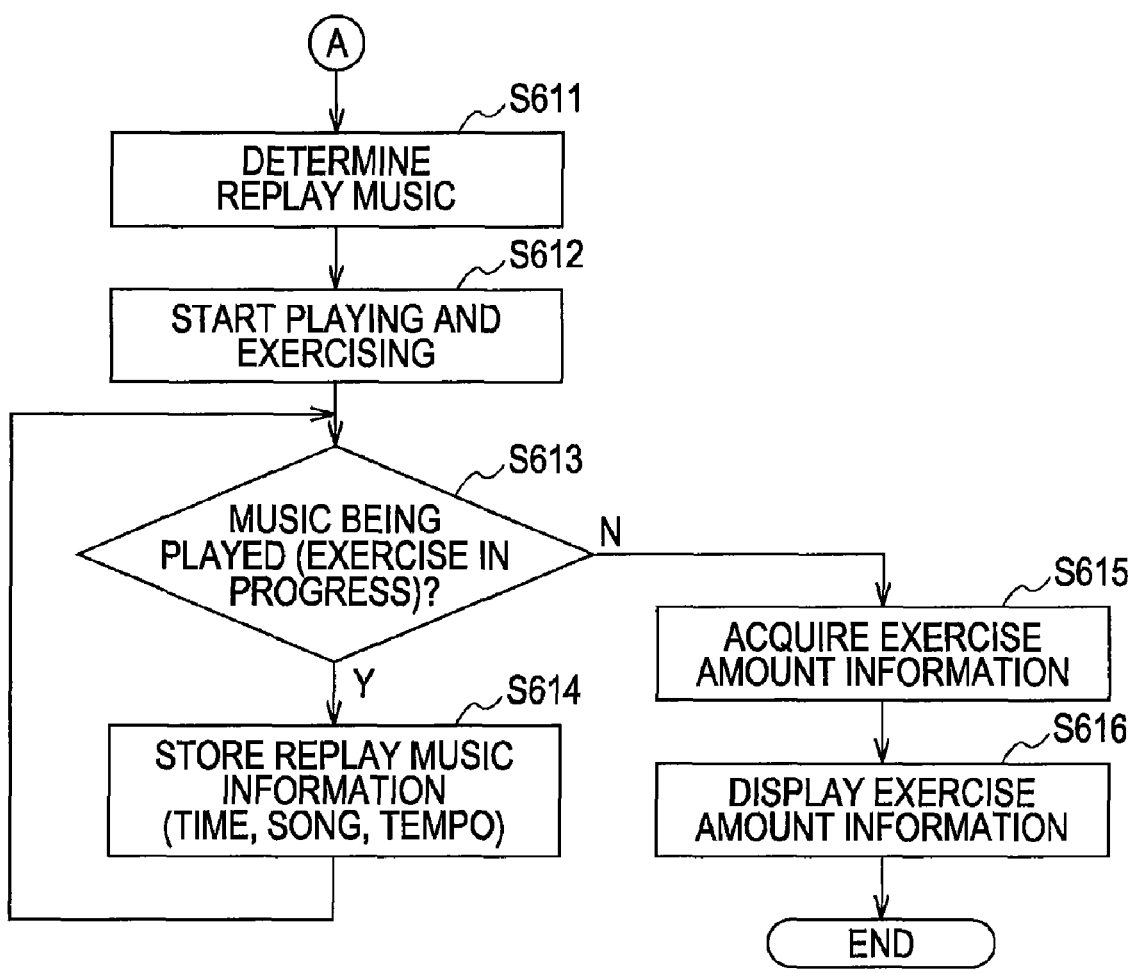
FIG. 41 is a continuation of the flowchart of FIG. 40.

FIGS. 40 and 41 illustrate a control flow in which the exercise amount is determined from the replayable music data when the user exercises using the audio reproducing apparatus of the third embodiment. The process illustrated in FIGS. 40 and 41 is also mainly performed by the controller 10.

The controller 10 in the audio reproducing apparatus of the third embodiment receives the key input personal profile information such as the body weight and the body height (stride) required to calculate the exercise amount input via the keyboard 41 on the input window shown in FIGS. 42A and 42B, and stores the personal profile information on the RAM 13 (step S601).

Figure 43A:
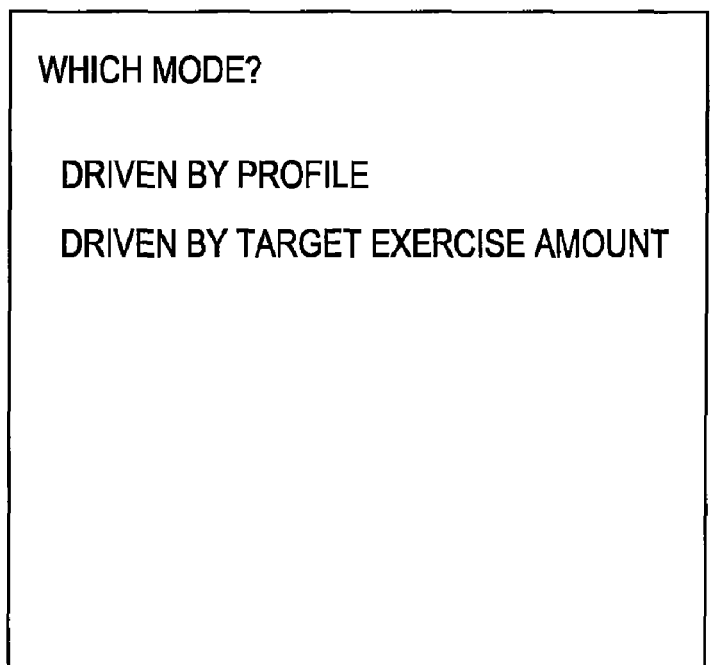
FIG. 43A illustrates an example of an input window and a verification window in a use mode of the replay music list.
Figure 43B:
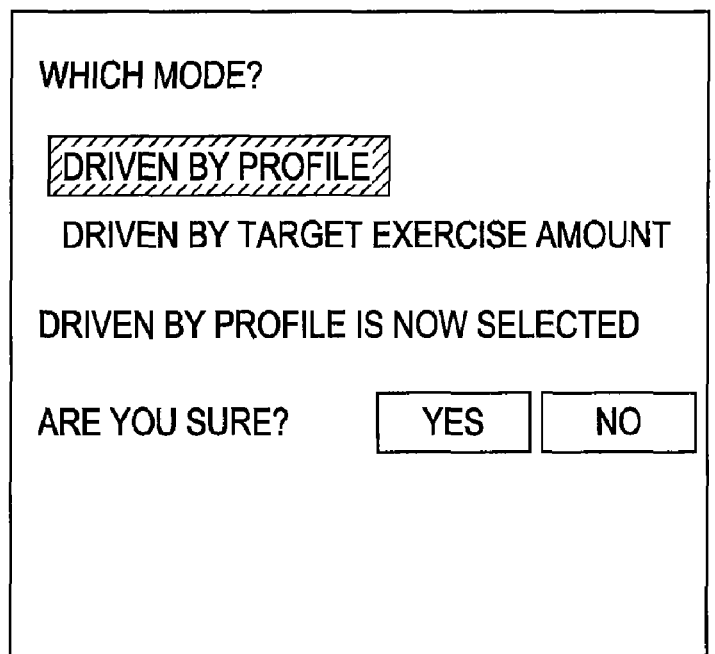
FIG. 43B illustrates an example of the input window and the verification window in a use mode of the replay music list.

The controller 10 in the audio reproducing apparatus receives on the input window of FIGS. 43A and 43B a selection input of a use mode of the replay music list indicating whether to select the play mode in which the audio data is reproduced in accordance with one of a replay music list automatically generated using the personal profile information, etc., or the play mode in which the music data is reproduced using the target exercise amount (step S602). The controller 10 in the audio reproducing apparatus determines whether the mode of generating the replay music list driven by the target exercise amount is selected (step S603).

If it is determined in the determination step S603 that the mode of generating the replay music list driven by the target exercise amount is not selected, the controller 10 determines that the mode of generating the replay music list driven by the personal profile information, etc. is selected. The controller 10 then determines to use the mode of generating the replay music list driven by the personal profile information, etc. (step S604). If it is determined in the determination step S603 that the mode of generating the replay music list driven by the target exercise amount is selected, the controller 10 determines to use the mode of generating the replay music list driven by the target exercise amount (S605).

The controller 10 receives the exercise information input from the user in accordance with the use mode of the replay music list determined in one of steps S604 and S605 (step S606). The process in step S606 is described more specifically. If it is determined in step S604 that the mode of generating the replay music list driven by the personal profile information, etc. is to be used, the controller 10 receives on the input window shown in FIGS. 44A and 44B the key input of information such as the type (category) of exercise the user is going to practice, and then stores the key input information on the RAM 13 in step S606.

If it is determined in step S605 that the mode of generating the replay music list driven by the target exercise amount is to be used, the controller 10 receives on the input window shown in FIGS. 45A and 45B the key input of information such as the target exercise amount, and then stores the key input information on the RAM 13 in step S606. In this case, the exercise mode and the type of the exercise the user is going to practice may be received as necessary.

The controller 10 acquires a list, of replayable music data (replay music information) in accordance with the use mode of the replay music list determined in one of steps S604 and S605 (step S607). If it is determined in step S604 that the mode of generating the replay music list driven by the personal profile information, etc. is to be used, the controller 10 acquires the characteristic information of the music data such as the title, the length (play time), and the tempo of the replayable music data and organizes the characteristic information in a list as shown in FIG. 48 in step S607.

If it is determined in step S605 that the mode of generating the replay music list driven by the target exercise amount, the controller 10 acquires the characteristic information of the music data such as the title, the length (play time), the song tempo, and the consumed energy of the replayable music data and then organizes the characteristic information in a list as shown in FIG. 49 in step S607.

The replay music information shown in FIGS. 48 and 49 is indicated in a list to the user. The audio reproducing apparatus of the third embodiment thus notifies the user what is available as the replayable music data.

As the audio reproducing apparatuses of the first and second embodiments, the audio reproducing apparatus of the third embodiment acquires the replay music information from one of a medium, a database over a network, and an external device connected to the external terminal 51.

Figure 50A:
FIG. 50A illustrates an example of a display screen of an automatically generated replay music list.
Figure 50B:
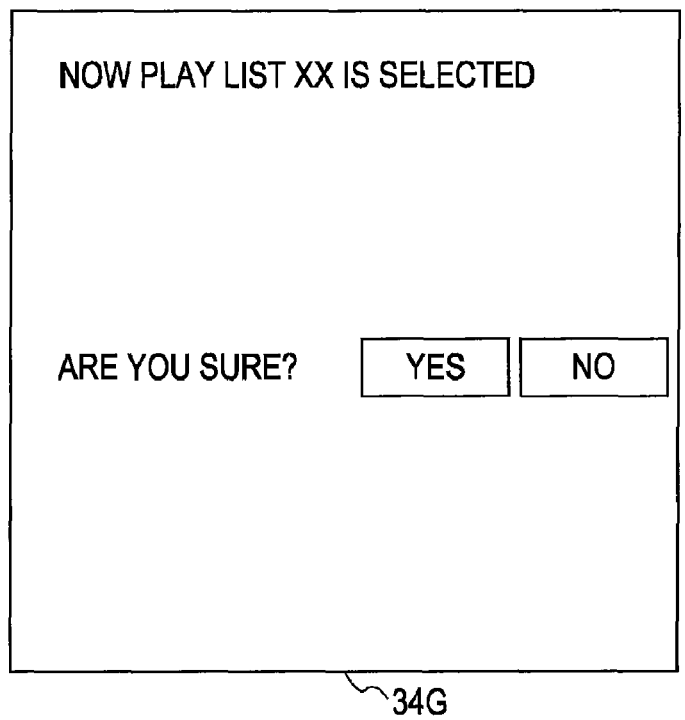
FIG. 50B illustrates an example of the display screen of the automatically generated replay music list.

The controller 10 in the audio reproducing apparatus displays on the display screen 34G of the display 34 the plurality of usable replay music lists automatically generated or pre-registered, to be indicated to the user (step S608). The process in step S608 is described more in detail. If it is determined in step S604 that the mode of generating the replay music list driven by the personal profile information, etc. is to be used, the controller 10 supplies to the display circuit 33 the automatically generated replay music list (referred to as play list) to be displayed on the display screen 34G of the display 34 as shown in FIGS. 50A through 50C or supplies to the display circuit 33 the pre-registered replay music list (referred to as play list) to be displayed on the display screen 34G of the display 34 as shown in FIGS. 51A and 51B.

Figure 57A:
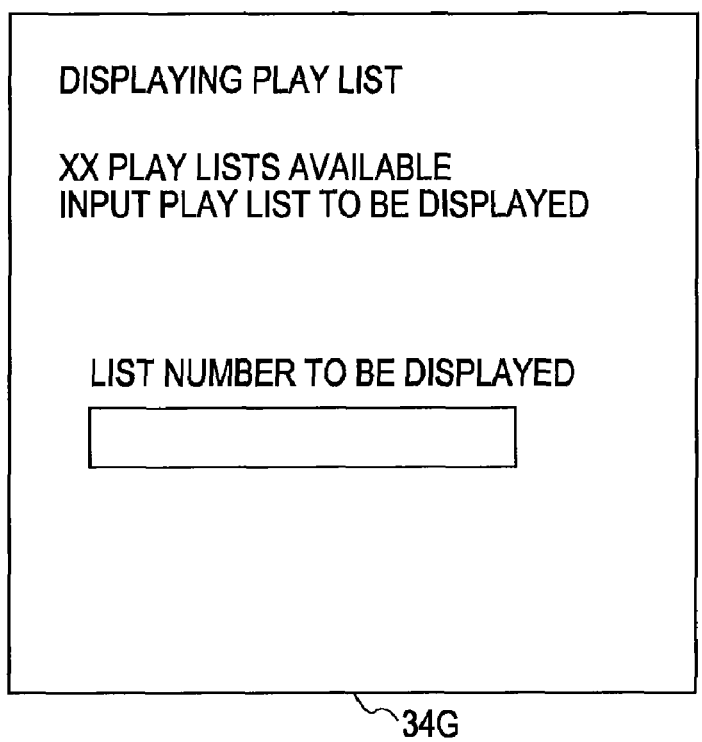
FIG. 57A illustrates a display screen of an automatically generated replay music list.
Figures 57B, 57C:
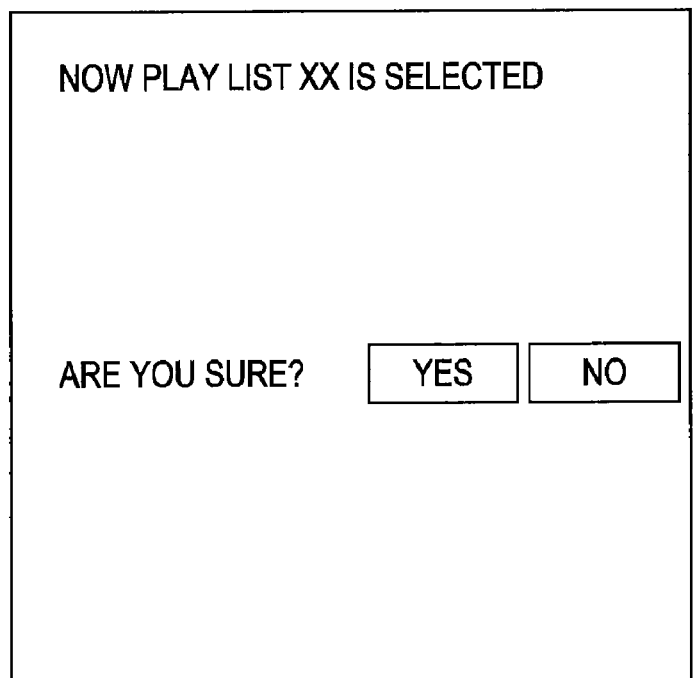
FIG. 57B illustrates a display screen of the automatically generated replay music list.
FIG. 57C illustrates a display screen of the automatically generated replay music list.

If it is determined in step S604 that the mode of generating the replay music list driven by the target exercise amount, is to be used, the controller 10 supplies to the display circuit 33 the automatically generated replay music list (referred to as play list) to be displayed on the display screen 34G of the display 34 as shown in FIGS. 57A through 57C or supplies to the display circuit 33 the pre-registered replay music list (referred to as play list) to be displayed on the display screen 34G of the display 34 as shown in FIGS. 58A and 58B.

The controller 10 selects the replay music list (play list) to be used, and receives a modification to the selected replay music list as shown in FIGS. 56A through 56D and FIGS. 59A through 59D (step S609). The controller 10 determines whether the selection or modification of the replay music list (play list) to be used has been completed (step S610). If it is determined in step S610 that the selection or modification of the replay music list has not been completed, processing returns to step S609.

If it is determined in the determination step S610 that the selection or modification of the replay music list has been completed, the controller 10 proceeds to the process of FIG. 41. The controller 10 determines as a replay music list to be actually used the replay music list (play list) selected or modified in step S610 (step S611), and starts reproducing the music data in accordance with the determined replay music list (step S612). The user thus starts exercise in response to the reproduced music data.

The controller 10 monitors the processing status of own apparatus, and determines whether the playing of the music is in progress (step S613). If it is determined in the determination step S613 that the playing of the music is in progress, the controller 10 stores on the recording medium of the storage unit 53 the information (replay music information) such as the title, the play time, and the tempo of the music data being reproduced (step S614). Processing returns to step S613.

If it is determined in the determination step S613 that the playing of the music data has been completed, the controller 10 controls the exercise information analyzer circuit 23 to calculate the amount of the exercise practiced by the user. More specifically, the exercise information analyzer circuit 23 calculates the amount of the exercise practiced by the user based on the play history information stored on the recording medium of the storage unit 53 in step S614, and the personal profile information regarding the body weight, the body height, the age and the sex of the user and the exercise information acquired and then temporarily stored on the RAM 13 in steps S601 and S606 (step S615). As the audio reproducing apparatus of the first embodiment, the audio reproducing apparatus of the third embodiment calculates the amount of the exercise practiced by the user in step S615 as previously discussed with reference to FIGS. 6-14.

The controller 10 controls the display circuit 33, thereby displaying information regarding the amount of the exercise of the user determined in step S615 on the display screen of the display 34 (step S616). The process of FIGS. 40 and 41 is thus completed. In step S616, the audio reproducing apparatus indicates to the user the amount of the exercise of the user in the form discussed with reference to FIGS. 16 and 20 in connection with the first embodiment.

Specific Example of Input Window

The input window for use in the process discussed with reference to FIGS. 40 and 41 is described in detail.

Input Window of the Personal Profile Information

FIGS. 42A and 42B illustrate an example of the input window and the verification window of the personal profile information for use in step S601 of FIG. 40. In the process of FIG. 40, the controller 10 controls the display circuit 33 in step S601, thereby displaying the input window of the personal profile information of FIG. 42A on the display screen 34G of the display 34. The controller 10 receives information input via the keyboard 41.

The input window of the personal profile information display of FIG. 42A includes input boxes for the name, the sex, the age, the body height and the body weight of the user. The user can enter information to the input boxes using the keyboard 41. When the name, the sex, the age, the body height, and the body weight of the user are input the controller 10 controls the display circuit 33 to display the verification window with the information input on the display screen 34G as shown in FIG. 42B. "YES" and "NO" icons to receive a verification input as to whether the input information is correct or not are displayed on the lower portion of the display screen 34G.

The controller 10 may determine a measure of obesity indicating a body mass index (BMI) that is determined by squaring the quotient that is determined by dividing the body weight by the body height. The verification window of FIG. 42A may further display the BMI.

If the "YES" icon is selected on the verification window of FIG. 42B, the audio reproducing apparatus acquires the input information as the personal profile information, and then stores the personal profile information on the RAM 13. If the "NO" icon is selected, the controller 10 controls the display circuit 33, thereby displaying the input window of FIG. 42A again to receive a modification or a correction to the input information.

Input Window of Use Mode of the Replay Music List

FIGS. 43A and 43B illustrate an input window and a verification window in the use mode of the replay music list for use in step S602 of FIG. 40. In step S602 of FIG. 40, as shown in FIG. 43A, the controller 10 displays a label "DRIVEN BY PROFILE, ETC." for selecting the mode of generating the replay music list driven by the personal profile information, etc. and a label "DRIVEN BY TARGET EXERCISE AMOUNT" for selecting the mode of generating the replay music list driven by the target, exercise amount. The user moves the cursor using the keyboard 41, thereby placing the cursor to one of the labels and performing a predetermined operation. One of the two modes is thus selected.

When one of the two labels "DRIVEN BY PROFILE, ETC." and "DRIVEN BY TARGET EXERCISE AMOUNT" is selected, the audio reproducing apparatus shifts to the verification window to display a "YES" icon and a "NO" icon on the lower portion of the display screen 34G as shown in FIG. 43B. The controller 10 thus prompts the user to enter a verification input as to whether the user is sure of the selected mode.

If the "YES" icon is selected on the verification window of FIG. 43B, the use mode of the selected replay music list is thus determined. If the "NO" icon is selected, the controller 10 controls the display circuit 33, thereby displaying the input window of FIG. 43A to allow the user to select the use mode of the replay music list.

Input Window of the Exercise Information

FIGS. 44A and 44B and FIGS. 45A and 45B illustrate examples of the input window and the verification window for use in step S606 of FIG. 40. FIGS. 44A and 44B illustrate the input window of the exercise information in which the mode of automatically generating the replay music list driven by the personal profile information, etc. is selected as a use mode of the replay music list. FIGS. 45A and 45B illustrate the input window of the exercise information in which the mode of automatically generating the replay music list driven by the target exercise amount is selected as a use mode of the replay music list.

Described with reference to FIGS. 44A and 44B is the input window of the exercise information in which the mode of automatically generating the replay music list driven by the personal profile information, etc. is selected as a use mode of the replay music list. In step S606 of FIG. 40, the input window of the exercise information of FIG. 44A is displayed on the display screen 34G of the display 34. The input window of the exercise information of FIG. 44A includes input boxes for the type of the exercise, the exercise mode, the average speed, and the exercise time.

The type of the exercise indicates the type of the exercise the user is going to practice, such as walking, jogging, running, dash, or strolling. The exercise mode, preset for use, is the hill mode, the constant mode, the random mode, the complex mode, or a combination thereof.

The average speed indicates an approximate speed of the exercise the user is going to practice. For example, the average speed is about 4 km/h for walking, about 10 km/h for jogging, and about 20 km/h for running. The exercise time is time the user plans to play continuously the exercise. If the user intends to exercise for 30 minutes, for example, the user inputs 30 minutes.

When the input boxes on the input window of FIG. 44A are filled in, the controller 10 shifts to the verification window of FIG. 44B. The "YES" icon and the "NO" icon are displayed on the lower portion of the display screen 34G to prompt the user to input a verification answer as to whether the user is sure of the input data.

If the "YES" icon is selected on the verification window of FIG. 44B, the input information is stored on the RAM 13. If the "NO" icon is selected, the controller 10 controls the display circuit 33, thereby displaying again the input window of FIG. 44A to input the exercise information or to modify the input data.

Described below with reference to FIGS. 45A and 45B is the input window of the exercise information in which the mode of automatically generating the replay music list driven the target exercise amount is selected as a use mode of the replay music list. In step S606 of FIG. 40, the input window of the exercise information of FIG. 45A is displayed on the display screen 34G of the display 34. The input window of the exercise information of FIG. 45A includes input boxes for the type of the exercise, the exercise mode, the average speed, and the target exercise time.

The type of the exercise, the exercise mode, and the average speed are identical to those described with reference to FIGS. 44A and 44B. In FIG. 45A, an input box for the target exercise amount is arranged. As the audio reproducing apparatuses of the first and second embodiments, the audio reproducing apparatus of the third embodiment allows an amount of consumed energy (kcal) in the exercise as the target exercise amount information to be input.

When all data is entered in the input boxes of the input window of FIG. 45A, the controller 10 shifts to the verification window of FIG. 45B. The "YES" icon and the "NO" icon are displayed on the lower portion of the display screen 34G to prompt the user to input a verification answer as to whether the user is sure of the input data.

If the "YES" icon is selected on the verification window of FIG. 45B, the input information is stored on the RAM 13. If the "NO" icon is selected, the controller 10 controls the display circuit 33, thereby displaying again the input window of FIG. 45A to input the exercise information or to modify the input data.

To enter data in each of the input items in FIGS. 44A and 45A, the user opens a pull-up menu or a pull-down menu by placing a cursor on each input box and selects information in the menu to input the information. Alternatively, information may be directly input to the input box.

Figure 46:
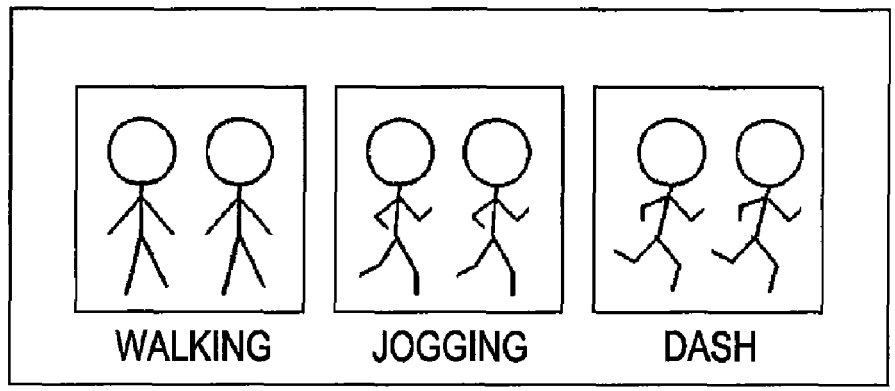
FIG. 46 illustrates an example of a selection window of a type of exercise.
Figure 47:
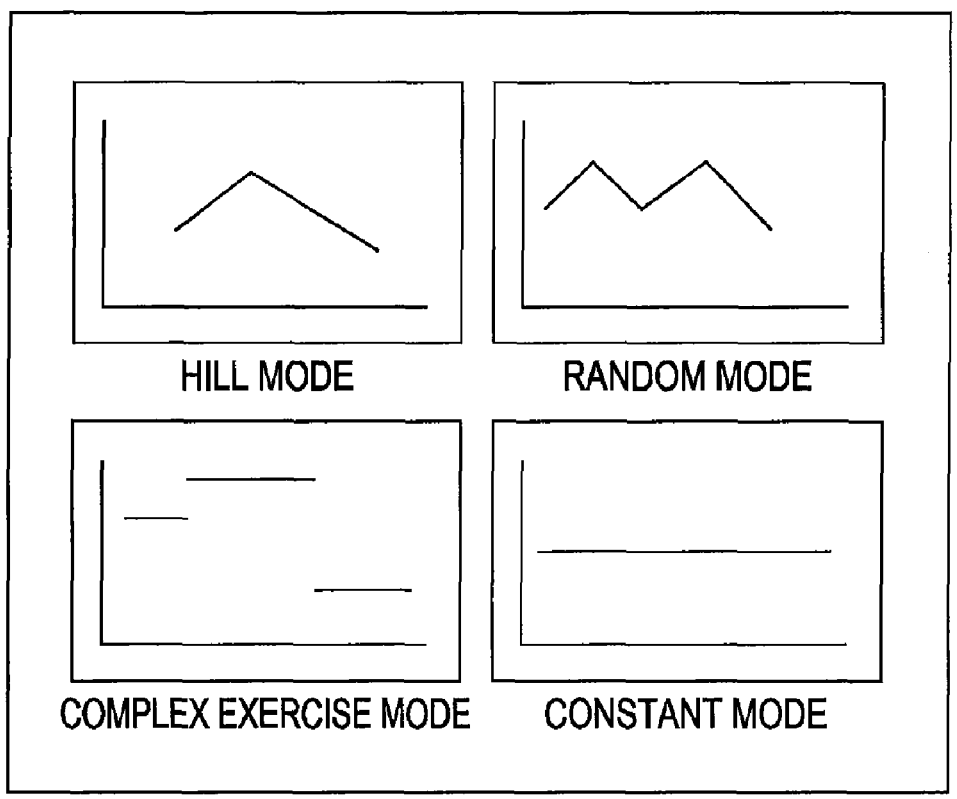
FIG. 47 illustrates an example of the selection window of the type of exercise.

When the cursor is placed on the input box of the type of the exercise, a selection window of the exercise type is displayed as shown in FIG. 46. The selection of the type of the exercise may be selected on the selection window. Also, the cursor may be placed on the input box of the exercise mode to display the selection window of the exercise mode as shown in FIG. 47, and the exercise mode may be selected on the selection window. The use of the selection windows dedicated to predetermined information as shown in FIGS. 46 and 47 helps the user operate easily the audio reproducing apparatus. Art easy-to-operate audio reproducing apparatus is thus provided.

Display of the Replay Music Information

FIGS. 48 and 49 illustrate the replay music information acquired by the controller 10 in step S607 of FIG. 40. FIG. 48 illustrates an example of the replay music information that is acquired when the mode of automatically generating the replay music list driven by the personal profile information, etc. is selected as the use mode of the replay music list. FIG. 49 illustrates an example of the replay music information that is acquired when the mode of automatically generating the replay music list driven by the target exercise amount is selected as the use mode of the replay music list.

By the comparison of FIG. 48 with FIG. 49, the target exercise amount is monitored by consumed calories when the mode of automatically generating the replay music list driven by the target exercise amount is selected. FIG. 49 lists information indicating the calories consumed when the user exercises to the reproduced audio of the music data.

As shown in FIGS. 48 and 49, the replay music information is acquired in the form of a list of the usable music data. The replay music list in accordance with the exercise mode is automatically generated from the replay music information in a relatively easy way as previously discussed.

Selection Window 1 of the Replay Music List

FIGS. 50A-50C illustrate a display screen of the automatically generated replay music list indicated in step S608 of FIG. 40. The replay music list is indicated when the mode of automatically generating the replay music list driven by the personal profile information, etc. is selected as the use mode of the replay music list.

When the mode of automatically generating the replay music list driven by the personal profile information, etc. is selected as the use mode of the replay music list, the controller 10 controls the display circuit 33 in step S608 of FIG. 40, thereby displaying on the display screen 34G of the display 34 the input window for selecting the replay music list (referred to as play list) of FIG. 50A. As shown in FIG. 50A, the input window for selecting the replay music list displays the number of automatically generated replayable replay music lists while also a selection input box to select which replay music list to be displayed. The selection input is received via the keyboard 41.

When the selection input of the replay music list to be displayed is received on the input window of FIG. 50A, the controller 10 controls the display circuit 33, thereby shifting the display screen of the display 34 to the verification window of FIG. 50B. As shown in FIG. 50B, the verification window displays a replay music list number selected on the preceding input window (FIG. 50A), and a "YES" icon and a "NO" icon for receiving verification inputs on the lower portion of the display 34. The controller 10 thus prompts the user to enter a verification input as to whether the user is sure of the selected replay music list number.

If the "YES" icon is selected on the verification window of FIG. 50B, information to form the selected replay music list is read from the storage unit 53 and supplied to the display circuit 33. As shown in FIG. 50C, the selected replay music list is displayed on the display screen 34G of the display 34. After verifying and deciding to use the displayed replay music list, the user performs a predetermined operation such as pressing an enter key. The use of the displayed replay music list, is thus determined.

If the "NO" icon is selected, the controller 10 controls the display circuit 33, thereby displaying again the input window of FIG. 50A to allow the user to select, again the replay music list.

Selection Window 2 of the Replay Music List

FIGS. 51A and 51B illustrate a display screen of the preset replay music list indicated in step S608 of FIG. 40. The replay music list is indicated when the mode of automatically generating the replay music list driven by the personal profile information, etc. is selected as the use mode of the replay music list.

When the mode of automatically generating the replay music list driven by the personal profile information, etc. is selected as the use mode of the replay music list, a preset replay music list may be present. In such a case, in step S608 of FIG. 40, the controller 10 controls the display circuit 33, thereby displaying on the display screen 34G of the display 34 a verification window for determining whether the preset replay music list of FIG. 51A (referred to as play list as shown) is to be used.

The verification window of FIG. 51A displays on the lower portion of the display screen 34G an "YES" icon and a "NO" icon receiving a verification input as to whether the preset replay music list is to be used or not. The verification window thus receives via the keyboard 41 the verification input as to whether the preset replay music list is to be used.

If the "YES" icon is selected on the verification window of FIG. 51A, information to form the preset replay music list of FIG. 51B is read from the storage unit 53 and supplied to the display circuit 33. The preset replay music list is displayed on the display screen 34G of the display 34. After verifying and deciding to use the displayed replay music list, the user performs a predetermined operation such as pressing the enter key. The use of the displayed replay music list is thus determined.

If the "NO" icon is selected, the controller 10 controls the display circuit 33, thereby shifting to the input window for selecting the automatically generated replay music list of FIG. 50A to allow the user to use the automatically generated replay music list.

There might be a plurality of preset replay music lists. For example, there might be a plurality of preset replay music lists such as the replay music list for 30 minute walking and the replay music list for 30 minute jogging as shown in FIGS. 27A and 27B. As previously discussed with reference to FIGS. 50A through 50C, the controller 10 notifies of the total number of preset replay music lists as when there are a plurality of automatically set replay music lists. The controller 10 then receives a selection input as to which replay music list to use (FIG. 50A), prompts the user to input the selected replay music list number (FIG. 50B), displays the preset replay music list selected when verified (FIG. 50C), and then determines the replay music list.

Display Example of the Replay Music List

FIGS. 52-54 illustrate display examples of the replay music list. The examples of the automatically generated replay music lists are discussed here. As previously discussed, the audio reproducing apparatus of the third embodiment can use any of the four modes including the hill mode, the constant mode, the random mode, and the complex mode. When the mode of automatically generating the replay music list driven by the personal profile information, etc. is selected as the use mode of the replay music list, the replay music list may be automatically generated on a per exercise mode of the above four modes.

As previously discussed with reference to FIGS. 50A through 50C, each of the four automatically generated replay music lists is displayed in response to the selection input by the user in step S608 of FIG. 40. For example, when the replay music list generated in the hill mode is selected, a waveform diagram characteristic of the exercise mode and the content of the replay music list listing the title, the length (play time), the song tempo, and the number of plays of the reproduced music data are displayed as shown in FIG. 50C and FIG. 52. As shown in FIG. 52, the music list is identical in display content to the replay music list 1 of FIG. 24A.

When the replay music list generated in the constant mode is selected, a waveform diagram characteristic of the exercise mode and the content of the replay music list are displayed as shown in FIG. 53. The music list of FIG. 53 is identical in display content to the replay music list 2 of FIG. 25A.

When the replay music list generated in the random mode is selected, a waveform diagram characteristic of the exercise mode and the content of the replay music list are displayed as shown in FIG. 54. The music list of FIG. 54 is identical in display content to the replay music list 3 of FIG. 26A.

When the replay music list generated in the complex mode is displayed, a waveform diagram characteristic of the exercise mode and the content of the replay music list are displayed as shown in FIG. 55. The content of the music list of FIG. 55 is a command to play five plays of a song B, five plays of a song E, and five plays of a song F in that order.

Modification Window 1 of the Replay Music List

Figure 56D:
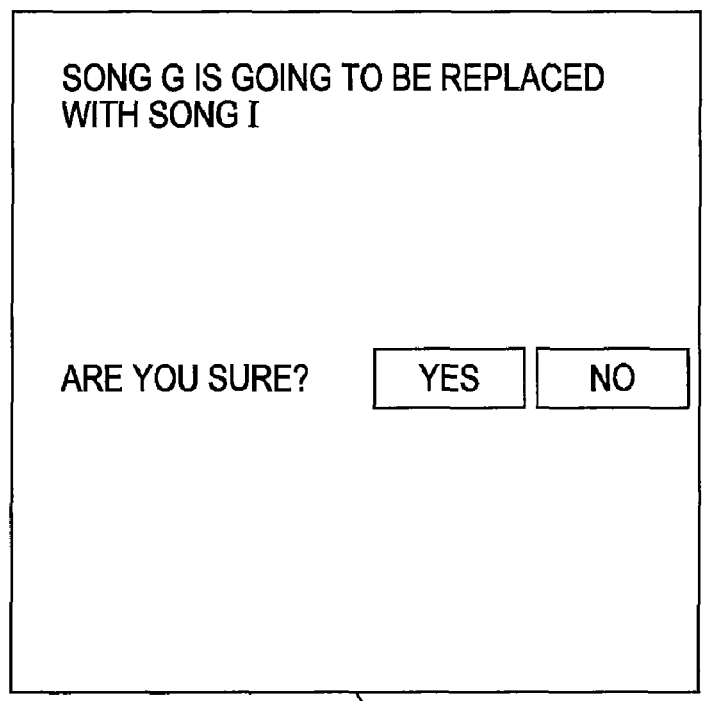
FIG. 56D illustrates an example of the display screen used to modify the selected replay music list.

FIGS. 56A and 56D illustrate a display screen for modifying a selected replay music list (play list) for use in step S609 of FIG. 40. The replay music list is indicated when the mode of automatically generating the replay music list driven by the personal profile information, etc. is selected as the use mode of the replay music list.

The mode of automatically generating the replay music list driven by the personal profile information, etc. is selected as the use mode of the replay music list, and the replay music list (play list) to be used is selected and determined in step S608 of FIG. 40 as discussed with reference to FIGS. 50A-50C and FIGS. 51A and 51B. The display circuit 33 displays on the display screen 34G of the display 34 the input window for receiving a selection input as to whether the selected replay music list is modified or not.

The input window of FIG. 56A displays on the lower portion of the display screen 34G a "YES" icon and a "NO" icon for receiving a verification input as to whether the selected replay music list is to be modified or not. The controller 10 thus receives the verification input as to whether the selected replay music list is to be modified or not.

If the "NO" icon is selected on the input window of FIG. 56A, the controller 10 ends the process in step S609 of FIG. 40 without modifying the selected replay music list. If the "YES" icon is selected on the input window of FIG. 56A, information to form the selected replay music list is read from the storage unit 53 and then supplied to the display circuit 33. As shown in FIG. 56B, the selected replay music list is displayed on the display screen 34G of the display 34. A modification input to the displayed replay music list is thus received.

The user enters a modification input to the selected replay music list displayed as shown in FIG. 56B using the keyboard 41. To replace the song G with the song I on a third row of the replay music list, the user places the cursor on the title box at the third row of the replay music list using the keyboard 41 and replaces the song G with the song I. In this case, the music data to be reproduced is modified by displaying the list of usable songs in a pull-down menu and selecting the title of target music data or by directly inputting the title of target music data.

In response to the modification input, the controller 10 controls the display circuit 33, thereby displaying on the display screen 34G of the display 34 the replay music list modified in response to the modification input as shown in FIG. 56C. As shown in FIG. 56C, the song G at the third row of the displayed replay music list is replaced with the song I. When the title is modified, the length (play time) and the tempo are also modified to the ones matching the new music data.

Similarly, the number of plays in the replay music list is also modified. As necessary, a target row may be deleted in the replay music list or a row may be added to a target position of the replay music list. For example, when a target row is deleted from the displayed replay music list, the cursor may be placed on that target row, and a deletion key may be pressed to delete that target row. The target row is thus deleted. When a row is added to a target position in the replay music list, the user places the cursor on a row immediately preceding the row where the user wants to add the row, and performs a predetermined operation such as pressing an addition key to add the row. A new row is thus added immediately behind row where the cursor is placed so that a title or the number of plays may be input.

Upon receiving the modification input via the keyboard 41, the controller 10 controls the display circuit, thereby displaying the verification window for receiving the verification input of FIG. 56D. In the verification window of FIG. 56D, a "YES" icon and a "NO" icon for receiving a verification input as to whether the modification are correct, or not is displayed on the lower portion of the display screen 34G. The controller 10 thus receives the verification input as to whether the modification thus input is correct or not.

If the "YES" icon is selected on the input window of FIG. 56D, the controller 10 determines that the modification is correct, and ends step S609 of FIG. 40. If the "NO" icon is selected on the input window displayed in FIGS. 56A through 56D, the modified content is not correct. The controller 10 returns to FIG. 56C, thereby permitting the user to modify the replay music list again.

Selection Window 3 of the Replay Music List

FIGS. 57A through 57C illustrate the display screen of the replay music list automatically generated in step S608 of FIG. 40 when the mode of automatically generating the replay music list driven by the target exercise amount is selected as the use mode of the replay music list.

When the mode of automatically generating the replay music list driven by the target exercise amount is selected as the use mode of the replay music list, the controller 10 controls the display circuit 33 in step S608 of FIG. 40. The display circuit 33 thus displays on the display screen 34G of the display 34 the input window for selecting the replay music list (referred to as play list) as shown in FIG. 57A. As shown in FIG. 57A, the input window for selecting the replay music list displays the number of replayable replay music lists automatically generated, and a selection input box for receiving setting of what replay music list to display. The controller 10 then receives the selection input via the keyboard 41.

When the selection input of the displayed replay music list is received on the input window of FIG. 57A, the controller 10 shifts to the verification window of FIG. 57B. In the verification window as shown in FIG. 57B, a replay music list number selected on the preceding input window (FIG. 57A) is displayed. Also, a "YES" icon and a "NO" icon for receiving the verification input are displayed on the lower portion of the display screen 34G. The controller 10 thus prompts the user to enter the verification input as to whether the user is sure of the selected replay music list number.

If the "YES" icon is selected on the verification window of FIG. 57B, information to form the selected replay music list is read from the storage, unit 53 and then supplied to the display circuit 33. The display screen 34G of the display 34 thus displays the selected replay music list. The music list of FIG. 57C is identical in display content to the replay music list 1 of FIG. 32A.

The replay music list of FIG. 57C is automatically generated when the exercise is performed in the hill mode with the target exercise amount is 500 kcal. A replay music list automatically generated as shown in FIGS. 33A-35B in accordance with the second embodiment of the present invention is also available and may be selected and displayed as shown in FIG. 57C.

If the "NO" icon is selected, the controller 10 controls the display circuit 33, thereby displaying again the input window of FIG. 57A to select the replay music list again.

Selection Window 4 of the Replay Music List

FIGS. 58A and 58b illustrate the display screen of the preset replay music list indicated in step S608 of FIG. 40 when the mode of automatically generating the replay music list driven by the target exercise amount is selected as the use mode of the replay music list. When the mode of automatically generating the replay music list driven by the target exercise, amount is selected as the use mode of the replay music list, a preset replay music list may already be present. In step S608 of FIG. 40, the controller 10 controls the display circuit 33, thereby displaying on the display screen 34G of the display 34 the verification window (play list as shown) as to whether the preset replay music list (play list as shown) of FIG. 58A is to be used or not.

As shown in FIG. 58A, a "YES" icon and a "NO" icon for receiving a verification input as to whether the preset replay music list is to be used are displayed on the lower portion of the display screen 34G. The controller 10 thus receives the verification input as to whether the preset replay music list is to be used.

If the "YES" icon is selected on the verification window of FIG. 58A, information to form the preset replay music list of FIG. 58B is read from the storage unit 53 and then supplied to the display circuit 33. The display screen 34G of the display 34 thus displays the preset replay music list. The user then verifies the displayed replay music list and performs a predetermined, operation such as pressing a verification key. The use of the displayed replay music list is thus determined.

If the "NO" icon is selected on the verification window of FIG. 58A, the controller 10 controls the display circuit 33, thereby shifting to the input window for selecting the automatically generated replay music list of FIG. 58A to make the automatically generated replay music list ready for use. The music list of FIG. 58B is identical in display content to the preset replay music list 1 of FIG. 36.

There might be a plurality of preset replay music lists. For example, there might be a plurality of automatically set replay music lists such as those shown in FIGS. 57A through 57C. The controller 10 notifies of the total number of preset replay music lists when there is a plurality of automatically set replay music lists. The controller 10 then receives a selection input as to which replay music list to use (FIG. 57A), prompts the user to input the selected replay music list number (FIG. 57B), displays the preset replay music list selected when verified (FIG. 57C), and then determines the replay music list.

Modification Window 2 of the Replay Music List

FIGS. 59A through 59D illustrate a display screen for modifying the selected replay music list (play list). The replay music list is used in step S609 of FIG. 40 when the mode of automatically generating the replay music list driven by the personal profile information, etc. is selected as the use mode of the replay music list.

Figures 59A, 59B:
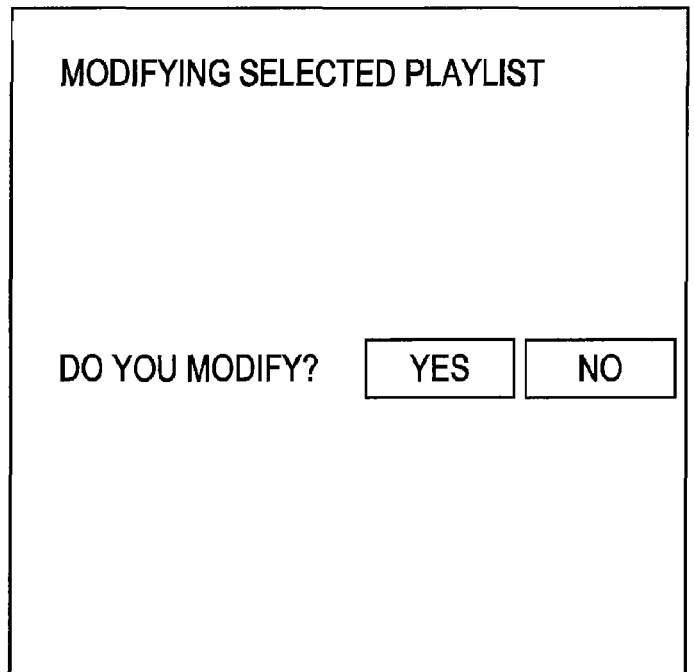
FIG. 59A illustrates an example of a display screen to modify a selected replay music list 1) strolling, (2) walking, (3) jogging, (4) running, and (5) dash.
FIG. 59B illustrates an example of the display screen to modify the selected replay music list.

The mode of automatically generating the replay music list driven by the personal profile information, etc. is selected as the use mode of the replay music list. As described with reference to FIGS. 57A through 57C and FIGS. 58A and 58B, the controller 10 selects and determines in step S608 of FIG. 40 the replay music list (play list) to be used. As shown in FIG. 59A, the controller 10 controls the display circuit 33, thereby displaying on the display screen 34G of the display 34 an input window receiving a selection input as to whether the selected replay music list is to be modified or not.

The input window of FIG. 59A displays on the lower portion of the display screen 34G a "YES" icon and a "NO" icon receiving a verification input as to whether the selected replay music list is to be modified or not. The controller 10 thus receives the verification input as to whether the selected replay music list is to be modified or not.

If the "NO" icon is selected on the input window of FIG. 59A, the controller 10 ends step S609 of FIG. 40 without modifying the replay music list. If the "YES" icon is selected on the input window of FIG. 59A, information to form the selected replay music list is read from the storage unit 53 and supplied to the display circuit 33. The display circuit 33 thus displays the selected replay music list on the display screen 34G of the display 34 as shown in FIG. 59B. The controller 10 receives the modification input to the displayed replay music list.

The user enters the modification input to the displayed replay music list as shown in FIG. 59B using the keyboard 41. To replace a song C with a song H at a third row of the replay music list, for example, the user uses the keyboard 41 to place a cursor on a title box at the third row of the displayed replay music list and to enter the modification input to replace the song C with the song H. In this case, the user can also modify the music data to be reproduced, by displaying a list of usable songs in a pull-down menu format and selecting a title of target music data or by directly entering the title of the target music data.

In response to the modification input, the controller 10 controls the display circuit 33, thereby displaying the replay music list modified in response to the modification input on the display screen 34G of the display 34 as shown in FIG. 59C. In FIG. 59C, the song B at the third row of the displayed replay music list is replaced with the song H. When the title is changed, the length (play time), and the tempo are also automatically modified to those matching the new music data.

Similarly, the number of plays in the replay music list is also modified. As necessary, a target row may be deleted in the replay music list or a row may be added to a target position of the replay music list in the same way as previously discussed with reference to FIGS. 56A through 56D.

Upon receiving the modification input via the keyboard 41, the controller 10 controls the display circuit, thereby displaying the verification window for receiving the verification input of FIG. 59D. In the verification window of FIG. 59D, a "YES" icon and a "NO" icon for receiving a verification input as to whether the modification is correct or not are displayed on the lower portion of the display screen 34G. The controller 10 thus receives the verification input as to whether the modification thus input is correct or not.

If the "YES" icon is selected on the input window of FIG. 59D, the controller 10 determines that the modification is correct, and ends step S609 of FIG. 40. If the "NO" icon is selected on the input window displayed in FIG. 59D, the modified content is not correct. The controller 10 returns to FIG. 59C, thereby permitting the user to modify the replay music list again.

In this way, the audio reproducing apparatus of the third embodiment receives a variety of information and commands relatively easily using a variety of windows, and performs intended processes.

The audio reproducing apparatus of the third embodiment may be implemented in a variety of sizes. The user interface, such as the structure of the keyboard and the display format of information, may be also implemented in a variety of forms. User friendliness is achieved by indicating information in an easy-to-understand fashion, and facilitating input operation.

As the audio reproducing apparatuses of the first and second embodiments, the audio reproducing apparatus of the third embodiment motivates the user to exercise on a regular basis, and allows the user to play comfortably an exercise that may require playing on a regular basis. The user can thus enjoy exercising. Since the play history information, the personal profile information, and the exercise amount information can be managed by the audio reproducing apparatus for the user's personal use, personal information of the user is securely managed.

The audio reproducing apparatus of the third embodiment includes the storage unit 53. As previously discussed, the storage unit 53 may store the personal profile information, the exercise amount information, and the replay music information, etc. for later retrieval for a variety of analyses.

By inputting information regarding the target energy to be consumed, a required amount of exercise is displayed in the music data to be reproduced and the number plays of the music data with respect to the consumed calories of the music data. The music data may be reproduced as displayed, and the user may walk or jog to the reproduced music. When all the music data to be reproduced is played by the displayed number of times, the user can finish the exercise of the target consumed calories. By simply exercising to the reproduced music, the user can achieve the target exercise amount.

The audio reproducing apparatus of the present invention may be relatively easily implemented by producing the program for the process discussed with reference to FIGS. 40 and 41 and loading the program on one of a variety of audio reproducing apparatuses.

In the third embodiment of the present invention, the exercise, amount information and the target exercise amount information may include the exercise time, the exercise intensity, the exercise distance, and the burned fat amount in addition to the consumed calories. For example, when the exercise time is used as the target exercise amount information, the time throughout which the exercise is desired to be continued (exercise time) is input as the target exercise amount information. The music data is selected to have the play time indicated by the input time information. When the consumed fat amount is input as the target exercise amount information, the music data to be reproduced is selected and determined to burn the input burned fat amount.

When the music data to be reproduced is selected and determined, the type (genre), the tempo, the combination, and the number of plays of the music data to be reproduced may be automatically determined. For example, by attaching information indicating the genre to the characteristic information of the music data, the music data of the genre appropriate for the target exercise amount can be selected. The tempo, the combination, and the number of plays may also be automatically determined based on the target exercise amount.

If the replay music information discussed with reference to FIGS. 48 and 49 contains information regarding the exercise intensity such as the consumed energy for each exercise, a detailed process may be performed on a per exercise basis. The type of exercise may be defined by the type, such as walking, jogging, running, jump rope, and the exercise intensity may be defined by the speed of exercise.

As previously discussed, the replayable music data may be supplied in the recorded state thereof on a recording medium such as a CD (Compact Disk), an MD (Mini Disc), a card memory, or the like. The recording medium is then loaded on the music information storage unit 21 and the replayable music data is read and reproduced. The replayable music data may be acquired via the communication I/F 61 and the transceiver circuit 62 in communication with a server over a network or a wireless LAN, and then recorded on the recording medium of the music information storage unit 21. The music data may be directly reproduced from an external device connected to the external terminal 51 or the music data from the external device may be recorded on the recording medium of the music information storage unit 21 and then reproduced from the recording medium of the music information storage unit 21.

As described above, the characteristic information of the music data, such as the play time, the tempo, and the consumed calories responsive to the exercise information may be supplied in the recorded state thereof on a recording medium together with the music data. The characteristic information, together with the music data or separately from the music data, may be supplied via a wide area network such as the Internet or a wireless LAN, or from an external device connected to the external terminal 51. The music data and the characteristic information thereof may be separately acquired if the music data and the characteristic information are associated with each other by identification information (ID) of the music data.

The audio reproducing apparatus of the third embodiment is a mobile music reproducing apparatus. More specifically, the audio reproducing apparatus is applicable to a variety of types of apparatuses including a hard disk player, an MD player, and a cellular phone. The present invention is appropriate for use in a mobile apparatus. The audio reproducing apparatus may be used in a stationary fashion. For example, the audio reproducing apparatus may be mounted on a variety of fitness machines for the compact design thereof.

Modification Input of the Exercise Mode

In accordance with the above-described embodiments, exercise modes such as the hill mode, the constant mode, the random mode, and the complex mode are available as the exercise mode for playing the exercise at a predetermined load pattern. The load pattern (exercise pattern) typically predetermined on each exercise mode may be modified.

Figure 60:
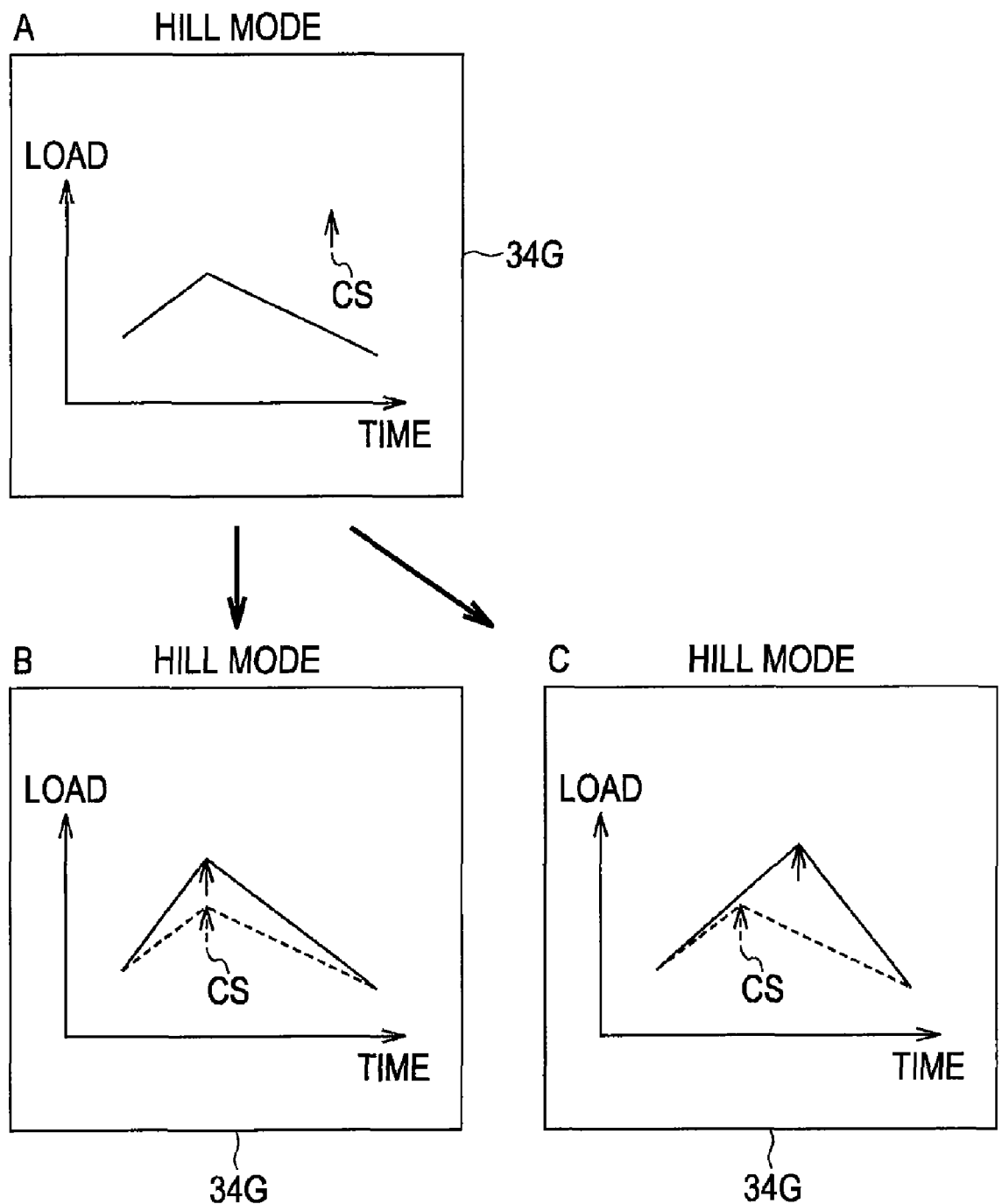
FIG. 60 illustrates a pattern modification of an exercise mode (hill mode).

FIGS. 60 and 61 illustrate the pattern modification of the exercise mode. The exercise pattern of the hill mode is now modified. When a predetermined operation is performed to display the pattern of the hill mode on the display screen 34G of the display 34, the controller 10 controls the display circuit 33. The display circuit 33 thus displays a current exercise pattern waveform of the hill mode and a cursor CS on the display screen 34G as shown in portion A of FIG. 60.

When the load is increased, the cursor CS is placed on the peak position of the exercise pattern waveform as shown in portion B of FIG. 61 and then shifted upward. In this way, the exercise pattern waveform is changed in the hill mode so that the magnitude of the load is modified to be larger. To increase the load and shift the peak position, the cursor is placed on the peak position of the exercise pattern waveform and shifted upward while shifted rightward. The exercise pattern waveform is thus changed in the hill mode so that the load is generally increased while the peak position is shifted.

The same method is also applied to the random mode. The load may be increased and the peak position thereof may be shifted. The load may be decreased in each of the hill mode and the random mode.

The modification of the exercise pattern waveform in the complex mode is considered. A predetermined operation is performed to display a pattern of the complex mode on the display screen 34G of the display 34. The controller 10 controls the display circuit 33, thereby displaying a current exercise pattern waveform of the complex mode and the cursor CS on the display screen 34G as shown in portion A of FIG. 61.

To lengthen the exercise time of initial light load, the cursor CS is placed on the end point of the exercise time of the initial light load in the exercise pattern waveform and then shifted rightward. The exercise pattern waveform of the complex mode is thus changed to lengthen the exercise time of the initial light, exercise. As shown in portion B of FIG. 61, the exercise time of next heavy load is shortened by lengthening the exercise time of the first light load. As shown in portion C of FIG. 61, the exercise time of the first light load may be lengthened with the exercise time of the next heave load and a subsequent cool-down time unchanged. Which way to modify the exercise time may be left to a manufacturer of the audio reproducing apparatus or the user.

The cursor CS may be placed on one of the exercise time of the initial light load, the exercise time of the next heavy load and the cool-down time and then moved upward to increase the load level at that time. If the cursor CS is moved downward, the load level at that time may be lowered. The modification (adjustment) of the exercise load may be similarly performed in the constant mode.

In accordance with the first through third embodiments, the user practices a series of exercises including strolling exercise, walking exercise, jogging exercise, running exercise, and dash exercise. In this case, the exercise speed (travel speed) increases in accordance with (1) strolling, (2) walking, (3) jogging, (4) running, and (5) dash in that order, and increases the load on the user in that order. Since the exercise speed (travel speed) in these exercises varies between individuals, it is difficult to standardize speeds by value. Different persons may have different exercise speeds even in the same exercise type.

The categorization of (1) strolling, (2) walking, (3) jogging, (4) running, and (5) dash may apply not only when the user exercises outdoors but also when the user exercises on a treadmill or a bicycle type training machine indoors. The user sets the exercise intensity by the type of exercise on such a machine.

For example, in the exercise on the bicycle type training machine, the user sets (1) strolling exercise to pedal slowly, (2) walking exercise to pedal with a load of walking, (3) jogging exercise to pedal with an appropriate aerobic motion, and (4) running or (5) dash for higher load. Even if the user exercises in different environment, the categorization of (1) strolling, (2) walking, (3) jogging, (4) running, and (5) dash is applied according to the load or tempo. The exercise of the user is thus managed.

An apparatus such as the audio reproducing apparatus of the present invention manages the exercise intensity according to the categorization of 1) strolling, (2) walking, (3) jogging, (4) running, and (5) dash. The audio reproducing apparatus provides the user with reproduced music data to assist the user in a variety of exercises. The user can thus exercise comfortably and continually.

Other Embodiments

The process of the second embodiment illustrated in the flowchart of FIG. 22 and the process of the third embodiment illustrated in FIGS. 40 and 41 allow the type of exercise (categorization) to be input. The present invention is not limited to this. If the calculation of the consumed energy using the METS is not performed, the METS value is not required, and the information indicating the type of exercise is not required either.

In accordance with the first through third embodiments, the type of exercise is received. The present invention is not limited to this method. For example, the exercise the user is going to practice may be automatically selected or preset in any of the apparatuses the present invention is applicable, including the audio reproducing apparatus.

As the audio reproducing apparatus of the first embodiment, the audio reproducing apparatus of one of the second and third embodiments sets the mode of generating the replay music list by selecting songs to be reproduced from the replay music information. The audio reproducing apparatus not only selects and uses one replay music list from the automatically generated replay music list and the prepared replay music list but also generates and uses a new replay music list. The newly generated replay music list is registered and used thereafter as a prepared replay music list.

The audio reproducing apparatus of one of the second and third embodiments modifies the tempo of the reproduced sound as discussed with reference to the first embodiment as shown in FIG. 15.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. An audio reproducing apparatus comprising:
first display means for displaying on a display element an input window for personal profile information relating to the body of a user,
first receiving means for receiving the personal profile information displayed on the input window,
second display means for displaying on the display element a selection window for selecting a replay music list to be used, from among at least one replay music list indicative of the order of reproducing music data of at least one song, and the number of plays of each of the music data of at least one song,
second receiving means for receiving a selection input to the selection window displayed by the second display means,
reproducing control means for controlling reproduction of the music data in accordance with the replay music list selected by the second receiving means,
characteristic information storage means for storing characteristic information relating to usable music data,
calculating means for calculating an amount of exercise of the user who exercises in response to reproduced music data, based on the personal profile information received by the first receiving means and the characteristic information of the reproduced music data stored on the characteristic information storage means,
notification means for notifying of the amount of exercise calculated by the calculating means,
third display means for displaying on the display element a selection window for receiving a selection of a generation mode of the replay music list,
third receiving means for receiving a selection input to the selection window displayed by the third display means,
fourth display means for displaying on the display element an input window for receiving the input of a target exercise amount when the mode for generating the replay music list based on the target exercise amount is selected by the third receiving means,
fourth receiving means for receiving the input of the target exercise amount to the input window displayed by the fourth display means,
fifth display means for displaying on the display element an input window for receiving an input of a type of exercise when a mode other than the mode for generating the replay music list based on the target exercise amount is selected by the third receiving means,
fifth receiving means for receiving the input of the type of the exercise to the input window displayed by the fourth display means,
first list generating means for generating the replay music list in response to the personal profile information received by the first receiving means and the target exercise amount received by the fourth receiving means when the mode for generating the replay music list based on the target exercise amount is selected by the third receiving means, and
second list generating means for generating the replay music list in response to the personal profile information received by the first receiving means and the type of the exercise received by the fifth receiving means when the mode other than the mode for generating the replay music list based on the target exercise amount is selected by the third receiving means, wherein the second display means displays the replay music list generated by the first list generating means and the replay music list generated by the second list generating means.

2. The audio reproducing apparatus of claim 1, comprising:
sixth display means for displaying on the display element the content of the replay music list selected by the second receiving means, and
sixth receiving means for receiving a modification input to the content of the replay music list displayed by the sixth display means,
wherein the reproducing control means controls reproduction of the music data in accordance with the replay music list selected by the second receiving means and modified by the sixth receiving means.

3. The audio reproducing apparatus of claim 1, wherein the exercise of the user comprises at least one of walking, jogging, running, and dash.

4. The audio reproducing apparatus of claim 1, wherein the exercise amount information comprises at least one of exercise time, exercise intensity, an amount of exercise, distance exercised, calories consumed, and fat burned.

5. The audio reproducing apparatus of claim 1, wherein the target exercise amount information comprises at least one of exercise time, exercise intensity, an amount of exercise, distance exercised, calories consumed, and fat burned.

6. The audio reproducing apparatus of claim 1, wherein the personal profile information comprises at least one of body height, body weight, age, sex and stride of the user.

7. The audio reproducing apparatus of claim 1, further comprising storage means for storing history information relating to reproduced music data, the history information including at least one of identification information concerning the reproduced music data, the exercise amount information, and the personal profile information.

8. The audio reproducing apparatus of claim 1, wherein the character storage means comprises a recording medium selected from the group consisting of an optical disk, a magneto-optical disk, a magnetic tape, a hard disk, a semiconductor memory, and an IC card.

9. The audio reproducing apparatus of claim 1, further comprising content storage means for storing replayable music data, wherein the content storage means includes a recording medium selected from the group consisting of an optical disk, a magneto-optical disk, a magnetic tape, a hard disk, a semiconductor memory, and an IC card.

10. An audio reproducing method comprising:
a first display step of displaying on a display element an input window for personal profile information relating to the body of a user,
a first receiving step of receiving the personal profile information on the input window displayed in the first display step,
a second display step of displaying on the display element a selection window for selecting a replay music list to be used, from among at least one replay music list indicative of the order of reproducing music data of at least one song, and the number of plays of each of the music data of at least one song,
a second receiving step of receiving a selection input to the selection window displayed in the second display step,
a reproducing control step of controlling reproduction of the music data in accordance with the replay music list selected in the second receiving step,
a calculating step of calculating an amount of exercise of the user who exercises in response to reproduced music data, based on the personal profile information received in the first receiving step and the characteristic information of usable music data stored on predetermined storage means,
a notification step of notifying of the amount of exercise calculated in the calculating step,
a third display step of displaying on the display element a selection window for receiving a selection of a generation mode of the replay music list,
a third receiving step of receiving a selection input to the selection window displayed in the third display step,
a fourth display step of displaying on the display element an input window for receiving the input of a target exercise amount when the mode for generating the replay music list based on the target exercise amount is selected in the third receiving step,
a fourth receiving step of receiving the input of the target exercise amount to the input window displayed in the fourth display step,
a fifth display step of displaying on the display element an input window for receiving an input of a type of exercise when a mode other than the mode for generating the replay music list based on the target exercise amount is selected in the third receiving step,
a fifth receiving step of receiving the input of the type of the exercise to the input window displayed in the fourth display step,
a first list generating step of generating the replay music list in response to the personal profile information received in the first receiving step and the target exercise amount received in the fourth receiving step when the mode for generating the replay music list based on the target exercise amount is selected in the third receiving step, and
a second list generating step of generating the replay music list in response to the personal profile information received in the first receiving step and the type of the exercise received in the fifth receiving step when the mode other than the mode for generating the replay music list based on the target exercise amount is selected in the third receiving step,
wherein the second display step includes displaying the replay music list generated in the first list generating step and the replay music list generated in the second list generating step.

11. The audio reproducing method of claim 10, comprising:
a sixth display step of displaying on the display element the content of the replay music list selected in the second receiving step, and
a sixth receiving step of receiving a modification input to the content of the replay music list displayed in the sixth display step,
wherein the reproducing control step includes controlling reproduction of the music data in accordance with the replay music list selected in the second receiving step and modified in the sixth receiving step.

12. The audio reproducing method of claim 10, wherein the exercise of the user comprises at least one of walking, jogging, running, and dash.

13. The audio reproducing method of claim 10, wherein the exercise amount comprises at least one of exercise time, exercise intensity, an amount of exercise, distance exercised, calories consumed, and fat burned.

14. The audio reproducing method of claim 10, wherein the target exercise amount comprises at least one of exercise time, exercise intensity, an amount of exercise, distance exercised, calories consumed, and fat burned.

15. The audio reproducing method of claim 10, wherein the personal profile information comprises at least one of body height, body weight, age, sex and stride of the user.

16. The audio reproducing method of claim 10, further comprising a storage step of storing, on storage means, history information relating to reproduced music data, the history information including at least one of identification information concerning the reproduced music data, the exercise amount information, and the personal profile information.

17. The audio reproducing method of claim 16, wherein the storage means storing the history information comprises a recording medium selected from the group consisting of an optical disk, a magneto-optical disk, a magnetic tape, a hard disk, a semiconductor memory, and an IC card.

18. The audio reproducing method of claim 10, wherein replayable music data is recorded on a predetermined recording medium, and
wherein the recording medium is selected from the group consisting of an optical disk, a magneto-optical disk, a magnetic tape, a hard disk, a semiconductor memory, and an IC card.

19. A non-transitory computer-readable medium including executable instructions that when executed by a processor perform steps for reproducing music data, said steps comprising:
a first display step of displaying on a display element an input window for personal profile information relating to the body of a user,
a first receiving step of receiving the personal profile information on the input window displayed in the first display step,
a second display step of displaying on the display element a selection window for selecting a replay music list to be used, from among at least one replay music list indicative of the order of reproducing music data of at least one song, and the number of plays of each of the music data of at least one song,
a second receiving step of receiving a selection input to the selection window displayed in the second display step,
a reproducing control step of controlling reproduction of the music data in accordance with the replay music list selected in the second receiving step,
a calculating step of calculating an amount of exercise of the user who exercises in response to reproduced music data, based on the personal profile information received in the first receiving step and characteristic information of usable music data stored on predetermined storage means,
a notification step of notifying of the amount of exercise calculated in the calculating step,
a third display step of displaying on the display element a selection window for receiving a selection of a generation mode of the replay music list,
a third receiving step of receiving a selection input to the selection window displayed in the third display step,
a fourth display step of displaying on the display element an input window for receiving the input of a target exercise amount when the mode for generating the replay music list based on the target exercise amount is selected in the third receiving step,
a fourth receiving step of receiving the input of the target exercise amount to the input window displayed in the fourth display step,
a fifth display step of displaying on the display element an input window for receiving an input of a type of exercise when a mode other than the mode for generating the replay music list based on the target exercise amount is selected in the third receiving step,
a fifth receiving step of receiving the input of the type of the exercise to the input window displayed in the fourth display step,
a first list generating step of generating the replay music list in response to the personal profile information received in the first receiving step and the target exercise amount received in the fourth receiving step when the mode for generating the replay music list based on the target exercise amount is selected in the third receiving step, and
a second list generating step of generating the replay music list in response to the personal profile information received in the first receiving step and the type of the exercise received in the fifth receiving step when the mode other than the mode for generating the replay music list based on the target exercise amount is selected in the third receiving step,
wherein the second display step includes displaying the replay music list generated in the first list generating step and the replay music list generated in the second list generating step.

* * * * *